(12) United States Patent
Sheikh et al.

(10) Patent No.: US 9,051,381 B1
(45) Date of Patent: Jun. 9, 2015

(54) DISEASE-RELATED BIOMARKERS SPECIFIC TO FLORIDA HYBRID BUNCH AND MUSCADINE GRAPE, AND USES THEREOF

(71) Applicant: Florida A&M University, Tallahassee, FL (US)

(72) Inventors: Mehboob B. Sheikh, Tallahassee, FL (US); Devaiah Kambiranda, Tallahassee, FL (US); Hemanth KN. Vasanthaiah, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 14/091,551

(22) Filed: Nov. 27, 2013

Related U.S. Application Data

(60) Provisional application No. 61/730,174, filed on Nov. 27, 2012, provisional application No. 61/730,176, filed on Nov. 27, 2012, provisional application No. 61/730,241, filed on Nov. 27, 2012.

(51) Int. Cl.
*C07K 14/415* (2006.01)
*C12N 9/10* (2006.01)
*C12N 9/42* (2006.01)

(52) U.S. Cl.
CPC ............ *C07K 14/415* (2013.01); *C12N 9/1029* (2013.01); *C12N 9/2442* (2013.01)

(58) Field of Classification Search
None
See application file for complete search history.

(56) References Cited

PUBLICATIONS

Vasanthaiah et al. (Frontiers in the Convergence of Bioscience and Information Technologies, 2007. FBIT 2007, pp. 87-94).*
Chinnasamy. PGPR: Biocontrol and Biofertilization: Chapter 9, A proteomics Perspective on Biocontrol and Plant Defense Michanism. Z.A. Siddiqui Ed. 2006: 233-255. Netherlands: Springer.
Andersen et al., Diurnal variations of amino acids and organic acids in xylem fluid from *Lagerstroemia indica*: an endogenous circadian rhythm. Physiologia Plantarum. 1993. vol. 89: 783-790.doi:10.1111/j.1399-3054.1993. tb05285.x.
Andersen et al., Diurnal Vitiations in Tension, Osmolarity, and the Compositions of Nitrogen and Carbon Assimilates in Xylem Fluid of *Prunus persica*, Vitis Hybrid, and Purys communis. Journal of the American Society for Horticultural Science. 1995. vol. 120 (No. 4): 600-606.
Arichi et al., Effect of stilbene compounds of the root of Polygonum cuspidatum Sieb. Et Zucc on lipid metabolism. Chemical & Pharmaceutical Bulletin. 1982. vol. 30: 1766-1770.
Bannai et al., Extensive feature detection of N-terminal protein sorting signal. Bioinformatics. vol. 18 (No. 2): 298-305, 2002.
Thevenot et al., In vitro tolerance to *Botrytis cinerea* of grapevine 41B rootstock in transgenic plants expressing the stilbene synthase Vst1 gene under the control of a pathogen-inducible PR 10 promoter. J. Exp. Bot. 2001. vol. 52 (No. 358): 901-910.
Basha. Identification of Cultivar Differences in Seed Polypeptide Composition of Peanuts (*Arachis hypogaea* L.) by Two-Dimensional Polyacrylamide Gel Electrophoresis. Plant Physiology. 1979. vol. 63: 301-306.
Basha and Roberts. The Glycoproteins of Plant Seeds. Plant Physiology. 1981. vol. 67: 936-939.
Basha et al., Proteomics Approach to Identify Unique Xylem Sap Proteins in Pierce's Disease-Tolerant Vitis Species. Appl Biochem Biotechnol. 2010. vol. 160: 932-944.
Bhattacharyya et al., Draft of Sequencing and Comparative Genomics of *Xylella fastidiosa* Strains Reveal Novel Biological Insights. Genome Research. 2002. vol. 12: 1556-1563.
Biggs and Grove. Role of the world wide web in extension plant pathology: Case studies in tree fruits and grapes. Plant Dis. 1998. vol. 82 (No. 5): 452-464.
Biles and Abeles. Xylem Sap Proteins. Plant Physiology. 1991. vol. 96: 597-601.
Blein et al., From elicitins to lipid-transfer proteins: A new insight in cell signalling involved in plant defence mechanisms. Trends Plant Sci. 2002. vol. 7 (No. 7): 293-296.
Blom et al., Sequence and structure based prediction of eukaryotic protein phosphorylation sites, Journal of Molecular Biology. 1999. vol. 294: 1351-1362.
Buhtz et al., Xylem sap protein composition is conserved among different plant species. Planta. 2004. vol. 219: 610-618.
Ceccardi et al., A novel protein associated with citrus blight has sequence similarities to expansin. Plant Molecular Biology. 1998. vol. 38: 775-783.
Chivasa et al., Extracellular ATP Functions as an Endogenous Eternal Metabolite Regulating Plant Cell Viability. The Plant Cell. 2005. vol. 17: 3019-3034.
Clarke et al., Evaluation of grape germplasm for resistance to pierce disease and glassy-winged sharpshooter. Proc. Fla. State Hort. Soc. 2003. vol. 116: 32-35.
Trudel et al., Several Thaumatin-Like Proteins Bind to Beta-1, 3-Glucans. Plant Physiology. 1998. vol. 118: 1431-1438.
Dai et al., Histochemical responses of leaves of in vitro plantlets of Vitis spp. To infection with *Plasmopara viticola*. Phytopathology. 1995. vol. 85 (No. 2): 149-154.

(Continued)

*Primary Examiner* — Brent T Page
*Assistant Examiner* — Jared Shapiro
(74) *Attorney, Agent, or Firm* — Nilay J. Choksi; Smith & Hopen, P.A.

(57) ABSTRACT

Isolated disease-related genes from muscadine (*Vitis rotundifolia*) and Florida hybrid bunch grape (*Vitis* spp.) grapes, and complementary DNA associated therewith. The cDNA can be utilized in small RNA technologies to promote expression of disease tolerance-related genes to induce production of disease-tolerance related gene products for resisting disease occurrence in Florida hybrid bunch and *V. vinifera*. The genes include, but are not limited to, stilbene synthase, chalcone synthase, chitinase, PR 4, PR 10, β-1, 3-glucanase, peroxidase, and a subunit of Oxygen-Evolving Enhancer Protein 1. These genes were found to enhance tolerance of Florida hybrid bunch and muscadine grape to a plurality of pathogenic diseases, including, for example, Pierce's disease and anthracnose.

1 Claim, 22 Drawing Sheets

(56) References Cited

PUBLICATIONS

Dalke. New strains of fruit and nut pathogen yield their genomes. Genome News Network. Acessed Feb. 27, 2014. http://www.genomenewsnetwork.org/articles/09_02/xylella.shtml.

Davis et al., Axenic Culture of the Bacteria Associated with Phony Disease of Peach and Plum Leaf Scald. Current Microbiology. 1981. vol. 6: 309-314.

Dron et al., Glutathione and fungal elicitor regulation of a plant defense gene promoter in electroporated protoplasts. Proc. Natl. Acad. Sci. USA. 1988. vol. 85: 6738-6742.

Durrant and Dong. Systemic Acquired Resistance. Annual Review of Phytopathology. vol. 42: 185-209, 2004.

Emanuelsson et al., ChloroP, a neural network-based method for predicting chloroplast transit peptides and their cleavage sites. Protein Science. 1999. vol. 8: 978-984.

Fronttin et al., The proteomics of N-terminal methionine cleavage. Molecular and Cellular Proteomics. 2006. vol. 5 (No. 12): 2336-49.

Giorcelli et al., Expression of the stilbene synthase (StSy) gene from grapevine in transgenic white poplar results in high accumulation of the antioxidant resveratrol glucosides. Transgenic Research. 2004 vol. 13: 203-214.

Gardner and Hewitt. California Central Valley Control Guidelines for Pierce's Disease. Bulletin, Department of Plant Pathology, University of California, Berkley and Davis. 225. Accessed Feb. 27, 2014. http://www.cnr.berkeley.edu/xylella/control/central-valley-guidelines.html.

Gray. New plants for Florida: Grape. Circular 1440. In R. L. Jones, M. L. Duryea & B. J. Treat (Eds.), Florida agricultural experiment station. Gainesville: Institute of Food and Agricultural Sciences. University of Florida. 2003: 10.

Hahlbrock and Scheel. Physiology and molecular biology of phenylpropanoid metabolism. Annu. Rev. Plant Physiol. Plant Mol. Biol. 1989. vol. 40: 347-369.

Hain et al., Disease resistance results from foreign phytoalexin expression in a novel plant, Nature. 1993. vol. 361: 153-156.

Harman et al., *Trichoderma* species—opportunistic, avirulent plant symbionts. Nature Reviews Microbiology. 2004. vol. 2: 43-56.

Hopkins and Purcell. *Xylella fastidiosa*: Cause of Pierce's Disease of Grapevine and Other Emergent Diseases. Plant Disease. vol. 86 (No. 10): 1056-1066, 2002.

Houterman et al., The mixed xylem sap proteome of *Fusarium oxysporum*-infected tomato plants. Molecular Plant Pathology. 2007. vol. 8 (No. 2): 215-221.

Jacobs et al., Induction of different pathogenesis-related cDNAs in grapevine infected with powdery mildew and treated with ethephon. Plant Pathol. 1999. vol. 48: 325-336.

Jeandet et al., Phytoalexins from the *Vitaceae*: Biosynthesis, phytoalexin gene expression in transgenic plants, antifungal activity and metabolism. J. Agr. Food Chem. 2002. vol. 50: 2731-2741.

Katam et al., Protemoic Approach to Screen Peanut Genotypes with Enhanced Nutritional Qualities. Proceedings of the 2007 Frontiers in the Convergence of Bioscience and Information Technologies (FBIT) 2007: 171-178.

Keen and Littlefield. The possible involvement of phytoalexins with resistance gene expression in flax. Physiol. Plant Pathol. 1979. vol. 14: 265-280.

Kehr et al., Analysis of xylem sap proteins from *Brassica Napus*. BMC Plant Biology. vol. 5 (No. 11): 1-13, 2005.

Kimura et al., Effects of stilbenes on arachidonate metabolism in leukocytes. Biochimica et Biophysica Acta. 1985. vol. 834: 275-278.

Van Loon and Van Strien. The families of pathogensis-related proteins, their activities, and comparative analysis of PR-1 type proteins. Physiological and Molecular Plant Pathology. 1999. vol. 55: 85-97.

Kohmoto et al., Correlation between the susceptibility of apple cultivars to *Alternaria mali* and their sensitivity to AM-toxin I. Ann. Phytopath. Soc. Japan. 1977. vol. 43: 65-68.

Lee et al., Functional Characterization of Sequence Motifs in the Transit Peptide of *Arabidopsis* Small Subunit of Rubisco. Plant Physiology. 2006. vol. 140 (Issue 2): 466-483.

Leite et al., Colony aggregation and biofilm formation in xylem chemistry-based media for *Xylella fastidiosa*. FEMS Microbiology Letters. 2004. vol. 230: 283-290.

Lois et al., Small ubiquitin-like modifier modulates abscisic acid signaling in *Arabidopsis*. Plant Cell. 2003. vol. 15: 1347-1359.

Long et al., Further studies on the relationship between glyceollin accumulation and the resistance of soybean leaves to *pseudomonas syringae*. Phytopathology. 1985. vol. 75: 235-239.

Lopez-Millan et al., Effect of Iron Deficiency on the Composition of the Leaf Apoplastic Fluid and Xylem Sap in Sugar beet. Implications for Iron and Carbon Transport. Plant Physiology. 2000. vol. 124: 878-884.

Lorenzo et al., The role of Polygalacturonase-inhibiting proteins (PGIPS) in Defense Against Pathogenic Fungi. Annu. Rev. Phytopathol, 2001. vol. 39: 313-335.

Louime et al., Resistance to Elisnoë ampelina and Expression of Related Resistant Genes in *Vitis rotundiholia* Michx. Grapes. International Journal of Molecular Sciences. 2011. vol. 12: 3473-3488.

Vasanthaiah et al., Characterization of unique and differentially expressed proteins in anthracnose-tolerant Florida hybrid bunch grapes. Appl. Biochem. Biotech. 2009. vol. 157: 395-406.

Yu et al., SUMOsp: a web server for sumoylation site prediction. Nucleic Acids Research. 2006. vol. 34: 254-257.

Vasanthaiah et al., Efficient protocol for isolation of functional RNA from different grape tissue rich in polyphenols and polysaccharides for gene expression. Electronic Journal of Biotechnology. vol. 11 (No. 3): 1-8, 2008.

Montero et al., Trans-resveratrol and grape disease resistance. A dynamical study by high-resolution laser-based techniques. Plant Physiol. 2003. vol. 131: 129-138.

Vijayan et al., A role for jasmonate in pathogen defense of *Arabidopsis*. Proc. Natl. Acad. Sci .USA 1998. vol. 95: 7209-7214.

Muller. Studies on phytoalexins I. The formation and the immunological significance of phytoalexin produced by *Phaseolus vulgaris* in response to infections with *Sclerotinia fructicola* and *Phytophthora infestans*. Aust. J Biol. Sci. 1958. vol. 11 (No. 3): 275-300.

Müller et al., The use of RAPD to characterize Bipolaris sorokiniana isolates. Genet. Mol. Res. 2005. vol. 4 (No. 4): 642-652.

Vasanthaiah et al., A New Stilbene Synthase gene from *Muscadine* (*Vitis rotundifolia*) Grape Berry. Proceedings of the Frontiers in the Convergence of Bioscience and Information Technologies (FBIT). 2007: 87-91.

Olien et al., *Muscadine*—A Classic Southeastern Fruit. HortScience. 1990. vol. 25 (No. 7): 726-831.

Hietakangas et al., PDSM, a motif for phosphorylation-dependent SUMO modification. PNAS USA. 2006. vol. 103 (No. 1): 45-50.

Otani et al., Biological activity of Ak toxin I and II, host specific toxins from *Alternaria alternata* Japanese pear pathotype. Ann. Phytopath. Soc. Japan. 1985. vol. 51: 285-293.

Wang et al., Resistance of Chinese *Vitis* species to *Elsinoe ampelina* (de Bary) shear. HortScience. 1998. vol. 33: 123-126.

Welinder. Superfamily of plant, fungal and bacterial peroxidases. Current Opinion in Structural Biology. 1992. vol. 2: 388-393.

Purcell. California Central Valley Control Guidelines for Pierce's Disease. Date Accessed Jun. 11, 2014. http://www.cnr.berkeley.edu/xylella/control/central-valley-guidelines.html.

Ren and Lu. *Muscadine* rootsctock increased the resistance of Florida hybrid bunch grapes. Proc. Fla. State Hort. Soc. 2002. vol. 115: 108-110.

Rep et al. Mass Spectrometric Identification of Isoforms of PR Proteins in Xylem Sap of Fungus-Infected Tomato. Plant Physiology. 2002. vol. 130: 904-917.

Rep et al. A tomato xylem sap proteibn represents a new family of small cysteine-rich proteins with structural similarity to lipid transfer proteins. FEBS Letters. 2003. vol. 534: 82-86. doi:10.1016/S0014-5793(02)03788-2.

Vasanthaiah et al., Differential expression of chitinase and stilbene synthase genes in Florida hybrid bunch grapes to *Elsinoëampelina* infection. J. Plant Growth Regul. 2010. vol. 61: 127-134.

(56) References Cited

OTHER PUBLICATIONS

Sanders et al., Occurrence of resveratrol in edible peanuts. J. Agr. Food Chem. 2000. vol. 48: 1243-1246.

Schickler and Chet. Heterologous chitinase gene expression to improve plant defense against phytopathogenic fungi. J. Ind. Microbiol. Biotech. 1997. vol. 19: 196-201.

Schwekendiek et al., Hop (*Humulus Lupulus L.*) Transformation with stilbene synthase for increasing resistance against fungal pathogens. Acta Hort. 2005. vol. 668: 101-108.

Shen et al., Proteomics approach to identify wound-response related proteins from rice leaf sheath. Proteomics. 2003. vol. 3: 527-535.

Tamura et al., Photoactivation of the water-oxidizing complex in Photosystem II membranes depleted of Mn, Ca and extrinsic proteins. II. Studies on the Functions of Ca2+. Biochimica et Biophysica Acta. 1989. vol. 976: 173-181.

Terlizzi et al., Detection and molecular characterization of Italian Grapevine rupestris stem pitting-associated virus isolates. Plant Pathol, 2009. vol. 59: 48-58.

* cited by examiner

Fig. 1

DIXIE LAND (MUSCADINE)

LAKE EMERALD (HYBRID)

BUNCH (FIESTA)

DIXIE LAND (MUSCADINE)

LAKE EMERALD (HYBRID)

BUNCH (FIESTA)

*Vitis rotundifolia* DIXIE LAND

*Vitis Spp* LAKE EMERALD

*Vitis vinifera* FIESTA

SEQUENCE LISTING

<160> NUMBER OF SEQ ID NOS: 38

<210> SEQ ID NO 1
<211> LENGTH: 1485
<212> TYPE: DNA
<213> ORGANISM: Vitis rotundifolia

<400> SEQUENCE: 1

| | | | | | |
|---|---|---|---|---|---|
| gccaagggtc | cggccaccat | cctagccatt | ggcacagcta | ctcccgaaca | ctgtgtctac | 60 |
| cagtctgatt | atgctgatta | ctacttcagg | gtcactaaga | gcgagcacat | gactgagttg | 120 |
| aagaagaagt | tcaatcgcat | atgtaagtat | attcatgcat | taattcttat | atacataaca | 180 |
| tttgtaagca | tctaagagtg | tgcgctatta | ggtgaagctg | acctccaagt | gaatgaatgt | 240 |
| ttcaaccttt | ctagagtaaa | gcttttagat | aaattacttg | aggaaacttg | aaaatcattt | 300 |
| tacttcagta | accaatattc | ctttcatttg | actgtaatgg | cttgaagagc | tggttttga | 360 |
| atcatgtagc | attaagaata | accttttata | ctttcttcaa | tgttaaatgc | atgttgatca | 420 |
| tcttgaacaa | tatactatat | aacttgtcga | ttggtaaaac | taatgtgttc | atgttgcttc | 480 |
| atttacaggt | gacaaatcaa | tgatcaagaa | gcgttatatt | cacttgactg | aagaaatgct | 540 |
| tgaggagcac | ccaaacattg | gtgcttatat | ggctccatct | cttaacatac | gccaagagat | 600 |
| tatcactgct | gaggtaccta | gcttggtaa | ggaagcagca | ttgaaggctc | ttaaagagtg | 660 |
| gggccaacca | aagtccaaga | tcacccatct | tgtattttgt | acaacctccg | gtgtagaaat | 720 |
| gcccggtgcg | gattacaaac | tcgctaatct | cttaggcctt | gaaacatcgg | tcagaagagt | 780 |
| gatgttgtac | catcaagggt | gctatgcagg | tggaactgtc | cttcgaaccg | ctaaggatct | 840 |
| tgcagagaat | aatgcaggag | cacgagttct | tgtggtatgc | tctgagatca | ctgttgttac | 900 |
| attccgtggg | ccttccgaag | aagctttgga | ctctttagta | ggccaagcgc | ttttggtgt | 960 |
| tgggtctgca | gctgtgatcg | ttggatcgga | tccagatatc | tcaattgaac | gaccactctt | 1020 |
| ccagctcgtc | tcagcagcca | acatttatt | cctaattcag | caggtgccat | tgccggaaac | 1080 |
| ttacgtgagg | tgggactcac | cttcatttg | tggcctaatg | tgcctacttt | aatttccgag | 1140 |
| aacataggga | aatgcttgac | ccaggctttt | gacccacttg | gtattagcga | ttggaactcg | 1200 |
| ttattttgga | ttgctcaccc | aggtggccct | gcaattctcg | atgcatttga | agcaaaactc | 1260 |
| aatttagaga | aaaagaaact | cgaagcaaca | aggcatgtgt | taagcgagta | cggtaacatg | 1320 |
| tcaagtgcat | gtgtgttgtt | tattatggat | gagatgagaa | agagatcctt | gaaaggggaa | 1380 |
| aaggctacca | caggtgatgg | attggattgg | ggagtattat | tcggttttgg | gccgggcttg | 1440 |
| accatcgaaa | ctgttgtgct | gcatagcatt | cctacagtta | caaat | | 1485 |

<210> SEQ ID NO 2
<211> LENGTH: 31
<212> TYPE: DNA
<213> ORGANISM: Vitis

<400> SEQUENCE: 2
cctttcattc ttcgtggcct caatgtgcct a          31

<210> SEQ ID NO 3
<211> LENGTH: 20
<212> TYPE: DNA
<213> ORGANISM: Vitis

<400> SEQUENCE: 3
tccaacaagc actgaaccag          20

```
<210> SEQ ID NO 4
<211> LENGTH: 20
<212> TYPE: DNA
<213> ORGANISM: Vitis

<400> SEQUENCE: 4
ggcctgacca ttgaaactgt                                               20

<210> SEQ ID NO 5
<211> LENGTH: 20
<212> TYPE: DNA
<213> ORGANISM: Vitis

<400> SEQUENCE: 5
ccaacaagca ctgaaccaga                                               20

<210> SEQ ID NO 6
<211> LENGTH: 20
<212> TYPE: DNA
<213> ORGANISM: Vitis

<400> SEQUENCE: 6
ggcctgacca ttgaaactgt                                               20

<210> SEQ ID NO 7
<211> LENGTH: 34
<212> TYPE: PRT
<213> ORGANISM: Vitis rotundifolia

<400> SEQUENCE: 7

Asn Ile Phe Asn Ala Ile Ser Ala Ala Gly Leu Gly Asn Gln Ile Lys
1               5                   10                  15

Val Ser Thr Ala Ile Asp Thr Gly Val Leu Gly Thr Ser Tyr Pro Pro
            20                  25                  30

Ser Lys

<210> SEQ ID NO 8
<211> LENGTH: 12
<212> TYPE: PRT
<213> ORGANISM: Vitis rotundifolia

<400> SEQUENCE: 8

Thr Asn Ala Glu Asn Glu Phe Val Thr Ile Lys Lys
1               5                   10

<210> SEQ ID NO 9
<211> LENGTH: 61
<212> TYPE: PRT
<213> ORGANISM: Vitis rotundifolia

<400> SEQUENCE: 9

Asp Asn Thr Ala Lys Glu Lys Asp Ser Pro Ala Asn Leu Ser Leu Arg
1               5                   10                  15

Thr Cys Ala Ala Gly Asp Asn Ala Glu Gln Pro Leu Asp Pro Ser Arg
            20                  25                  30

Asn Thr Phe Asp Asn Ala Tyr Tyr Ile Ala Leu Gln Arg Gln Ala Gly
        35                  40                  45

Val Leu Phe Ser Asp Gln Ser Leu Phe Thr Ser Ala Arg
    50                  55                  60
```

```
<210> SEQ ID NO 10
<211> LENGTH: 16
<212> TYPE: PRT
<213> ORGANISM: Vitis

<400> SEQUENCE: 10

Asn Ile Phe Asn Ala Ile Ser Ala Ala Gly Leu Gly Asn Gln Ile Lys
1               5                   10                  15

<210> SEQ ID NO 11
<211> LENGTH: 18
<212> TYPE: PRT
<213> ORGANISM: Vitis

<400> SEQUENCE: 11

Val Ser Thr Ala Ile Asp Thr Gly Val Leu Gly Thr Ser Tyr Pro Pro
1               5                   10                  15

Ser Lys

<210> SEQ ID NO 12
<211> LENGTH: 16
<212> TYPE: PRT
<213> ORGANISM: Vitis

<400> SEQUENCE: 12

Asp Asn Thr Ala Lys Glu Lys Asp Ser Pro Ala Asn Leu Ser Leu Arg
1               5                   10                  15

<210> SEQ ID NO 13
<211> LENGTH: 16
<212> TYPE: PRT
<213> ORGANISM: Vitis

<400> SEQUENCE: 13

Gln Ala Gly Val Leu Phe Ser Asp Gln Ser Leu Phe Thr Ser Ala Arg
1               5                   10                  15

<210> SEQ ID NO 14
<211> LENGTH: 13
<212> TYPE: PRT
<213> ORGANISM: Vitis

<400> SEQUENCE: 14

Asn Thr Phe Asp Asn Ala Tyr Tyr Ile Ala Leu Gln Arg
1               5                   10

<210> SEQ ID NO 15
<211> LENGTH: 16
<212> TYPE: PRT
<213> ORGANISM: Vitis

<400> SEQUENCE: 15

Thr Cys Ala Ala Gly Asp Asn Ala Glu Gln Pro Leu Asp Pro Ser Arg
1               5                   10                  15

<210> SEQ ID NO 16
<211> LENGTH: 12
<212> TYPE: PRT
<213> ORGANISM: Vitis

<400> SEQUENCE: 16

Thr Asn Ala Glu Asn Glu Phe Val Thr Ile Lys Lys
1               5                   10
```

```
<210> SEQ ID NO 17
<211> LENGTH: 12
<212> TYPE: PRT
<213> ORGANISM: Vitis

<400> SEQUENCE: 17

Thr Asn Ala Glu Asn Glu Phe Val Thr Ile Lys Lys
1               5                   10

<210> SEQ ID NO 18
<211> LENGTH: 12
<212> TYPE: PRT
<213> ORGANISM: Vitis

<400> SEQUENCE: 18

Thr Asn Ala Glu Asn Glu Phe Val Thr Ile Lys Lys
1               5                   10

<210> SEQ ID NO 19
<211> LENGTH: 25
<212> TYPE: DNA
<213> ORGANISM: Vitis

<400> SEQUENCE: 19
cacttatgaa tgaagtatct ctgct                                  25

<210> SEQ ID NO 20
<211> LENGTH: 23
<212> TYPE: DNA
<213> ORGANISM: Vitis

<400> SEQUENCE: 20
gagctaggga aaagccatac tgt                                    23

<210> SEQ ID NO 21
<211> LENGTH: 22
<212> TYPE: DNA
<213> ORGANISM: Vitis

<400> SEQUENCE: 21
ttggtatctg attagcgtga tg                                     22

<210> SEQ ID NO 22
<211> LENGTH: 32
<212> TYPE: DNA
<213> ORGANISM: Vitis

<400> SEQUENCE: 22
ccagtacttc ctctggatgt gtctagtcac tc                          32

<210> SEQ ID NO 23
<211> LENGTH: 26
<212> TYPE: DNA
<213> ORGANISM: Vitis

<400> SEQUENCE: 23
agataagctt tgtgtcgtaa gcttgg                                 26

<210> SEQ ID NO 24
<211> LENGTH: 29
<212> TYPE: DNA
<213> ORGANISM: Vitis
```

```
<400> SEQUENCE: 24
tcagcgtgta tgtatcttcc acacagcat                                    29

<210> SEQ ID NO 25
<211> LENGTH: 23
<212> TYPE: DNA
<213> ORGANISM: Vitis

<400> SEQUENCE: 25
tcgtgaaaag agaagggaac tca                                          23

<210> SEQ ID NO 26
<211> LENGTH: 22
<212> TYPE: DNA
<213> ORGANISM: Vitis

<400> SEQUENCE: 26
aaaaacgtct ggaagcaaaa gc                                           22

<210> SEQ ID NO 27
<211> LENGTH: 23
<212> TYPE: DNA
<213> ORGANISM: Vitis

<400> SEQUENCE: 27
ttgctccaga cctgattttt gat                                          23

<210> SEQ ID NO 28
<211> LENGTH: 21
<212> TYPE: DNA
<213> ORGANISM: Vitis

<400> SEQUENCE: 28
tggcacagtt caaacattgc a                                            21

<210> SEQ ID NO 29
<211> LENGTH: 24
<212> TYPE: DNA
<213> ORGANISM: Vitis

<400> SEQUENCE: 29
tgtcctctgt ttacttggtg gtat                                         24

<210> SEQ ID NO 30
<211> LENGTH: 25
<212> TYPE: DNA
<213> ORGANISM: Vitis

<400> SEQUENCE: 30
cttcaagggt aatggtcttc tcaac                                        25

<210> SEQ ID NO 31
<211> LENGTH: 1182
<212> TYPE: DNA
<213> ORGANISM: Vitis

<400> SEQUENCE: 31
atggtgtcag ttgcggaaat tagaaaggcc cagagagctg agggtcccgc cacggttctg    60
gctattggca cggccactcc ggccaactgc gtctaccagg cagactaccc ggattactac   120
ttccggatca ccaacagtga gcacatgacc gagttgaagg agaagttcaa gcgcatgtgt   180
gaaaaatcca tgataaacaa acgctacatg cacctcactg aagaaattct caaggagaac   240
```

-continued

| | |
|---|---|
| cccaacgtct gtgcctacat ggccccatct cttgatgccc gtcaagacat ggtggtggtt | 300 |
| gaagtaccaa agcttggcaa ggaagctgct gccaaggcca tcaaagaatg ggccagcca | 360 |
| aaatccaaga tcacccacct tgtcttctgc accacctccg tgttgacat gcccggtgct | 420 |
| gactatcaac tcaccaagct gctaggcctc aaaccctccg tcaagaggct gatgatgtac | 480 |
| caacagggct gctttgccgg tggcaccgtc ctccgccttg ccaaggatct cgccgagaac | 540 |
| aacgccggct ctcgtgttct ggtcgtctgc tctgaaatca cagctgtcac tttccgaggc | 600 |
| ccgtctgaca cccacttgga ctccctcgtg ggtcaggcac ttttcggtga tggtgcagct | 660 |
| gccgttatca ttggcgcaga cccggatacc aaaattgaac tcccactgtt cgagctcgtc | 720 |
| tccgcggctc agaccatcct ccctgactcc gaaggagcaa tcgacggaca cttgcgtgaa | 780 |
| gtgggcctca cctttcattt actgaaagac gtcccagggt tgatttccaa gaacatagaa | 840 |
| aagagcttgg tggaagcctt cactccgata ggcatcagcg actggaactc cttgttctgg | 900 |
| atagctcacc ccggcggccc agcaatttta gaccaggttg agttaaagct gggtctgaag | 960 |
| gaagagaaac tgagagcaac tcggcacgtt ctgagcgagt atgggaacat gtcgagtgca | 1020 |
| tgcgtgttgt ttatcctgga cgaaatgagg aaaaagtcaa ttgaagaagg gaaaggcagc | 1080 |
| acaggtgaag ggttggaatg gggggtactg tttggattcg gaccaggtct cacggttgag | 1140 |
| actgttgtct tgcacagtgt gtctgcacca gcggctcact ga | 1182 |

<210> SEQ ID NO 32
<211> LENGTH: 1083
<212> TYPE: DNA
<213> ORGANISM: Vitis

<400> SEQUENCE: 32

| | |
|---|---|
| atggctgcaa tggtgcttct tctcgggttt ttattggcaa cccttcagat aacaggagtg | 60 |
| aaatcagtgg gtgtatgcta tggaatgcta ggcaacaatc taccgccagc atcacaagtg | 120 |
| gtagctctgt ataaatctcg caacatcgac cgcatgagaa tctacgatcc aaatcaagca | 180 |
| gctcttcaag cccttagggg ctccaacatt caactcatgc tgggtgtccc aaactcggac | 240 |
| ctccaaggcc tcgccaccaa cccttcccaa gcacagtcat gggttcaaag aaatgtgagg | 300 |
| aactactggc ccggcgtcag tttccggtac atcgcagtcg ggaacgaagt gagtcccgtc | 360 |
| aatggaggca catcacggtt tgcgcagttt gttctgccgg ccatgcgaaa catacgagca | 420 |
| gcactcgcat cagcaggcct ccaggaccga gtcaaggtct ccaccgcaat cgacttaaca | 480 |
| cttctgggca actcctaccc tccatctcaa ggcgctttcc ggggagatgt gaggggttat | 540 |
| ttggatccca tcatccgctt cctggtagac aataagtcgc cgcttctggc gaatatatac | 600 |
| ccttatttcg gctactcagg caaccccaag gacatatctc ttccctacgc tttgttcact | 660 |
| gcaaattcag ttgttgtatg ggacggccag cgcgggtata agaatctgtt cgatgccatg | 720 |
| ctagatgctc tgtactcggc tctggggagg gccgagggg cgtcgttgga ggtggtggtg | 780 |
| tcggagagtg gctggccgtc tgccggggga tttgggacta cggttgataa tgcaaggact | 840 |
| tataattcga atttgatccg ccacgtcaaa ggcgggactc cgaagaggcc aggaagagcc | 900 |
| atagagactt acctctttgc catgtttgat gagaacaaga aggagccgca gttggagaaa | 960 |
| cattttgggc ttttctttcc aaacaaacag ccgaagtact ctatcaactt ttctggagaa | 1020 |
| aaaccttggg atgtgtctac tgaaaatgat acaaatgaag aatccctcaa gagtgacata | 1080 |
| taa | 1083 |

-continued

```
<210> SEQ ID NO 33
<211> LENGTH: 1437
<212> TYPE: DNA
<213> ORGANISM: Vitis

<400> SEQUENCE: 33
ggaaatcaca gccgactcac ccatgacttg gctgtttctg acttggaata tttgggcatc      60
cattgactga cttaaacaac ttttccccat atttctagaa aagtaattca aaaggatgat     120
tacaaaatat cagttgccca tcttgaccgc tggtagcatc ctcctcactc acaaaccaca     180
tgttttaatt tctagtacta ctcagtcttt tgaacaaatg attacaaaat gttttaaggt     240
aaaaataaaa actaaaatcg ctatacgagt ataacataaa aagtaaattt atcttttaaa     300
aaaacgagtt taaaaaaaaa taaagaaagt gttaaaaaaa atcacatttt tatatttatt     360 ttttaaata attgtatttt aataatattt aagaaaaaa acatttttat taagaatatt      420
tctttgttaa ttttgtcttt ttaatgaaaa aaataaaaag ttttaaaata aattttccct     480
tcgtggaata tgagttacgt gtcccacaag gctgattaac tgattcactc caacacacca     540
tgtgaaatgt tgtcctatga agcttgaagc ttgtccatat ttcaaacaac ccgagtcaca     600
atggttgaaa ggtcaaaagc tctaggatcg ttggatcata atcttcagcc ccgagagcct     660
aatttttcgg gtcatcatag gggactcctc tctataaatt cgagaggtga tgaagcaaaa     720
atcattcaac aaaaaaaaat ggagaggaga ggcatatgca aggtggtggt gttgctgtct     780
ctagtggctt gtgccgctgc ccagagcgct agtaatgtga gggccaccta ccattactat     840
aatccggagc aaaatggatg ggacttgaac gcagtgagcg cctactgctc cacttgggat     900
gccagccagc ccttggcatg cgcagcaag tatggatgga ccgccttctg tggaccttct      960
ggtcctactg gccaagctgc ctgtggcaag tgccttagtg taagattcta attatcaaac    1020
aacatctttc tctctctctc tctctcgctc tctctctctc tgtatatata catgtatgta    1080
taacctgaac tatttggggt gtgcaggtga caaacactgc cacaggaact caggcaacgg    1140
tgagaatagt ggaccaatgc agcaatggag gattggattt ggattccgga gtgttcaata    1200
aactagacac taatggggct ggctataacc aaggtcatct tattgtcaat tacgagtttg    1260
tggactgtgg tgactaaacc actgctcccc ttgttcctaa taataagaga ttatggtgca    1320
aaaataaata agcatggagt tagccgcttc ttctgcaata aaatgtagtc aaactttgag    1380
tatggctttg tatgaatttg caagagcgaa aaatcacata taaatctcta tgaattc       1437

<210> SEQ ID NO 34
<211> LENGTH: 1244
<212> TYPE: DNA
<213> ORGANISM: Vitis

<400> SEQUENCE: 34
ttcctgttgt gctctacata tcgtttgcct gcaaatgcac tgaaagtaga aggaaaagtt      60
tctcattaat tggttaatag taagatccac acatttgttt tgttttgttt gtttgccttt     120
tttttctttt tttgcccttt tcccccctct ccgctgagaa agaaagaaaa aaggaattag     180
accaccactt gaatttaacc agccgagacc aacatgagat catagtactc ctttatggaa     240
aaatagtgga ttactttgaa cgttccttag atgcaaccgt atctgccttt gaaaactaga     300
gacacacgtt cacacgaggg aaccttggtc ctccatctat aaatgccaac ccttgttctt     360
agatctcttc tcacctcaaa ccattctctg caaaccaacc aatcctcctc ctcttcctct     420
ttcgatcctt ttcatttcaa actctaagat catgggtgtt tcacttacg agagtgaggt      480
```

```
cacttcctcg gttcccccag ccaagatgtt caaggccgct atcctcgatt ctgacaacct    540
cattcccaag gtaaggcctc aagctatcaa gagtgtggaa atcatacaag gagagggagg    600
ccctggaacc atcaagaaga ttcactttgg tgaaggttag ttttgtatta taatcattgc    660
agcacatata actatcactg catggtatca tgaacatgtt aacagaacag aatagaataa    720
tggaggttct gttttttttc ctctttctgg tgtccaggca gcaaattcaa aagcatgaca    780
caccgggttg atgcgattga caaagagaac ttcacattca gctacactgt ggttgacgga    840
gatgttttga cgggcggcat tgaatcaatt tctcatgagc tcaaagtggt ggcttctcct    900
gatggaggat ccatctacaa gaacaccagc aagtaccaca ccaagggcga tgtagagatc    960
tgtgaagagc acgttaaggg tggcaaagag gaggctctgg aggctctggc attgttcaag   1020
gctatcgaag cctacgtcct ggcacatccc gatgcctatt aagtaaaatt gcctgtagta   1080
attgagatat tagtctcttg agtccacctt catattcatt gcacctatca gtctcaataa   1140
gtttggcctt ttgtgttttt gccatatggc caaagtagcc tcggcttaga aataagagtt   1200
tcccaggtgt gatccttgga gtatttgtga tgttctattg ccat                    1244

<210> SEQ ID NO 35
<211> LENGTH: 775
<212> TYPE: DNA
<213> ORGANISM: V. vinifera

<400> SEQUENCE: 35
taatactcac tcactatatt ggtctttttt tttttttttt ttttttttaaa taacgaaacc     60 ataaaagctt gatgtctcct cgcctgcttt aactacaggt taccaattaa ggaagccctc    120
caacaagcac tgaaccagaa tcatcaagtt taataaagaa taaaaggtgt tacaagtatt    180
atgaaaccaa aaaacatatg tctttatgaa ctcctatttg atttaattgg aaattgtctc    240
attatgattt tcttcactca accatcattt cactcaattt gtagccccag caatgctatg    300
cagcacaaca gtttcaatgg tcaggcctgg cccaaaacca acaaaacac cccagtccaa    360 tccttcacct gtagtggtct tttcttcctt gaccgatttc tttctcatct catccaaaat    420
aaacaacaca catgcgctag acatattccc gtactcactt aagatgtgtc ttgtggcttc    480
aagtttcttc ttctctaaat tgagtcttgc ttcaaccgca tctaggatgg ctgggccacc    540
aggatgagcg atccaaacaa ggagtcccaa tcactaatac caagtgggtc aaaagctggg    600
gtccaacact cctctatatt ctcggagatc agagtaggcc attgggccac aaaatggaaa    660
ggattcccta gtgcggcccg cttgcaaggt cacaccaata tgggaaagcc tccccaaccc    720
ggttgggatc ccataccttg agtattctaa tagttgtcac ctaaatagct ggcgg         775

<210> SEQ ID NO 36
<211> LENGTH: 191
<212> TYPE: PRT
<213> ORGANISM: V. vinifera

<400> SEQUENCE: 36

Met Lys Pro Lys Asn Ile Cys Leu Tyr Glu Leu Leu Phe Asp Leu Ile
1               5                   10                  15

Gly Asn Cys Leu Ile Met Ile Phe Phe Thr Gln Pro Ser Phe His Ser
                20                  25                  30

Ile Cys Ser Pro Ser Asn Ala Met Gln His Asn Ser Phe Asn Gly Gln
            35                  40                  45

Ala Trp Pro Lys Thr Lys Gln Asn Thr Pro Val Gln Ser Phe Thr Cys
        50                  55                  60
```

```
Ser Gly Leu Phe Phe Leu Asp Arg Phe Leu Ser His Leu Ile Gln Asn
 65                  70                  75                  80

Lys Gln His Thr Cys Ala Arg His Ile Pro Val Leu Thr Asp Val Ser
                 85                  90                  95

Cys Gly Phe Lys Phe Leu Leu Leu Ile Glu Ser Cys Phe Asn Arg Ile
                100                 105                 110

Asp Gly Trp Ala Thr Arg Met Ser Asp Pro Asn Lys Glu Ser Gln Ser
            115                 120                 125

Leu Ile Pro Ser Gly Ser Lys Ala Gly Val Gln His Ser Ser Ile Phe
130                 135                 140

Ser Glu Ile Arg Val Gly His Trp Ala Thr Lys Trp Lys Gly Phe Pro
145                 150                 155                 160

Ser Ala Ala Arg Leu Gln Gly His Thr Asn Met Gly Lys Pro Pro Gln
                165                 170                 175

Pro Gly Trp Asp Pro Ile Pro Val Phe Leu Ser Pro Lys Leu Ala
            180                 185                 190

<210> SEQ ID NO 37
<211> LENGTH: 20
<212> TYPE: DNA
<213> ORGANISM: Artificial Sequence
<220> FEATURE:
<223> OTHER INFORMATION: Isolated from Elsinoe ampelina

<400> SEQUENCE: 37
tccgtaggtg aacctgcgga                                                    20

<210> SEQ ID NO 38
<211> LENGTH: 20
<212> TYPE: DNA
<213> ORGANISM: Artificial sequence
<220> FEATURE:
<223> OTHER INFORMATION: Isolated from Elsinoe ampelina

<400> SEQUENCE: 38
tcctacctga tccgaggtca                                                    20
```

DISEASE-RELATED BIOMARKERS SPECIFIC TO FLORIDA HYBRID BUNCH AND MUSCADINE GRAPE, AND USES THEREOF

CROSS-REFERENCE TO RELATED APPLICATIONS

This nonprovisional application is a continuation of and claims priority to U.S. Provisional Application No. 61/730,174, entitled "Isolation of Stilbene Synthase Gene Specific to Muscadine (*Vitis rotundifolia* Michx.) Grape", filed Nov. 27, 2012, to U.S. Provisional Application No. 61/730,176, entitled "Identification and Characterization of PD-Tolerance Related Proteins in Muscadine Grape Xylem Sap", filed Nov. 27, 2012, and to U.S. Provisional Application No. 61/730,241, entitled "Identification and Characterization of Genes Associated with Anthracnose Tolerance filed Nov. 27, 2012, all of which are incorporated by reference in their entireties.

FEDERALLY SPONSORED RESEARCH OR DEVELOPMENT

This invention was made with Government support under Grant Nos. FLAX 2002-02969 and FLAX 00-005 awarded by the U.S. Department of Agriculture. The government has certain rights in the invention.

BACKGROUND OF THE INVENTION

1. Field of the Invention

This invention relates, generally, to protection against and resistant to pathogen attacks in grapes. More particularly, it relates to novel, isolated proteins found in muscadine grape and Florida hybrid Bunch grape to enhance defense mechanism and tolerance of *V. vinifera* and *Vitis* spp. against *Xylella fastidiosa*, anthracnose, and other pathogenic diseases.

2. Description of the Prior Art

Commercial grape cultivation is dominated by bunch (*Vitis vinifera* L., *Vitis labrusca* L., and other *Vitis* spp.) and Florida hybrid bunch grape (*Vitis* spp.) genotypes, while muscadine grape (*V. rotundifolia*) genotypes are underutilized. Muscadine grapes (*V. rotundifolia*) are among the most important *Vitis* species cultivated in the southern United States and have potential for expanded markets in wine and juice production. Generally considered an underutilized commodity, muscadine grapes have a characteristic aroma and sweetness that make them acceptable as table wines, but few reports are available on their biochemical/molecular characteristics. Muscadine grape genotypes contain several unique phenolic compounds that would enable them to resist against microbial infection [2, 8, 11]. In addition, muscadine grapes contain higher levels of polyphenols that are known to have beneficial nutraceutical properties. Resveratrol, as well as other grape phenols like catechins, phenolic acids (gallic acid and caffeic acid), caftaric acid, malvidin-3-glucoside, peonidin-3-glucoside, cyanidin-3-glucoside and epigallocatechin-3 gallate have been linked to the reduced cardiac disease and cancer rates observed in wine drinkers. In addition, they have been reported to reduce low-density lipoprotein (LDL)-cholesterol oxidation, a key component of atherosclerosis. It is believed that because of its highly hydrophilic and lipophilic properties, it can provide more effective protection than other well-known antioxidants, such as vitamins C and E.

Resveratrol (3,4,5-trihydroxystilbene) is a phytoalexin, a class of antimicrobial compounds produced as part of plant's defense system against pathogen infection. Resveratrol is considered a biochemical precursor of viniferins and a major stilbene phytoalexin [14]. Stilbene phytoalexin formation is controlled by stilbene synthase, which comprises a small gene family in most species. At the molecular level, no reports are available on muscadine grape. The knowledge of phenolic composition in grape berries and their health benefits is of importance in relation to food quality and development of value added products.

Phytoalexins are known to be important natural components in the defense of plants against pathogen infection. Since the first report of increased disease resistance in transgenic tobacco plants based on an additional foreign phytoalexin [Stilbene Synthase (STS) from *V. vinifera*] appeared in Nature [7], it has diversified the ways to tackle plant diseases. STS derived from *V. vinifera* was found to be less effective against fungal diseases [14, 1]. Therefore, an embodiment of the current invention isolates and characterizes muscadine stilbene synthase gene, as muscadine grape berries have higher levels of potent polyphenols than the other *Vitis* species.

Stilbene synthase gene was isolated and characterized because resveratrol is present in trans-form in muscadine, which is the most active form. Previous studies have shown significant differences in the phenolics content as well as antioxidant activity among the muscadine genotypes. In addition, seed extracts of muscadine cultivars were found to inhibit colon, lung and breast cancer cells growth by 60% (Basha et al.; Personal communication).

Muscadine grape species are native to southeastern USA [1] and are more tolerant to most diseases including Pierce's disease (PD) than bunch grapes [2]. *V. vinifera* cultivars are highly susceptible to PD [3] while Florida hybrid bunch grape cultivars, which were developed through hybridization of local grape species with the table wine group, *V. vinifera* [4], are also tolerant to PD. But, their tolerance level varies compared to muscadine as the hybrids contain *V. vinifera*, a PD-susceptible species in their parentage. PD is caused by *Xylella fastidiosa* which is vectored by the glassy-winged sharp shooter and thrives in the xylem of grapevines [5]. Through colonization of xylem vessels, *X. fastidiosa* causes vessel clogging leading to wilting of the plant [6]. Xylem sap is known to contain various amino acids, sugars, organic acids, inorganic ions, proteins, and low concentration of organic compounds essential to support bacterial growth [7, 8].

Amino acids and organic acids are predominant organic compounds in xylem fluid of many woody species [9, 10]. The chemistry of xylem fluid is not fixed and can vary with temperature, time of year, light conditions, water stress, and soil nutrient status [8, 10]. Xylem sap is also known to contain proteins in low concentrations [7, 11, 12] and constitutes an environment in which pathogens can grow leading to vessel clogging and eventual death of the grapevine. Resistance and susceptibility of grapevines to PD could be determined by the interactions occurring within the xylem vessels between the *Xylella* and xylem sap components.

In both compatible (susceptible) and incompatible (resistance) plant-microbe interactions, plants respond by secreting their own set of proteins [13]. These proteins may either cause direct damage to invaders or play a protective role through inhibition of cell wall-degrading enzymes secreted by pathogens [14] or through oxygen sequestering to maintain the level of oxygen in xylem sap, which may be altered due to pathogen activity. Recent studies have shown that xylem sap proteins of broccoli, rape, pumpkin, cucumber, and tomato share homologies with several pathogen-related proteins including glycine-rich proteins, peroxidase-like proteins, chitinase-like proteins, serine protease-like proteins, aspartyl proteases, and lipid transfer-like proteins which are active in repair and defense reactions of the plant [15]. In tomato, it has been shown that xylem sap protein patterns change in response to infection by pathogenic fungi, and some of the proteins were identified as pathogenesis-related proteins [11, 12]. In addition, appearance of unique proteins has been documented in xylem sap during development of diseases affecting the vascular system [16]. Hence, xylem sap of infected plants may be a rich information source regarding molecular interaction underlying several plant diseases [13, 17]. While the importance of xylem sap proteins in other crops has been established, very little information is available on *Vitis* xylem sap proteins and their functions.

Anthracnose of grapes (both young leaf and berries) is an economically devastating foliar disease caused by the fungus *Elsinoë ampelina* Shear. Due to the prevailing hot and humid conditions in Florida, this fungus *E. ampelina* thrives and devastates grape crop grown under this environment. Symptoms usually appear as numerous circular spots, which enlarge then become sunken and produce lesions with round edges. Once established in a vineyard, the disease can be very destructive. The pathogenic fungus, which attacks all aerial parts of the plants, such as fruits, leaves, tendrils and petioles, is of considerable economic importance [1-3]. The fungus over-winters in dormant and dead canes, making it very difficult to control. Strategies for the control of anthracnose in grapevines, such as developing resistant cultivars are necessary in order to reduce the production cost and environmental impacts of fungicide applications in areas of high disease pressure. For this purpose, the selection of genetic resources showing tolerance to anthracnose is a prerequisite for any breeding program.

It has been reported that, among the grape species, *V. vinifera* is highly susceptible, while muscadine grapes are mostly tolerant to *E. ampelina* [6,7]. *V. vinifera* is one of the finest grapes grown in the world both for table and wine purposes. On the other hand, native muscadine grapes have been considered as one of the most valuable genetic resources in breeding programs for grape disease tolerance [5, 6, 8-13]. As anthracnose is highly prevalent in this part of the world, it is one of the principal factors preventing the development of a grape industry using *V. vinifera* in the southeastern United States [3]. Growers in this area are forced to grow local species, such as muscadine and Florida hybrid bunch grapes that often compromise the fruit quality. Muscadine grapes have been known for their tolerance or 'tolerance' to many diseases found in bunch (*Euvitis* Planch.) grape species [6,7].

Evaluating and screening of perennial crops, including grapes, for disease tolerance is a constant challenge. Several native grapes and other cultivars (*Vitis* sp.) have been evaluated for their tolerance to anthracnose [4-7]. This process or approach is time-consuming, laborious and costly. Recently, Yun et al. [12] have developed an efficient and reliable screening process for selecting grape cultivars resistant to anthracnose based on pathogen inoculation and by the application of culture filtrates from *E. ampelina*, which is accurate, economical and labor-saving.

As of yet, there have been only two formal reports of anthracnose or its causal agent in muscadine grapes [13,14]. Pierce's disease has prevented growing *V. vinifera* in Floridian and Southeastern United States regions. Muscadine and Florida hybrid bunch grapes (*Vitis* spp.) can be successfully grown as they are tolerant to Pierce's disease, but their tolerance level to anthracnose varies. The breeding work at the Center for Viticulture and Small Fruit Research, Florida Agricultural and Mechanical University, Tallahassee, Fla., USA has been hampered due to lack of knowledge about the anthracnose tolerance levels in muscadine cultivars used in the breeding program. In a study in 2006 and 2007, 21 (40%) of the 51 muscadine cultivars maintained in the vineyard showed anthracnose symptoms, which were found mainly on young leaves and tendrils as circular or irregular black spots. Hence it was necessary to investigate the level of tolerance of the muscadine cultivars at hand, and to use a more stringent screening process to select muscadine genetic resources that are resistant to anthracnose for use in the ongoing breeding process.

Accordingly, what is needed is more effective mechanisms to be incorporating into the breeding programs of *V. vinifera* to fighting against and protecting *V. vinifera* from various pathogenic diseases. However, in view of the art considered as a whole at the time the present invention was made, it was not obvious to those of ordinary skill how the art could be advanced.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

The long-standing but heretofore unfulfilled need for more effective mechanisms of grapes (Florida hybrid bunch and muscadine grape) to fight against and protect itself from various pathogenic diseases is now met by a new, useful and nonobvious invention.

In an embodiment, the current invention includes an isolated cDNA coding for a stilbene synthase gene in Muscadine grape. The cDNA of the stilbene synthase gene includes a nucleotide sequence as set forth in SEQ ID NO: 1.

In an embodiment, the current invention includes an isolated cDNA coding for a chalcone synthase gene in Florida hybrid bunch grape. The cDNA of the chalcone synthase gene includes a nucleotide sequence as set forth in SEQ ID NO:31.

In an embodiment, the current invention includes an isolated cDNA coding for a chitinase gene in Florida hybrid bunch grape. The cDNA of the chitinase gene includes a nucleotide sequence as set forth in SEQ ID NO:32.

In an embodiment, the current invention includes an isolated cDNA coding for a PR 4 gene in Florida hybrid bunch grape. The cDNA of the PR 4 gene includes a nucleotide sequence as set forth in SEQ ID NO:33.

In an embodiment, the current invention includes an isolated cDNA coding for a PR 10 gene in Florida hybrid bunch grape. The cDNA of the PR 10 gene includes a nucleotide sequence as set forth in SEQ ID NO:34.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the nature and objects of the invention, reference should be made to the following detailed disclosure, taken in connection with the accompanying drawings, in which:

FIG. 1 depicts a nucleotide sequence of MSB1 (SEQ ID NO:35) and the deduced amino acid sequence (SEQ ID NO:36) translated from the open reading frame is given in the single letter code. Asterisk denotes the putative termination codon. The N-terminal chloroplast transit peptide (gray highlight), Sumolyation motif (boxed letters) and phosphorylation sites (bold letters) are highlighted;

FIG. 7A shows Dixie Land (*V. rotundifolia*, muscadine grape), FIG. 7B shows Lake Emerald (V. spp) Florida Bunch Hybrid), and FIG. 7C shows Fiesta (*V. vinifera*, bunch grape). Molecular weight standards 97.4 kDa=phosphorylase b; 66.2 kDa=bovine serum albumin; 45.0 kDa=ovalbumin; 31.0 kDa=carbonic anhydrase; 21.5 kDa=soybean trypsin inhibitor and 14.4 kDa=lysozyme. The gel regions exhibiting variation in the polypeptide composition are shown in boxes 1, 2, 3 and 4.

FIG. 9A shows a naturally infected leaf in the vineyard. FIG. 9B shows an artificially infected leaf with pathogen spore suspension. FIG. 9C shows an *Elsinoe* colony on PDA. FIG. 9D shows an *Elsinoe* spores under the microscope (×400). Bar represents 20 µm.

FIG. 12A shows the gel of cultivar Blue Lake (anthracnose-tolerant). FIG. 12B shows the gel of cultivar Suwanee (anthracnose-susceptible).

DETAILED DESCRIPTION OF THE PREFERRED EMBODIMENT

Figure 2:
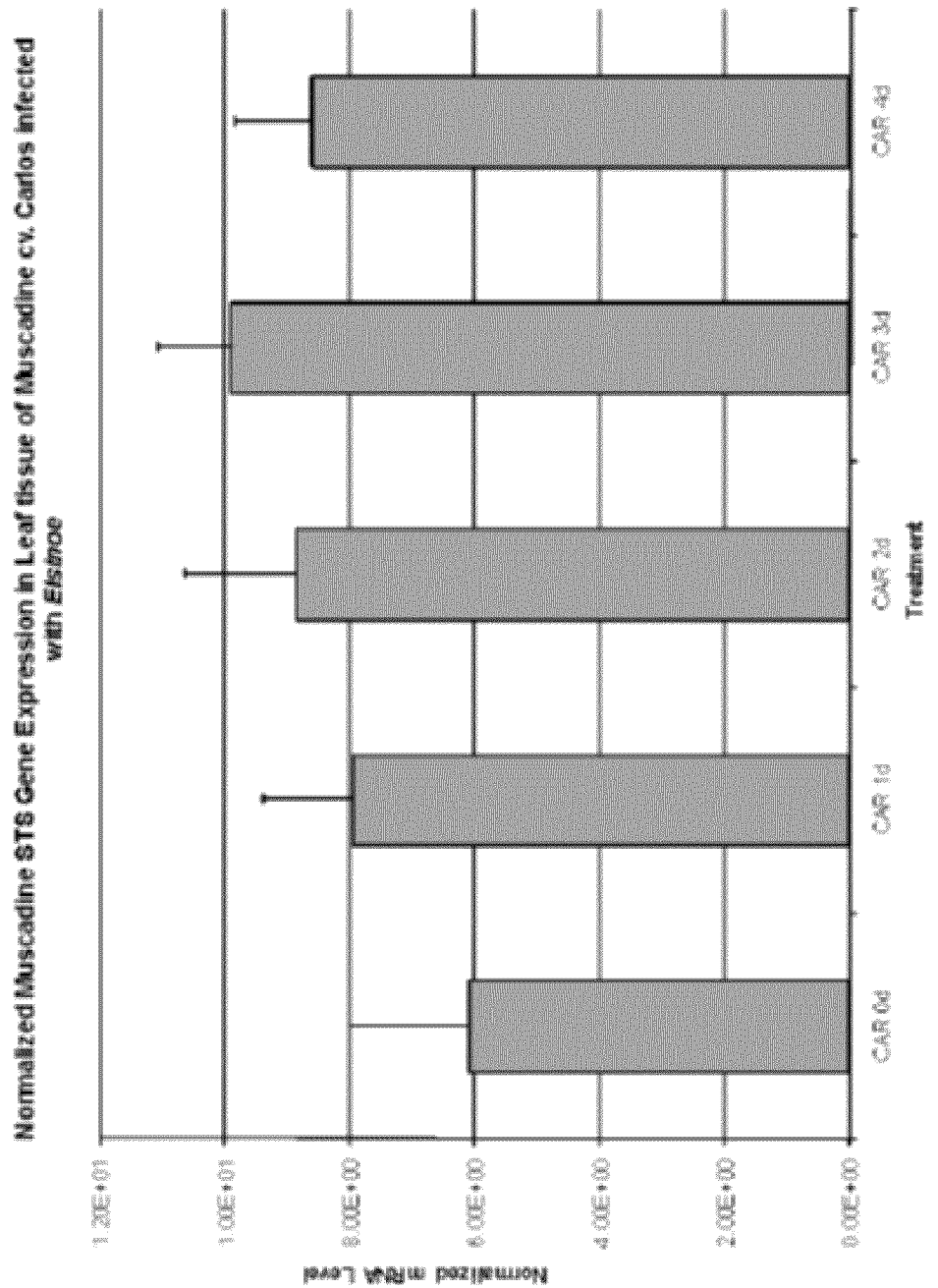
FIG. 2 is a bar graph illustrating the expression level of muscadine stilbene synthase gene (MSB1) upon *Elsinoe* infection during different periods (days) of infection in muscadine cultivar cv. Carlos.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

In an embodiment, the current invention isolates a plurality of previously-unknown disease-related genes in muscadine grape and Florida hybrid bunch grape and creates cDNA from said genes for use in small RNA technologies to promote expression of disease tolerance-related genes to induce production of disease-tolerance related gene products for resisting disease occurrence in *Vitis* spp.

In an embodiment, the current invention includes isolated disease-related genes from muscadine and Florida hybrid bunch grape grapes, and complementary DNA associated therewith. The cDNA can be utilized in small RNA technologies to promote expression of disease tolerance-related genes to induce production of disease-tolerance related gene products for resisting disease occurrence in *Vitis* spp. These muscadine genotypes, compared to other grape species, have the potential to synthesize sufficient amount and type of stilbene phytoalexins in response to a pathogen attack. These genotypes include six isoforms of stilbene synthase genes in muscadine of which two were found different from *V. vinifera* sequence. The invention further includes an MSB gene that screens muscadine grape genotypes to identify the genotypes that have enhanced antifungal and anticancer activity. The current invention further contemplates identifying unique xylem sap proteins present in Pierce's disease-tolerant muscadine cultivars and Florida hybrid bunch grape. γ-1, 3-glucanase, peroxidase, and a subunit of Oxygen-Evolving Enhancer Protein 1 were found to enhance defense mechanism against *X. fastidiosa*, thus enhancing protection against Pierce's disease. The current invention further contemplates isolation of the anthracnose pathogen from the muscadine grapevines to evaluate the disease tolerance potential of muscadine grape genotypes.

I. Isolation of Stilbene Synthase Gene Specific to Muscadine (*Vitis rotundifolia*) Grape Muscadine grapes contain high concentration of polyphenols that are known to have several health benefits. Resveratrol encoded by stilbene synthase is one of the important phenolic compounds found in muscadine grape. It has antibiotic activity against diseases and also has health benefits.

Stilbene synthase gene, isolated from berries of muscadine cv. regale, was amplified by designing several primer combinations to different isoforms of stilbene synthase partial cDNA sequence based on NCBI data. Total RNA isolated from the berries was used for further amplification.

Cloning and sequencing revealed six isoforms of stilbene synthase genes in muscadine, of which two were found different from *V. vinifera* sequence. Further, PCR analysis revealed higher expression of one of the above characterized partial stilbene synthase cDNA. 5' RACE was performed to amplify the full length of this partial gene, which also showed sequence variation with *V. vinifera* STS. Thus, the muscadine genotypes compared to other grape species may have the potential to synthesize sufficient amount and type of stilbene phytoalexins in response to a pathogen attack. This is also beneficial to human health. The expression of this STS gene was also confirmed through real-time PCR after inoculating with *E. ampelina*, which causes anthracnose in grapes.

The cDNA of the novel, isolated stilbene synthase gene is shown in SEQ ID NO: 1.

EXAMPLE

1. Materials and Methods a. Plant Material

Greenhouse grown muscadine cv. Carlos (Anthracnose tolerant) at the Center for Viticulture and Small Fruit Research, Florida Agricultural and Manufacturing University, Tallahassee, Fla., USA was used in this study. Uninfected and infected (anthracnose) leaves were collected at different periods (0, 1, 2, 3, 4 d) after inoculation, frozen in liquid nitrogen and stored at −80° C. until used for RNA isolation. Necrotic spots and curling of leaves were apparent on the infected leaves during sampling.

b. Inoculation

*Elsinoe ampelina* fungi isolated from the infected Blanc du Bois cultivar (Florida hybrid bunch grape) was used in this study. Fungus was isolated after several subcultures, and purity of the culture was confirmed through PCR. Fungi were sporulated on dextrose agar media and used for inoculation. A spore suspension ($1.2 \times 10^6$ spores/ml) was sprayed on both sides of the leaves, and leaf samples were collected everyday till the symptoms started to appear (around day 4-5).

c. RNA Isolation

Total RNA from uninfected and *Elsinoe* infected leaf tissue were isolated using modified guanidine thiocyanate extraction method (Vasanthaiah et al., 2008).

d. Rapid Amplification of cDNA Ends (RACE)

One of the stilbene synthase isoforms (MSB1) out of six isoforms previously isolated and characterized was used in this study (Vasanthaiah and Basha, 2006: NCBI database). This gene is considered to be unique to muscadine based on sequence differences with *V. vinifera* STS.

Primer designing: Based on muscadine STS sequences, primers ranging from 20 to 28 bases in length were designed for amplification of the MSB1 gene. Care was taken to avoid possible secondary structure formation, primer dimer generation and false priming, and also to achieve appropriate melting temperature and internal stability during designing. Regular PCR was performed using these primers to confirm amplification of the gene before carrying out the RACE.

RACE: Stilbene synthase gene specific primers (GSP) for 5'-end were designed as described above (5'-CCTTTCAT(TC)T(TC)GTGGCC(TC)AATGTGCCTA-3' (SEQ ID NO:2)) and RACE was performed to clone full-length cDNA using BD Smart RACE cDNA amplification kit (BD Biosciences Clontech). GSPs having GC content of 50-70% and a $T_m$ of at least 65° C. were designed, which is optimal for further amplification. mRNA recovered from the total RNA of the berries using mRNA purification kit (QIAGEN) was used in further reactions. The first strand cDNA for 5'-RACE was synthesized using a modified lock-docking oligo (dT) primer, BD SMART II A oligo and RT (Reverse Transcriptase). The modified oligo (dT) primer, termed as 5'-RACE CDS Primer (5'-CDS), has two degenerate nucleotide positions at the 3' end. These nucleotides position the primer at the start of the poly A+ tail and thus eliminate the 3' heterogeneity inherent with conventional oligo (dT) priming. Dissociation curve analysis was performed after PCR to look for the expression levels of different transcripts during the course of disease infestation.

e. Analysis

The obtained sequence was further analyzed using various bioinformatics tools by deducing amino acid sequence. The peptide sequence was analyzed using ChloroP server to predict the presence of chloroplast transit peptides (cTP) in protein sequences and the location of potential cTP cleavage sites [5], Netphospo database for identification of protein phosphorylation sites [4], TermiNator to predict Nterminal methionine excision, N-terminal acetylation, Nterminal myristoylation and S-palmitoylation [6], iPSORT database for prediction of N-terminal signal peptide [3] and SUMO plot for prediction of SUMO protein attachment sites [13].

f. Real Time PCR Analysis

Specific primers were designed to the above STS sequence (MSB1; Left 5'-TCCAACAAGCACTGAACCAG-3' (SEQ ID NO:3); Right 5'-GGCCTGACCATTGAAACTGT-3', BS (SEQ ID NO:4); Left 5'-CCAACAAGCACTGAACCAGA-3' (SEQ ID NO:5); Right 5'-GGCCTGACCAT-TGAAACTGT-3' (SEQ ID NO:6)). Care was taken to avoid possible secondary structure formation, primer dimer generation and false priming, and also to achieve appropriate melting temperature and internal stability during designing. A quantitative analysis of this transcript was carried out using Real Time PCR to determine the levels of expression of these transcripts during the course of disease infestation in anthracnose-tolerant genotype (cv. Carlos). Reverse transcription was performed using SuperScript to synthesize first-Strand cDNA (Bio-Rad) and PCR was carried out after normalizing primer concentration and annealing temperature using commercially available kit (Bio-Rad). Total volume of the reaction was 25 μl including RT-PCR mix and 0.5 μM of each primer. Actin was used as the control. Dissociation curve analysis was performed after PCR to look for the expression levels of different transcripts during the course of disease infestation.

2. Results and Discussion

Previously, isolation of STS was accomplished by using reverse transcription polymerase chain reaction (RT-PCR) with oligonucleotide primers designed specific to conserved STS sequences of *Vitis* and other plant genera using total RNA isolated from the berries. The PCR amplification conditions were standardized based on the designed primer. The amplified cDNA were resolved on 2% agarose gel in Tris-borate-EDTA (TBE) buffer and stained with Ethidium Bromide. The specific primer combinations amplifying the targeted gene were selected. The PCR products were cloned into pGEM-T vector (Promega) and sequenced. The sequence data thus obtained were analyzed for its identity based on the BLASTX search for its homology with the sequence of the gene present in NCBI database. Six isoforms of STS gene were isolated from muscadine (Vasanthaiah and Basha, 2006, NCBI database, GenBank Accn EE297448 to EE297453; MSB1-6) cv. Regale. Of these six isoforms, two were found to be similar to *V. vinifera* STS gene (BS) while the other four were different than the *V. vinifera* STS gene and thus appeared to be unique to muscadine.

Of the four isoforms, MSB1 showed maximum sequence variation with *V. vinifera* STS. To this, 5' RACE was performed to amplify full-length gene. However, it was able to amplify only a portion of the gene. The partially amplified gene also showed sequence variation with BS gene. This data clearly indicated that the STS expressed in muscadine berries are different from the ones expressed in *V. vinifera* leaf, which are routinely used to derive disease tolerant transgenic plants. Amino acid sequence of the obtained nucleotide sequence was deduced using Bioedit software and subjected to further analysis using different bioinformatics tools. The predicted amino acid sequence was 198 residues, with open reading frame of 596 nucleotide bases (FIG. 1: SEQ ID NO:35: SEQ ID NO:36). Analysis of this peptide sequence using TermiNator software predicted N-terminus of the mature protein at position 1 (M). It also predicted the translation efficiency of mRNA as 1, which is low and half-life of the protein in the cell as 5 to 31 hours.

ChloroP server predicted chloroplast transit peptide (cTP) at the N-terminal of the protein sequence. The transit peptides of nuclear-encoded chloroplast proteins are necessary and sufficient for targeting and import of proteins into chloroplasts [9]. However, the sequence information encoded by transit peptides is not fully understood. iPSORT predicted the probability of presence of signal peptide in the sequence as 0.951, which is high. Netphospo software predicted phosphorylation sites (four serine and one threonine) at amino acid position 35, 57, 120, 141 and 187.

SUMO (small ubiquitin-like modifier) plot was used to predict SUMO protein attachment sites. SUMO modification is known to regulate many cellular processes, including transcription. The highly conserved motif regulates phosphorylation-dependent sumoylation of multiple substrates (PDSM) such as heat-shock factors (HSFs), GATA-1, and myocyte enhancer factor 2. Majority of the PDSM containing proteins are known to act as transcriptional regulators [12]. The ubiquitin-like protein SUMO also participates in ABA signal transduction. SUMOylation attenuates ABA-mediated growth inhibition and amplified induction of certain ABA- and stress-responsive genes [10]. Analysis of this gene using bioinformatics tools revealed the presence of potential signal peptides in the sequence.

Figure 3:
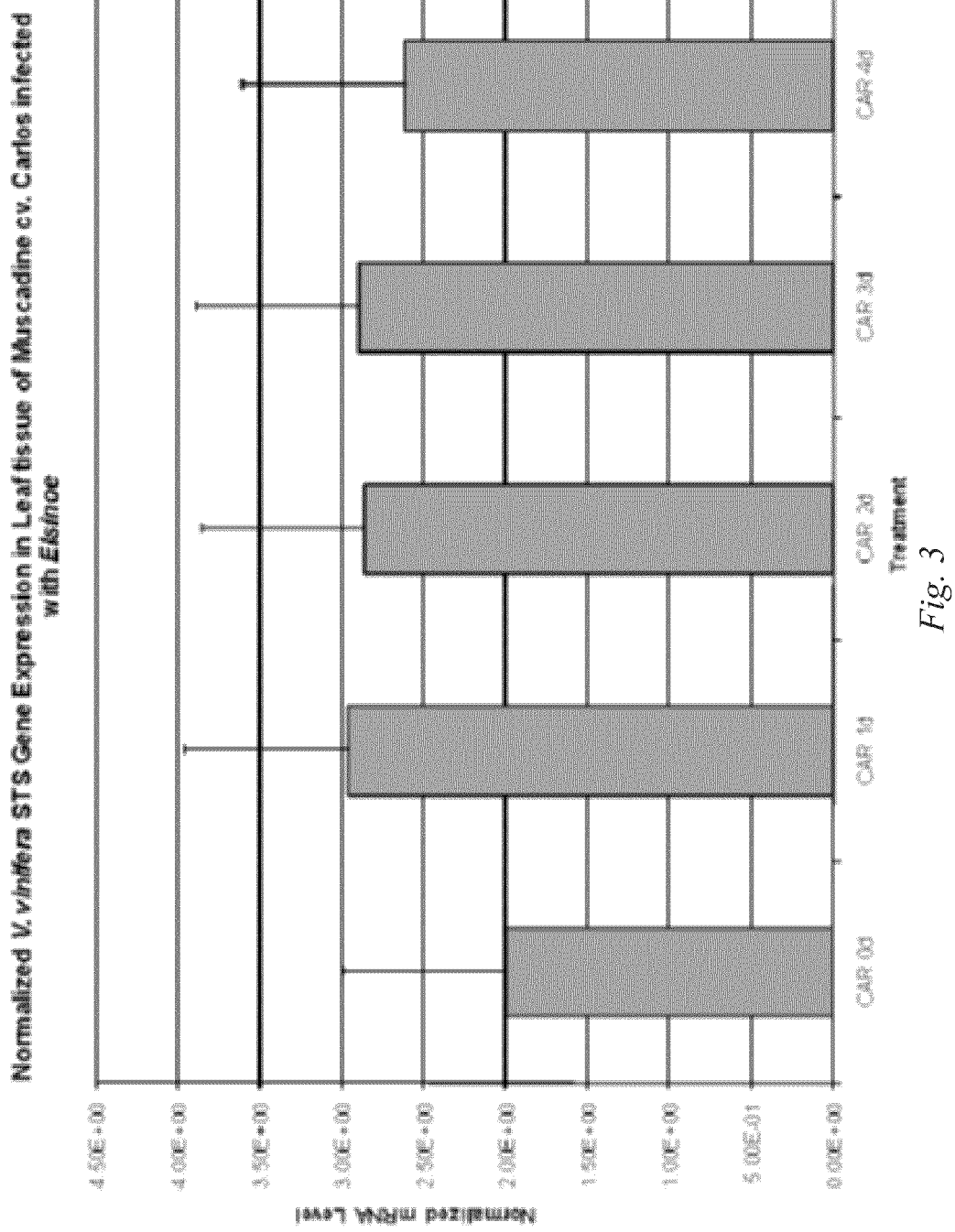
FIG. 3 is a bar graph illustrating the relative expression level of stilbene synthase gene (BS) upon *Elsinoe* infection during different periods (days) of infection in muscadine cultivar cv. Carlos.

In order to study the expression levels of MSB1 and BS gene in anthracnose-infected grape plant, real-time PCR was carried out using MSB1 and BS gene specific primers. Muscadine cv. Carlos was infected with *Elsinoe ampelina*, which causes anthracnose in grape. Leaf samples were collected at regular intervals (0, 1, 2, 3, 4 d after inoculation) and analyzed. Previous studies have shown that it takes 4 to 5 days after infecting with *Elsinoe* to visualize the symptoms. Total RNA was isolated from the leaf tissue following our modified protocol for further studies. The PCR result revealed higher expression of muscadine STS gene compared to *V. vinifera* as the infection advanced, as depicted in FIGS. 2 and 3. This indicates that muscadine STS gene can suppress fungal activity more effectively compared to vinifera STS gene, thereby preventing further disease development in muscadine grapes.

The above analysis revealed that the MSB1 has signal peptides, which can perceive the stress (biotic) and react to it. Thus, muscadine genotypes may have the potential to synthesize sufficient amount of stilbene phytoalexins in response to fungal pathogen attack. The primer combination amplifying stilbene synthase gene can be used as a marker to screen muscadine genotypes for identifying muscadine genotypes expressing higher amount of stilbene synthase.

3. Conclusions

Muscadine are known to contain higher levels of polyphenols that are known to be involved in disease tolerance and possess nutraceutical value. Some of these phenolic compounds are unique to muscadine. Isolation and characterization of STS from muscadine grape revealed six isoforms of stilbene synthase gene, of which four were found to be unique to muscadine.

The expression level of MSB1 gene was found to be higher in anthracnose-tolerant muscadine genotype compared to anthracnose-susceptible bunch following fungal (*Elsinoe ampelina*) infection indicating its effectiveness against fungal disease. In silico analysis revealed that the deduced protein sequence has signal peptide which can perceive stress signals.

4. References

[1] G. Achille, S. Francesca, M. Fulvio, T. Aldo, B. Alma, V. Urska, C. Paolo, B. Roberto, and C. Massimo, Expression of the stilbene synthase (StSy) gene from grapevine in transgenic white poplar results in high accumulation of the antioxidant resveratrol glucosides" Transgenic Research, 2004, Vol. 13, issue 3, pp. 203-214.

[2] H. Arichi, Y. Kimura, H. Okunda, K. Baba, M. Kozawa, and S. Arichi, "Effect of stilbene compounds of the root of Polygonum cuspidatum Sieb. Et Zucc on lipid metabolism", Chemical & Pharmaceutical Bulletin, 1982, Vol. 30, pp. 1766-1770.

[3] H. Bannai, Y. Tamada, O. Maruyama, K. Nakai, and S. Miyano, "Extensive feature detection of N-terminal protein sorting signal", Bioinformatics, Vol 18, pp. 298-305.

[4] N. Blom, S. Gammeltoft, and S. Brunak, "Sequence and structure based prediction of eukaryotic protein phosphorylation sites", Journal of Molecular Biology, 1999, Vol 294 pp. 1351-1362.

[5] O. Emanuelsson, H. Nielsen, and G. von Heijne, "ChloroP, a neural network-based method for predicting chloroplast transit peptides and their cleavage sites", Protein Science, 1999, Vol. 8, pp. 978-984.

[6] F. Fronttin, A. Martinez, P. Peynot, S. Mitra, R. C. Holz, C. Giglione, and T. Meinnel, "The proteomics of Nterminal methionine cleavare", Molecular and Cellular Proteomics, 2006, Vol. 5, pp. 2336-49.

[7] R. Hain, H. J. Reif, E. Krause, R. Langebartels, H. Kindle, B. Vornam, W. Wiese, E. Schmelzer, P. H. Schreier, R. H. Stocker, and K. Stenzel, "Disease resistance results from foreign phytoalexin expression in a novel plant", Nature, 1993, Vol. 361, pp. 153-156.

[8] Y. Kimura, H. Okunda, and S. Arichi, "Effects of stilbene on arachidonate metabolism in leukocytes", Biochimica et Biophysica, 1985, Vol. 834, pp. 275-278.

[9] D. W. Lee, S. Lee, G. Lee, K. H. Lee, S. Kim, G. W. Cheong, and I. Hwang, "Functional Characterization of Sequence Motifs in the Transit Peptide of *Arabidopsis* Small Subunit of Rubisco", Plant Physiology, 2006, Vol. 140, issue 2, pp. 466-483.

[10] L. M. Lois, C. D. Lima, and N. H. Chua, "Small ubiquitin-like modifier modulates abscisic acid signaling in *Arabidopsis*", Plant Cell, 2003, Vol. 15, pp. 1347-1359.

[11] M. N. Musingo, C. A. Sims, R. P. Bafes, S. F. Okeefe, and O. Lamikanra, "Changes in ellagic acid and other phenols in muscadine grape (*Vitis rotundifolia*) juices and wines during storage", American Journal of Enology and Viticulture, 2001, Vol. 52, issue 2, pp. 109-115.

[12] H. Ville, A. Julius, A. B. Henri, F. Mitsuaki, J. P. Jorma, N. Akira, and S. Lea, "PDSM, a motif for phosphorylation-dependent SUMO modification" PNAS, USA, 2006, Vol. 103, pp. 45-50.

[13] X. Yu, Z. Fengfeng, F. Chuanhai, X. Ying, and Y. Xuebiao, "SUMOsp: a web server for sumoylation site prediction", Nucleic Acids Research, 2006, Vol. 34, pp. 254-257.

[14] Y. J. Zhu, R. Agbayani, C. S. Tang, and P. H. Moore, "Developing transgenic papaya to improve broad disease resistance against fungal pathogens", [abstract] Proc 3rd International Symposium on Tropical and Subtropical Fruits, 2004, pp. 48.

Vasanthaiah H K N, Katam R and Basha S M. 2007. A New Stilbene Synthase gene from Muscadine (*Vitis rotundifolia*) Grape Berry. Proceedings of the Frontiers in the Convergence of Bioscience and Information Technologies (FBIT), pp. 87-91.

Katam R, Vasanthaiah H K N and Basha S M. 2007. Protemoic Approach to Screen Peanut Genotypes with Enhanced Nutritional Qualities. Proceedings of the 2007 Frontiers in the Convergence of Bioscience and Information Technologies (FBIT), pp. 171-178.

Vasanthaiah H K N, Ramesh Katam, and Basha S M (2008). Efficient protocol for isolation of functional RNA from different grape tissue rich in polyphenols and polysaccharides for gene expression studies. Electronic J. Biotechnology. 11(3).

II. Identification and Characterization of PD-Tolerance Related Proteins in Muscadine Grape Xylem Sap Pierce's disease (PD) is a destructive bacterial disease of grapes caused by *Xylella fastidiosa*, which is xylem-confined. The tolerance level to this disease varies among *Vitis* species. An embodiment of the current invention identifies unique xylem sap proteins present in PD-tolerant Florida hybrid bunch and Muscadine grape. The study showed wide variation in their xylem sap protein composition, where a set of polypeptides with pI between about 4.5 and about 4.7 and Mr of about 31 kDa were present in abundant amount in muscadine, in reduced levels in Florida hybrid bunch (*Vitis* spp., PD-tolerant), and absent in bunch grapes (*V. vinifera*, PD-susceptible).

Liquid chromatography, mass spectrometry, and mass spectrometry analysis of these proteins revealed their similarity to β-1, 3-glucanase (SEQ ID NO:7), peroxidase (SEQ ID NO:8), and a subunit of Oxygen-Evolving Enhancer Protein 1 (SEQ ID NO:9), which are known to play a role in defense and oxygen generation. Enhancement of oxygen production by the Oxygen-Evolving Enhancer Protein 1 appears to discourage *Xylella* colonization of xylem sap in these genotypes. This makes these genotypes resist bacterial growth, whereas lack of these proteins in PD-susceptible genotypes enhances *Xylella* colonization of these genotypes.

In addition, the amount of free amino acids and soluble sugars was found to be significantly lower in xylem sap of muscadine genotypes compared to *V. vinifera* genotypes, indicating that the higher nutritional value of bunch grape sap may be more suitable for *Xylella* growth. These data suggest that the presence of these unique proteins in xylem sap is vital for PD tolerance in muscadine and Florida hybrid bunch grapes.

EXAMPLE

1. Materials and Methods a. Plant Material

The PD-tolerant grapevines belonging to the *V. rotundifolia* (cvs. Dixieland, Cowart, Noble, Alachua, African Queen, Black Beauty, Scuppernong, Pride. Regale, Higgins, Scarlet, Sweet Jenny, Senoia, Carlos, and Sterling) and Florida hybrid bunch (cvs. Lake Emerald, Blue Lake, and Orlando Seedless) grape genotypes grown at the vineyard of Center for Viticulture and Small Fruit Research, Florida Agricultural and Manufacturing University, Tallahassee, Fla., USA were used in this study. Highly PD-susceptible *V. vinifera* genotypes (cvs. Barbara, Ruby Cabernet, Sauvignon Blanc, Chenin Blanc, Fiesta, Napa Gammy, Zinfandel, Petite Sarah, Merlot, Pinot Noir, Flame Seedless, JS2605, and Chardonnay) were grown in a screened cage to protect them from insects (Glossy Wing sharp shooters) that spread Pierce's disease and were used as "healthy" control plants. These grape plants were obtained from Sonoma Grapevines, Inc, Santa Rosa, Calif., USA.

b. Xylem Sap Collection

Phloem tissue from selected stem (spring growth) portions was peeled off using a sharp blade (to avoid contamination from phloem proteins), and sap from the peeled stem portion was collected by cutting the stem using a sharp clipper. The cut stem was thoroughly washed with water before collecting sap to avoid any possible contamination from phloem sap and other cellular compartments. Since *Xylella* multiplication is known to be high during the spring season, xylem sap was collected on alternative days for three (3) days in the spring of 2007. Recovery of sap was found to be higher during early morning hours; therefore, sap collections were made during these hours. The sap was collected into sterile 50 ml Falcon tubes covered with parafilm to prevent contamination. The collected sap was brought to the laboratory on ice, divided into 20 ml aliquots, and freeze-dried. The dried material was reconstituted in rehydration buffer [8 M urea, 2% 3-[(3-cholamidopropyl)-dimethylammonio]-1-propane sulfonate, 50 mM dithiothreitol (DTT), and 2% ampholines (pH 3.0 to 10)] and used for two-dimensional polyacrylamide gel electrophoresis (2-D PAGE).

c. Confirmation of *X. fastidiosa* Infestation

In order to confirm the presence of *Xylella* in xylem sap, one-dimensional PAGE was performed following the procedure described by Vasanthaiah et al. [18]. Equal amounts of freeze-dried xylem sap, *Xylella*, and blank PD3 broth used to grow *Xylella* were separated on the gel. Electrophoresis was carried out at a constant current of 30 mA, and the samples were silver-stained for visualization as described below.

d. α-Amino Nitrogen and Soluble Sugars Analysis

An aliquot (100 ml) of the xylem sap was used for free amino acids and soluble sugars analysis to determine quantitative differences among *Vitis* species. α-Amino nitrogen analysis of xylem sap was carried out according to the procedure of Yemm and Cocking [19] and sugar content was determined using the method of Yemm and Willis [20].

e. Two-Dimensional Polyacrylamide Gel Electrophoresis

The 2-D PAGE was performed on immobilized pH gradient (IPG) strips (pH 3 to pH 10) on a BioRad Protean Cell following the manufacturer's instructions (BioRad Laboratories, Inc. Hercules, Calif., USA). The freeze-dried xylem sap collected over different days (1, 3, and 5 days) were dissolved in rehydration buffer, and the IGP strips were soaked in this protein solution for 18 h and subjected to isoelectric focusing (IEF) for a total of 20,000 V h. After IEF, the IPG strips were equilibrated for 10 min in equilibration buffer I [6 M urea, 0.375 M Tris-HCl, pH 8.8, 2% sodium dodecyl sulfate (SDS), 20% glycerol, 2% (w/v) DTT]. The IPG strips were then re-equilibrated with equilibration buffer II for another 10 min [6 M urea, 0.375 M Tris-HCl, pH 8.8, 2% SDS, 20% glycerol, 2.5% (w/v) iodoacetamide] and subjected to SDS-PAGE in the second dimension on 8% to 16% criterion gradient Tris-HCl pre-cast gels (BioRad Laboratories, Inc.).

f. Silver Staining

The protein bands were visualized by silver staining following the method of Sambrook et al. [21]. Following electrophoresis, the gels were fixed in acetic acid, methanol, and formaldehyde (50%:49.4%:0.6% v/v/v) for 45 to 60 min. The gels were then washed with methanol (50% v/v) for 15 min followed by distilled water. The gels were incubated in silver nitrite (0.15% w/v) for 30 to 45 min followed by washing with distilled water. The gels were then developed in 0.04% formaldehyde in 2% (w/v) sodium carbonate. The reaction was stopped after the desired intensity of the bands was obtained with 5% (v/v) acetic acid.

g. Mass Spectrometry, Database Searches, and Sequence Analysis

Xylem sap proteins unique to PD-tolerant muscadine genotypes were identified by comparing the 2-D PAGE profiles of the three *Vitis* species. Based on this comparison, ten (10) protein spots that are unique to PD-tolerant *Vitis* species were selected for amino acid sequencing. Two polypeptide spots, B and C from box 1 (indicated by vertical arrows); seven spots, G, H, J, L, O, P, and Q from box 2; and one spot, C from box 3 (FIG. 5), were selected for sequencing. These proteins spots were selected because they were found to be unique among the PD-tolerant *Vitis* species used in the study.

The protein spots were excised with a clean razor blade, destained, dehydrated, and subjected to trypsin digestion. Capillary RP-HPLC separation of protein digests (desalted with a PepMap C18 cartridge) was performed using a PepMap C18 column (15 cm×75 μm i.d.) and Ultimate Capillary HPLC System (LC Packings, San Francisco, Calif., USA). A linear gradient of 5% to 40% (v/v) acetonitrile for 25 min at 200 nl min-1 was used for separation. Tandem mass spectrometric analysis was performed online using a hybrid quadrupole time-of-flight instrument (QSTAR XL hybrid liquid chromatography/mass spectrometry/mass spectrometry (LC/MS/MS) equipped with a nano-electrospray source (Applied Biosystems, Foster City, Calif., USA) and operated with the Analyst QS v1.1 data acquisition software. Tandem mass spectra were extracted by ABI Analyst version 1.1. All MS/MS samples were analyzed using Mascot (Matrix Science, London, UK; version 2.0.01). Mascot was searched with a fragment ion mass tolerance of 0.30 Da and a parent ion tolerance of 0.30 Da. Iodoacetamide derivative of cysteine is specified in Mascot as a fixed modification. Deamidation of asparagine and glutamine and oxidation of methionine were specified in Mascot as variable modifications.

2. Results and Discussion

As with xylem sap of other crops, the xylem sap of *Vitis* species contains low concentration of protein which can make studying xylem sap proteins challenging. In addition, the presence of various compounds such as phenolics, organic acids, amino acids, sugars, and other metabolites can make analysis and characterization of grape xylem sap proteins tedious and difficult. Xylem sap was collected in spring, during which the incidence, multiplication, and movement of *X. fastidiosa* has been reported to be high [22]. Sap collection during morning hours yielded sufficient amount for use in this study. The cut stem was thoroughly rinsed with distilled water before collecting the sap. It has been demonstrated that washing cut stem with water prior to xylem sap collection prevents possible contamination of phloem sap and other adjacent cellular compartments in the sample [15]. Sap was collected from the PD-infected plants, as well as from the control (healthy) plants grown in a screen house (disease-free environment). PD incidence was constantly monitored during the study period to insure plant health. One-dimensional electrophoretic analysis of freeze-dried xylem sap from *V. rotundifolia* (muscadine cv. Dixie Red), *Xylella*, and the blank PD3 broth used to grow *Xylella* showed the presence of a few common protein bands between xylem sap and *Xylella*, indicating the presence of the bacterium in sap (FIG. 4). The presence of these proteins in xylem sap can serve as an indicator of plant health and disease status.

Free amino acids and sugar analysis of xylem sap confirmed the existence of a major difference among the *Vitis* species studied. The amount of free amino acids and soluble sugars was higher in PD-susceptible bunch grape (*V. vinifera*) genotypes compared to PD-tolerant muscadine (*V. rotundifolia*) grape genotypes (FIGS. 5 and 6). This suggests that the xylem sap of bunch grape is more nutritious than muscadine grapes, which may support *Xylella* growth better in PD-susceptible bunch grape than in PD-tolerant muscadine.

For further differentiation, a high throughput two-dimensional gel electrophoresis coupled with silver staining was used to resolve and detect the xylem sap proteins from PD-tolerant *V. rotundifolia* (cv. Dixieland, Cowart, and Sterling) and Florida hybrid bunch (Lake Emerald, Blue Lake, and Orlando Seedless), and PD-susceptible *V. vinifera* (cv. Fiesta, Petite Sarah, and Pinot Noir) genotypes. The *V. vinifera* cultivars were grown under protective environment to prevent infection and were used as "healthy" controls for comparison with muscadine, as the *V. vinifera* cultivars are highly susceptible to PD. The incidence of PD and the activity of the glassy-wing sharpshooter (the vector that carries *Xylella*) are known to be high in southeastern USA. Two-dimensional gel electrophoretic analysis of xylem sap collected on different days during the spring season yielded consistent reproducible polypeptide spots, but their expression levels varied. Since xylem sap protein profiles of grape cultivars within each species were found to be similar, only one profile representing muscadine (cv. Dixieland), Florida hybrid bunch (cv. Lake Emerald), and bunch (cv. Fiesta) are discussed herein to avoid duplication.

Figure 7A:
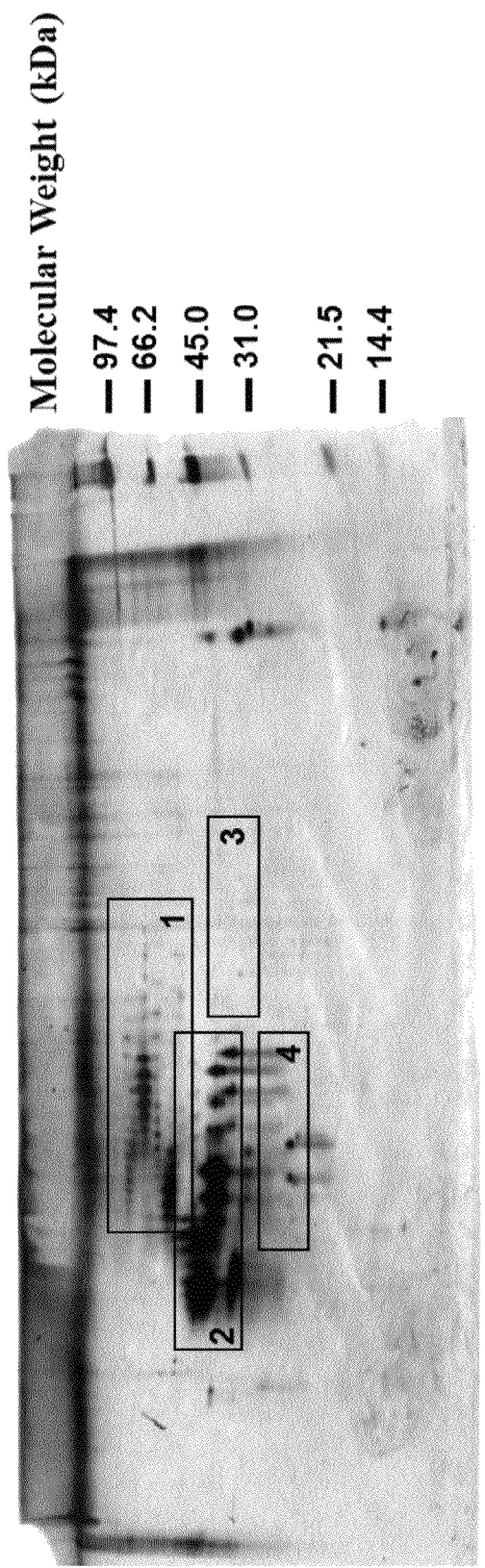
FIGS. 7A-7C depict a two-dimensional polyacrylamide gel electrophoretic (2-D PAGE) profile of xylem sap proteins.
Figure 7B:
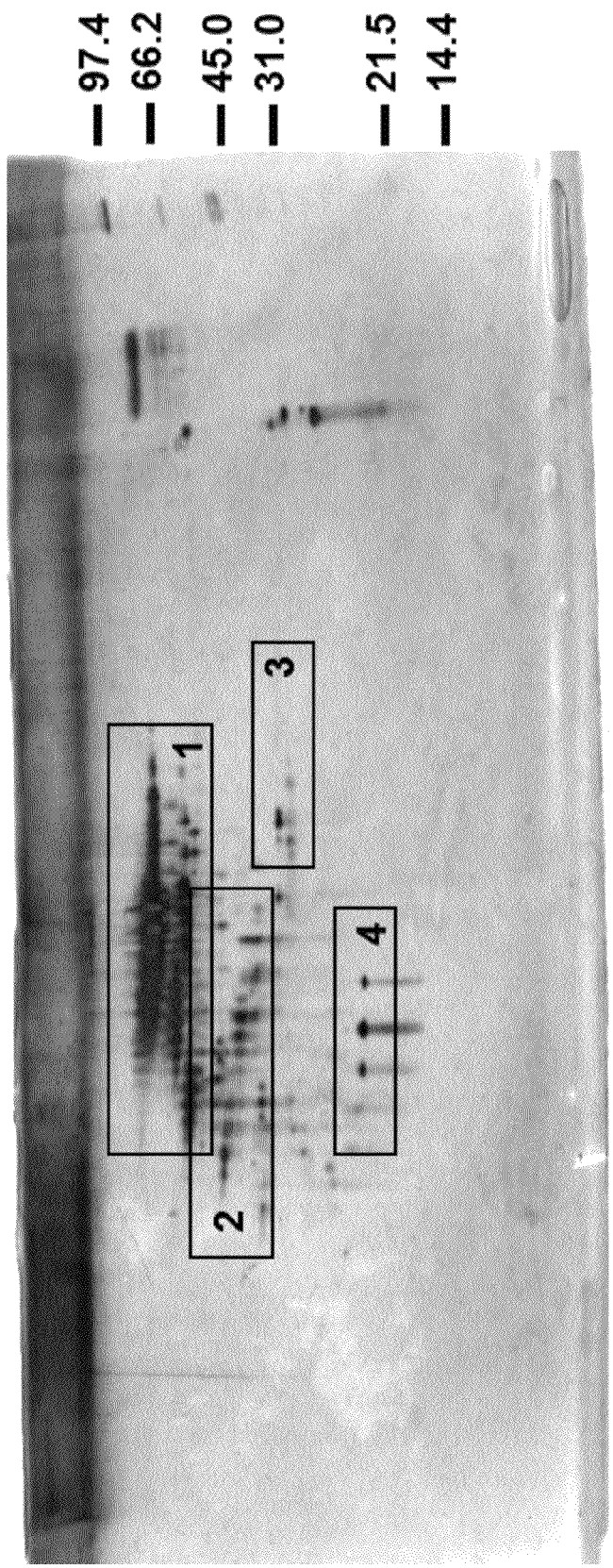
Figure 7C:
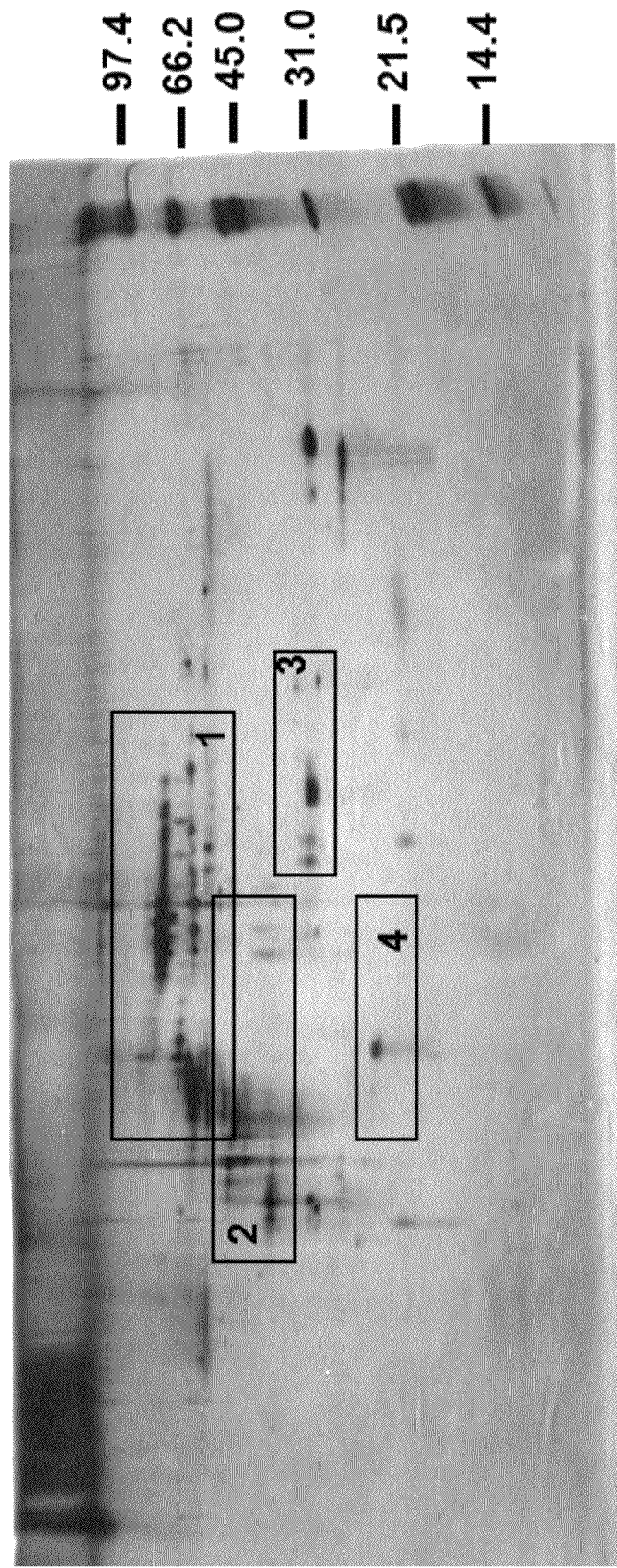

The 2-D PAGE system separated xylem sap proteins into more than 100 polypeptides with pIs between 3.5 to 9.0 and molecular weight of (Mr) 20 to 75 kDa (FIG. 7). The majority of the xylem sap proteins appear to be of high (>40 kDa) molecular weight, and they resolved into clusters of multiple spots. The apparent Mr of proteins in each cluster was similar, but their pIs were slightly different resulting in a series of spots. Most of these clusters focused between pH 4.0 and 7.0 and had Mr of >40 kDa. Such polypeptide clusters have been observed on 2-D PAGE of several seed, leaf, and microbial protein extracts, and appear to be a normal occurrence in plant tissue [23-25]. However, the polypeptide profiles of xylem sap within the clusters of different *Vitis* species were found to be distinct and unique (FIG. 7). Polypeptides unique to each genotype were identified by comparing their 2-D PAGE profiles with each other. Comparison of 2-D gels was carried out both manually and by using PD Quest software (PD Quest 2-D Analysis Software, BioRad Laboratories, Inc.).

This comparison identified four (4) regions of the gel with distinct polypeptide composition. A close-up view of these regions (box 1 through box 4) showing major differences among the different *Vitis* species is shown in FIGS. 8A-D. The three *Vitis* species showed major differences in the polypeptides with Mr range between 55 and 75 kDa and pI between 5.0 and 7.0 [FIG. 8A (box 1 in FIG. 7)]. As discussed previously, these polypeptides resolved as clusters, and their number and quantity varied among the *Vitis* species. For case of comparison, these polypeptide clusters are identified as cluster A, cluster B, cluster C, cluster D, and cluster E based on their mobility (Mr).

In the muscadine grape cultivar, all the polypeptides of cluster B and cluster E were present while the polypeptides of cluster D were absent. In the Florida hybrid bunch grape cultivar, polypeptides of all five clusters (A through E) were present in higher amounts. In bunch grape cultivar, polypeptides of cluster B, cluster C, cluster D, and cluster E were present, but the cluster A proteins were absent. A comparison of the *V. rotundifolia* and *V. vinifera* cultivars show that *V. vinifera* lacked cluster A polypeptides while *V. rotundifolia* lacked cluster D polypeptides. Likewise, a comparison of the muscadine and the Florida hybrid bunch grape cultivars showed that both contained cluster A, cluster B, cluster C, and cluster E polypeptides, but the muscadine grape cultivar lacked the cluster D polypeptides.

Figure 4:
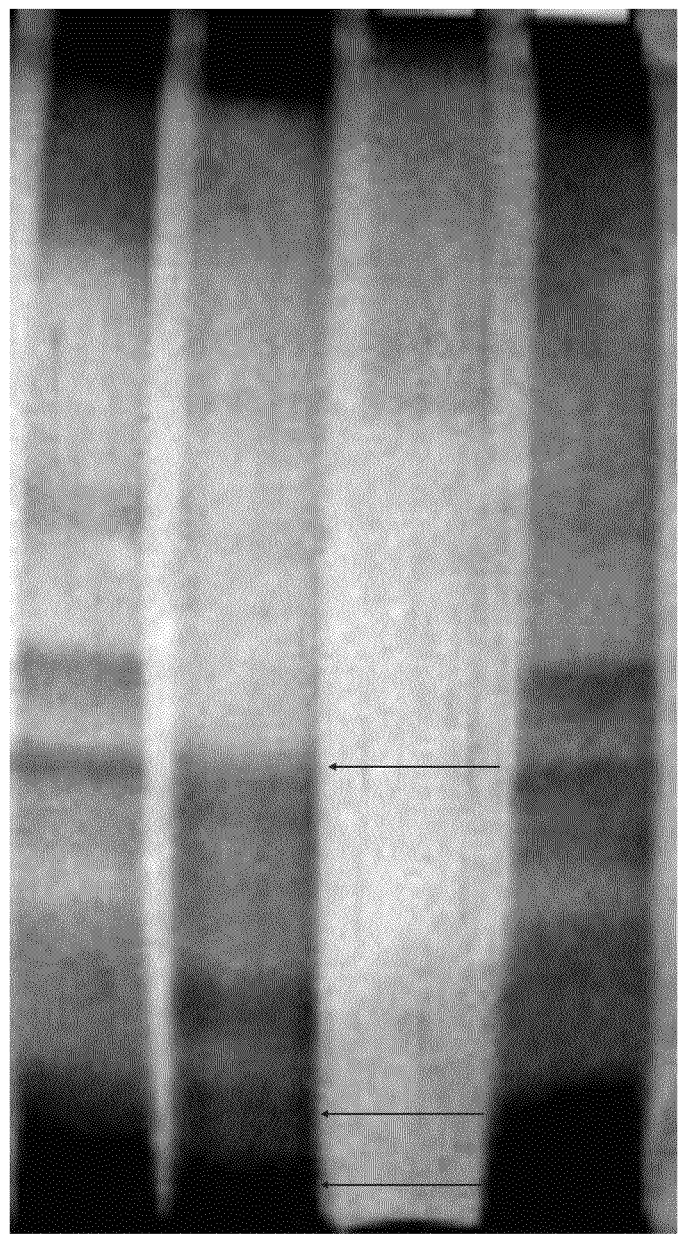
FIG. 4 depicts similarity in the polypeptide composition of xylem sap of muscadine cv. Dixie Land and *Xylella*. Lanes 1 and 4: Xylem sap of Dixie Land (Muscadine), Lanes 2: *Xylella* and Lane 3: Blank PD3 broth. Arrows indicate common polypeptides.
Figure 5:
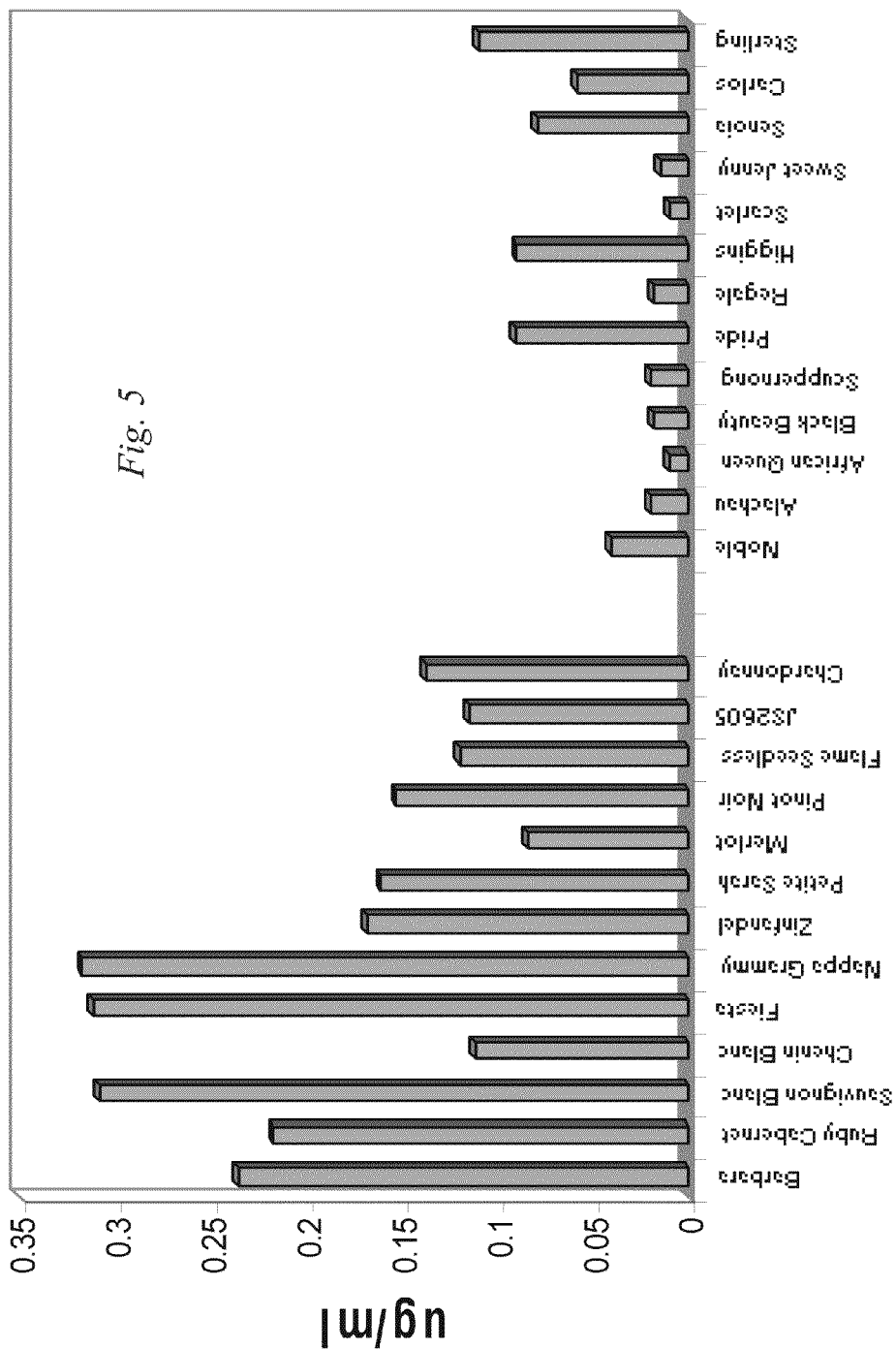
FIG. 5 is a graphical illustration showing variation in the xylem sap free amino acids content in grape cultivars. *V. vinifera* 1-13=Barbara, Ruby Cabernet, Sauvignon Blanc, Chenin Blanc, Fiesta, Napa Gammy, Zinfandel, Petite Sarah, Merlot, Pinot Noir, Flame Seedless, JS2605, and Chardonnay; *V. rotundifolia* 1-13=Noble, Alachua, African Queen, Black Beauty, Scuppernong, Pride, Regale, Higgins, Scarlet, Sweet Jenny, Senoia, Carlos, and Sterling.
Figure 6:
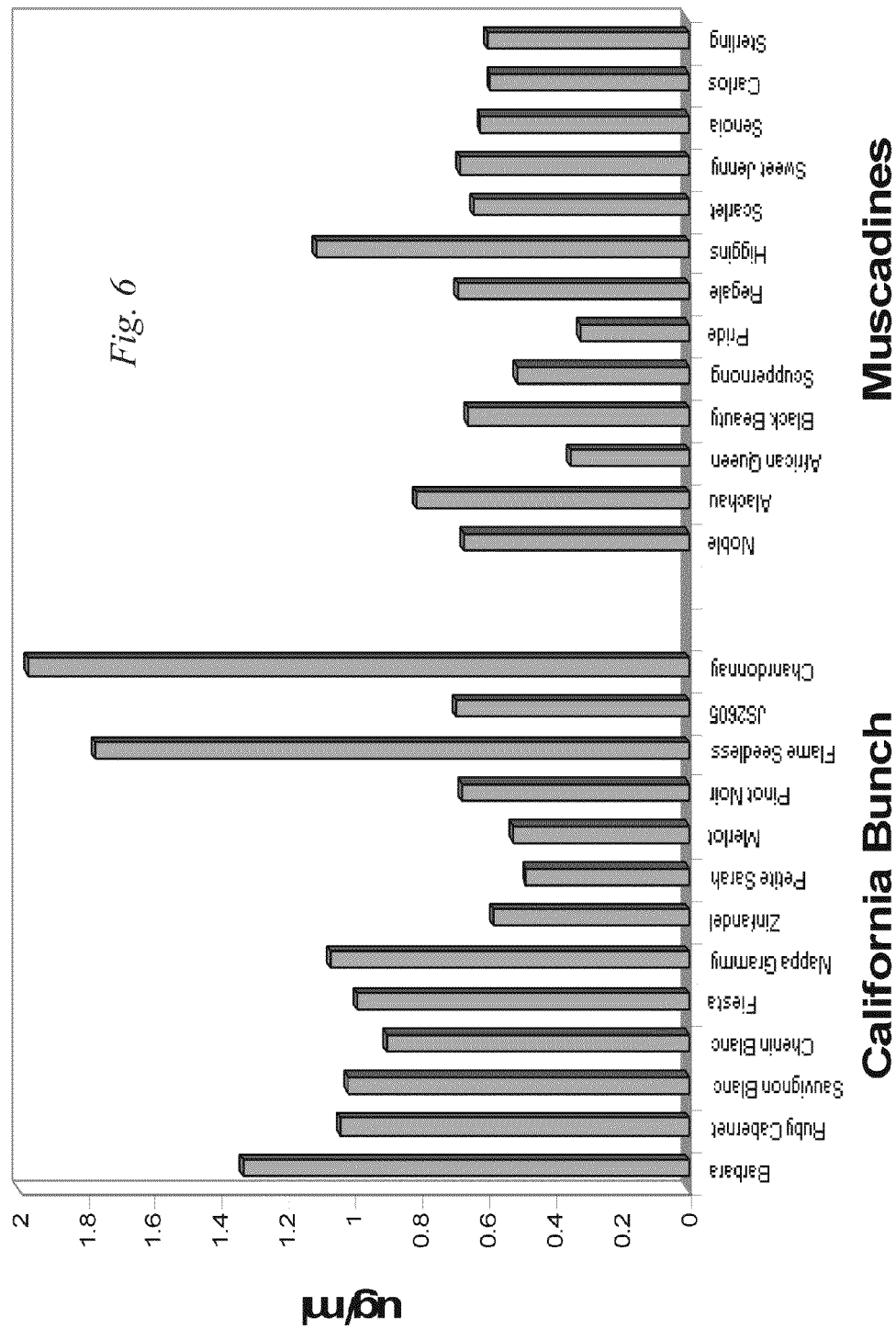
FIG. 6 is a graphical illustration showing variation in the xylem sap-soluble sugars content in grape cultivars. *V. vinifera* 1-13=Barbara, Ruby Cabernet, Sauvignon Blanc, Chenin Blanc, Fiesta, Napa Gammy, Zinfandel, Petite Sarah, Merlot, Pinot Noir, Flame Seedless, JS2605, and Chardonnay; *V. rotundifolia* 1-13=Noble, Alachua, African Queen, Black Beauty, Scuppernong, Pride, Regale, Higgins, Scarlet, Sweet Jenny, Senoia, Carlos, and Sterling.
Figure 8A:
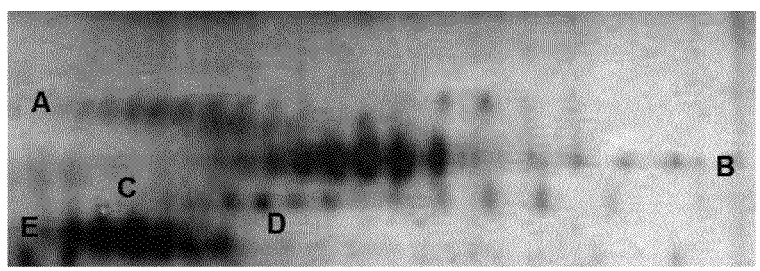
FIG. 8A is an enlarged view of Box 1 from FIG. 4. In Box 1, polypeptide clusters are identified as cluster A, B, C, D, and E.
Figure 8A:
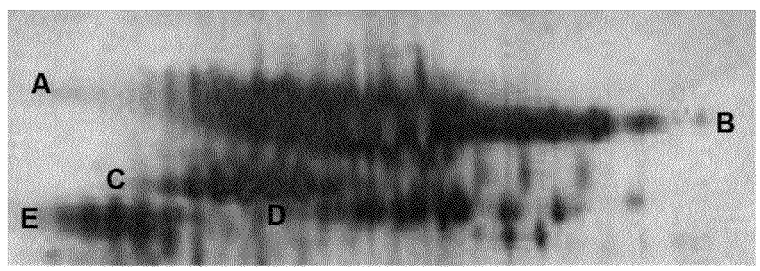
Figure 8A:
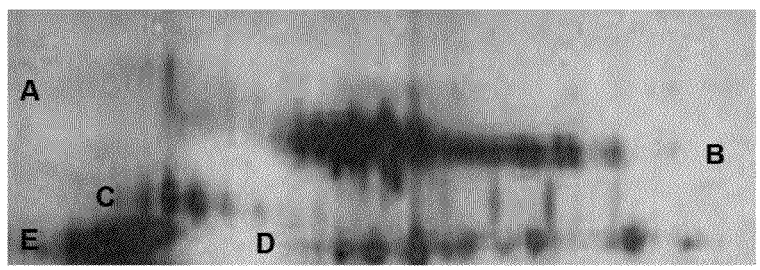
Figure 8B:
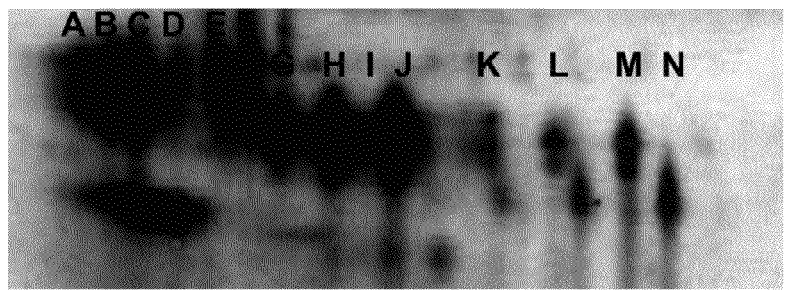
FIG. 8B is an enlarged view of Box 2 from FIG. 4.
Figure 8B:
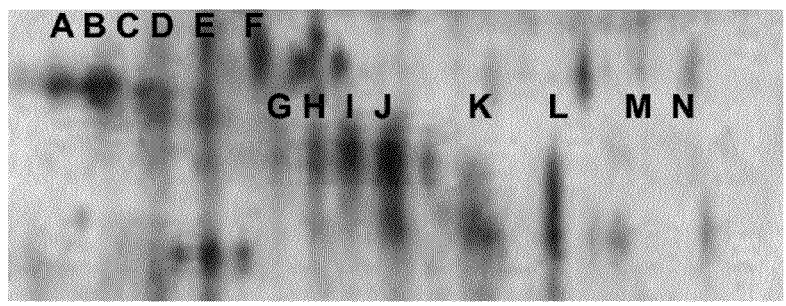
Figure 8B:

FIG. 8B shows the gel region containing proteins with pIs between 4.1 and 6.5 and apparent Mr around 35 to 55 kDa (box 2 in FIG. 4). This region is considered important since it contains the polypeptides unique to the PD-tolerant muscadine and Florida hybrid bunch grape cultivars. These polypeptides were seen to be completely absent in the PD-susceptible *V. vinifera* cultivars. As seen in FIG. 8B, the muscadine grape (cv. Dixieland) contained more than 14 polypeptides (A through N) in this region, while the Florida hybrid bunch grape (cv. Lake Emerald) contained polypeptides A, B, D, E, G, H, I, J, and L at reduced levels and lacked polypeptides C, F, K, M, and N. In the bunch grape cultivar (*V. vinifera* cv. Fiesta), polypeptides G, H, I, J, K, L, M, and N were completely absent while the other polypeptides were present at significantly reduced levels. These data show that the expression of polypeptides G, H, I, J, K, L, M, and N was high in muscadine [cv. Dixieland (PD-tolerant)], low in Florida hybrid bunch grape [cv. Lake Emerald (PD-tolerant)], and absent in bunch grape [cv. Fiesta (PD-susceptible)].

Figure 8C:
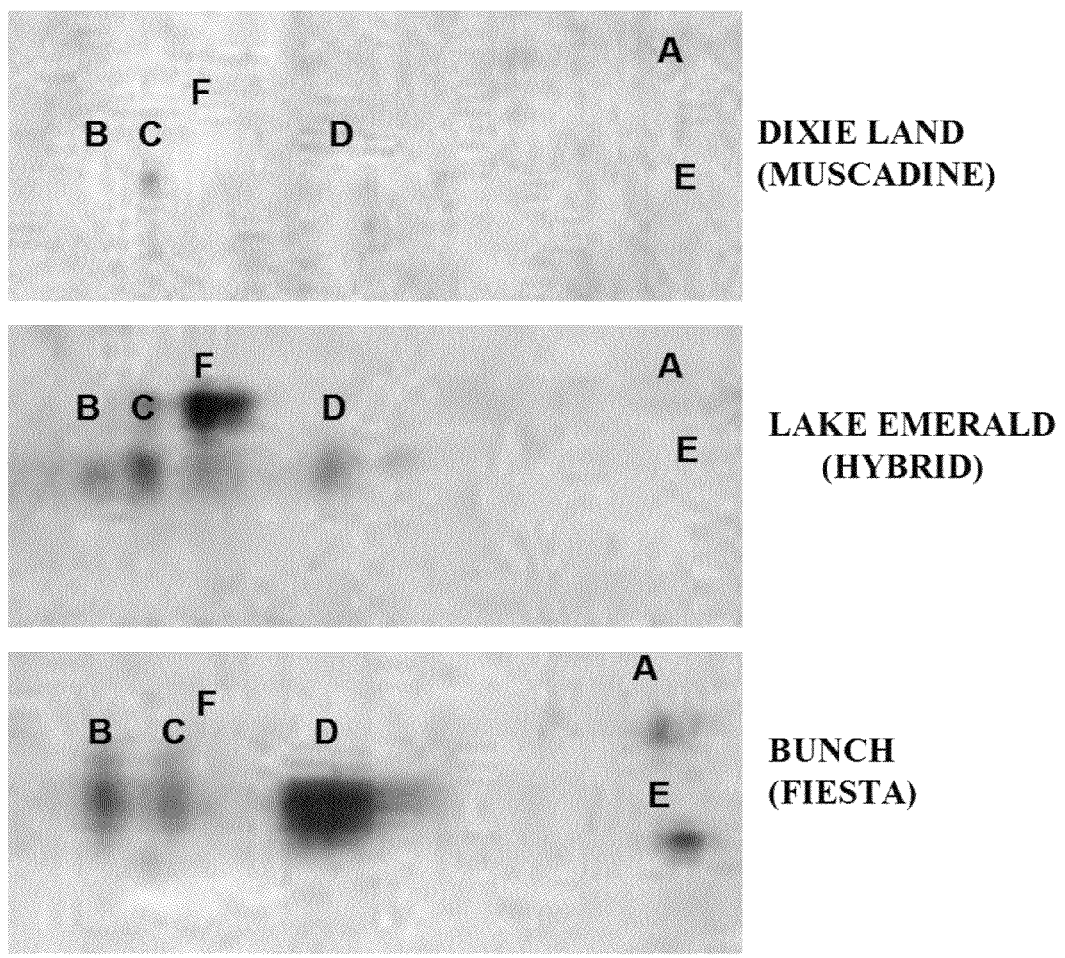
FIG. 8C is an enlarged view of Box 3 from FIG. 4.
Figure 8D:
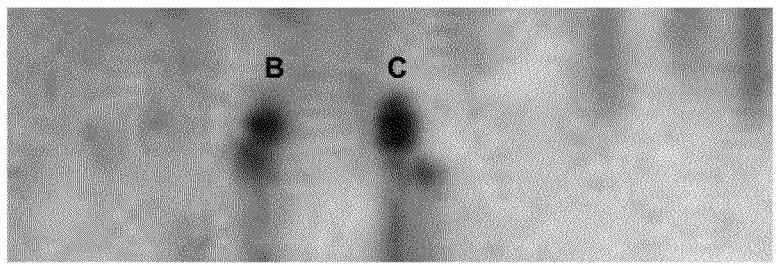
FIG. 8D is an enlarged view of Box 4 from FIG. 4.
Figure 8D:
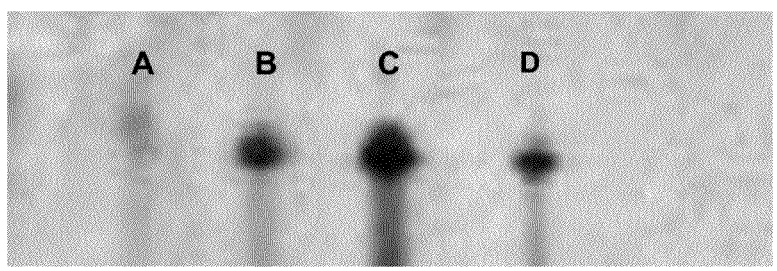
Figure 8D:
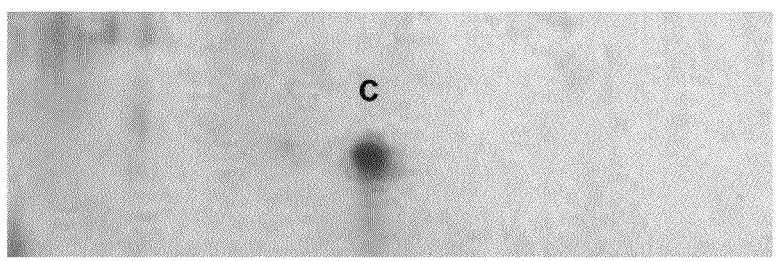

In addition, FIG. 8C showing gel region (box 3 in FIG. 7) also depicts differences in polypeptide composition among the *Vitis* species. In this region, the bunch grape (cv. Fiesta) contained five polypeptides (A through E) but lacked polypeptide F, while the Florida hybrid bunch (cv. Lake Emerald) contained reduced levels of polypeptides B, C, and D and a unique polypeptide F but lacked polypeptides A and E. None of these polypeptides (A through F) were found in *V. rotundifolia* (cv. Dixieland). Furthermore, the polypeptides identified in box 4 (FIG. 7) also varied among the *Vitis* species. Florida hybrid bunch grape contained four polypeptides (A, B, C, and D) in this region, muscadine grape had two polypeptides (B and C), and bunch grape had only one polypeptide C. These data further suggest that although xylem sap of *Vitis* species contains certain common proteins, differences occur in the expression of certain unique polypeptides.

The polypeptide data including their pI and Mr found in different *Vitis* species are summarized in Table 1.

TABLE 1

Characteristics of xylem sap polypeptides from different *Vitis* species.

| Polypeptide | | | *Vitis* species | | |
| --- | --- | --- | --- | --- | --- |
| Group | pI (pH) | M$_r$ (kDa) | *V. rotundifolia* | *Vitis* spp. | *V. vinifera* |
| Common Polypeptides: | | | | | |
| Box 1 | | | | | |
| B | 5.0-6.5 | 66 | + | + | + |
| C | 5.0-6.5 | 66 | + | + | + |
| E | 4.5-5.0 | 50 | + | + | + |
| Box 2 | | | | | |
| A | 4.2 | 45 | + | + | + |
| B | 4.4 | 45 | + | + | + |
| D | 4.5 | 45 | + | + | + |
| E | 4.6 | 45 | + | + | + |
| F | 4.8 | 45 | + | + | + |
| Box 3 | | | | | |
| C | 6.3 | 31 | + | + | + |
| Box 4 | | | | | |
| C | 5.6 | 23 | + | + | + |
| Variable Polypeptides: | | | | | |
| Box 1 | | | | | |
| A | 4.5-5.0 | 70 | + | − | − |
| D | 6.0-7.0 | 50 | + | − | + |
| Box 2 | | | | | |
| C | 4.3 | 45 | + | − | − |
| G | 5.0 | 31 | + | + | − |
| H | 5.2 | 31 | + | + | − |
| I | 5.3 | 31 | + | + | − |
| J | 5.5 | 31 | + | + | − |
| K | 5.8 | 25 | + | − | − |
| L | 6.0 | 25 | + | + | − |
| M | 6.2 | 25 | + | + | − |
| N | 6.3 | 25 | + | − | − |
| Box 3 | | | | | |
| A | 7.0 | 35 | − | − | + |
| B | 6.2 | 31 | − | + | + |
| D | 6.5 | 31 | − | + | + |

TABLE 1-continued

Characteristics of xylem sap polypeptides from different *Vitis* species.

| Polypeptide | | | Vitis species | | |
|---|---|---|---|---|---|
| Group | pI (pH) | M$_r$ (kDa) | V. rotundifolia | Vitis spp. | V. vinifera |
| E | 7.2 | 28 | − | − | + |
| F | 6.5 | 45 | − | + | − |
| Box 4 | | | | | |
| A | 5.2 | 23 | − | + | − |
| B | 5.4 | 23 | + | + | − |
| D | 6.0 | 23 | − | + | − |

"+" indicates presence; "−" indicates absence; "M$_r$" indicates molecular weight; and "pI" indicates isoelectric point.

The polypeptides present in all the three species are termed as "common" while the polypeptides that differed among the species are termed "variable". Of more than 100 polypeptides observed in the xylem sap 2-D PAGE profiles of *Vitis* species, only a few polypeptides were found to be common to all the three species. The remaining polypeptides were either absent or were present in variable amounts among the *Vitis* species, thus indicating the existence of wide genetic differences in xylem sap protein composition.

Based on comparisons of Muscadine, Fla. hybrid bunch and European grapes, xylem sap 2-D PAGE profiles, ten (10) polypeptides showing major differences were selected for sequencing by LC/MS/MS. Partial amino acid sequencing data showed that polypeptide spots L and P (FIG. 8B) were found to be similar to β-1, 3-glucanase and peroxidase, both of which are known to be involved in plant defense (Table 2), whereas spots G, H, and J (FIG. 8B) were found to be similar to oxygen-evolving enhancer protein (OEE1), which is involved in generating oxygen.

Florida hybrid bunch and *V. vinifera* grapes may be responsible for their superior PD-tolerance characteristics than the hybrids and bunch.

β-1, 3-glucanases are a class of proteins that are often associated with pathogen-related proteins and are believed to mediate defense responses upon pathogen infection [26]. The occurrence of β-1, 3-glucanase proteins has been reported only in tomato xylem sap [7, 11]. Interestingly, glucanases have been suggested to act in a synergistic manner with thaumatin-like proteins that can bind to β-1, 3-glucanases [27] and have not been reported to occur in xylem sap of healthy, unchallenged plants, but were found only after infection [11]. Although the plants studied were not actively challenged with *Xylella*, the expression of β-1, 3-glucanase protein indicates that the field-grown PD-tolerant muscadine and Florida hybrid bunch grape were naturally infected with *Xylella*.

Another class of pathogen-related proteins induced upon *Xylella* infection in PD-tolerant *Vitis* species is peroxidase (spot #P), which is an oxidative enzyme [28]. This class III secretory peroxidase is known to perform versatile functions along with regulation of $H_2O_2$ level and oxidation of toxic compounds upon pathogen infection [29]. The induction of a cationic peroxidase in xylem vessels has been reported in an incompatible interaction between the vascular pathogen *Xanthomonas oryzae* cv. oryzae and rice [30]. In the compatible response, the antibodies did not detect the presence of peroxidase until 48 h after infection. This suggests that the expression of peroxidase in xylem sap is due to *Xylella* infection. Expression of xylem sap peroxidase has also been reported in apple, peach, and pear and has been suggested to play a role in plugging damaged vascular tissue [7].

The expression of β-1, 3-glucanase and peroxidase in PD-tolerant muscadine and Florida hybrid bunch grape indicates

TABLE 2

Partial sequence of xylem sap proteins from *V. rotundifolia* obtained by mass-spectrometric analysis that showed high similarity (95% identity) to database entries.

| Spot No. | Sequence | SEQ ID NO. | MASCOT Score | No. of unique peptides | GI accession No. | Protein similar to | Organism matched | UniProtKB Acc. No. |
|---|---|---|---|---|---|---|---|---|
| L | NIFNAISAAGLGNQIK | SEQ ID NO: 10 | 88.2 | 2 | CAB91554 | β 1-3 glucunase | V. vinifera | P86102 |
|   | VSTAIDTGVLGTSYPPSK | SEQ ID NO: 11 | 76.4 | | | | | |
| P | DNTAKEKDSPANLSLR | SEQ ID NO: 12 | 66.2 | 4 | 18418208 | Peroxidase | A. thaliana | P86103 |
|   | QAGVEFSDQSLFTSAR | SEQ ID NO: 13 | 90.1 | | | | | |
|   | NTFDNAYYIALQR | SEQ ID NO: 14 | 55.2 | | | | | |
|   | TCAAGDNAEQPLDPSR | SEQ ID NO: 15 | 42.4 | | | | | |
| G | TNAENEFVTI KK | SEQ ID NO: 16 | 54.1 | 1 | P84718 | OEE 1 | P. strobus | P86104 |
| H | TNAENEFVTI KK | SEQ ID NO: 17 | 52.2 | 1 | P84718 | OEE 1 | P. strobus | P86104 |
| J | TNAENEFVTI KK | SEQ ID NO: 18 | 50.6 | 1 | P84718 | OEE 1 | P. strobus | P86104 |

"*" indicates that the spots were excised from Box 2 of FIG. 4.

The occurrence of similar or identical gene products slightly differing in their pI and Mr is a common feature observed in 2-D analysis and can be attributed to post-translational modifications of distinct amino acids of one single gene product. Protein sequence searches of the other five protein spots failed to show any similar matches with the known database and, hence, are identified as proteins of unknown function (data not shown).

The β-1, 3-glucanases (spot #L), peroxidase enzyme (spot #P), and oxygen-evolving enhancer protein (spots #G, H, and J) were expressed only in PD-tolerant *Vitis* species (muscadine and Florida hybrid bunch grape), which may be partly responsible for their PD tolerance. Furthermore, high expression of these proteins by muscadine genotypes compared to that the defense pathways, jasmonic and salicylic acid pathways, were induced upon *Xylella* infection. The accumulation of pathogen-related proteins suggests that the plant has acquired systemic resistance against a broad spectrum of microorganisms, which require salicylic acid and confer long-lasing protection [31, 32].

Additionally, the expression of three unique polypeptides was also found (spots #G, H, and J), which were found identical to OEE1. OEE1 has been suggested to bind with calcium ions, which have been shown to be essential for maximizing the rates of oxygen evolution during photosystem complex II [33]. Further, full-length amino acid sequencing of this unique polypeptide may reveal the differences in the amino acid composition present compared to OEE1. *X. fastidiosa* lacks cytochrome with high oxygen affinity. Instead, it possesses simple and quite unusual aerobic respiratory complex [34]. In silico functional analysis of *Xylella* has shown the presence of the least energy-efficient type of aerobic respiration of any known organism reported to date [34]. They also suggested that *Xylella* clearly prefers anaerobic respiration based on sulfur metabolism. Dalke [35] reported that *Xylella* can breathe with or without oxygen, but both energy pathways are extremely inefficient. This can be utilized as a potential target for disease control.

Expression of OEE1-type polypeptide in xylem sap of PD-tolerant *Vitis* species suggests that it may be involved in generating higher levels of oxygen in sap, hampering normal respiratory process of *Xylella* and thus affecting its growth. This result suggests that the expression of β-1, 3-glucanases, peroxidase enzyme, and oxygen-evolving enhancer protein, along with few unknown proteins, by the PD-tolerant muscadine and Florida hybrid grape may be a vital mechanism for their tolerance to PD.

3. Conclusion

The PD tolerance level of muscadine and Florida hybrid grape was found to vary depending upon their xylem sap composition. The results of the described example revealed the existence of major differences in xylem sap free amino acids, soluble sugars content, and protein composition among *Vitis* species. The higher free amino acids and soluble sugars content in *V. vinifera* clearly suggests *Xylella* preference to this species perhaps because of its suitability for *Xylella* growth. Expression of unique proteins by PD-tolerant muscadine and Florida hybrid bunch grape genotypes upon infection indicates their defense mechanism against *Xyella*. The function of many of these proteins is unknown except for five proteins β-1, 3-glucanase, peroxidase, and OEE1) which are involved in plant defense and oxygen enhancement. Thus, *V. rotundifolia* and Florida hybrid bunch grape genotypes were able to express these proteins following infection, while *V. vinifera* lacked this capability, making them susceptible to PD. In addition, it was shown that xylem sap of the cultivar Noble (*V. rotundifolia*) was more resistant to protein breakdown by *X. fastidiosa* compared to that of cultivar Chardonnay (*V. vinifera*) [36], suggesting that *V. rotundifolia* xylem sap may possess protease inhibitor activity.

4. References

1. Olien, W. C., & Hegwood. C. P. (1990). Hort Science, 25, 726-831.
2. Clayton, C. N. (1985). NC Agricultural Experiment Station Bulletin, 451, 37.
3. Gardner, M. W., & Hewitt, W. B. (1974). Bulletin, Department of Plant Pathology, University of California, Berkley and Davis. 225.
4. Gray, D. (2003). New plants for Florida: Grape. Circular 1440. In R. L. Jones, M. L. Duryea & B. J. Treat (Eds.), Florida agricultural experiment station. Gainesville: Institute of Food and Agricultural Sciences, University of Florida.
5. Hopkins, D. L., & Purcell, A. H. (2002). Plant Disease, 86, 1056-1066. doi:10.1094/PDIS. 2002.86.10.1056.
6. Davis, M. J., Purcell, A. H., & Thompson, S. V. (1981). Current Microbiology, 5, 309-314. doi:10.1007/BF01566883.
7. Biles, C. L., & Abeles, F. B. (1991). Plant Physiology, 96, 597-601. doi:10.1104/pp. 96.2.597.
8. Lopez-Millan, A. F., Morales, F., Abadia, A., & Abadia, J. (2000). Plant Physiology, 124, 878-884.
9. Andersen, P. C., Brodbeck, B. V., & Mizell, R. F., 111. (1993). Physiologia Plantarum, 89, 783-790. doi:10.1111/j.1399-3054.1993.tb05285.x.
10. Andersen, P. C., Brodbeck, B. V., & Mizell, R. F., III. (1995). Journal of the American Society for Horticultural Science, 120, 36-42.
11. Rep, M., Dekker, H. L., Vossen, J. H., Boer, A. D., Houterman, P. M., Speijer, D., et al. (2002). Plant Physiology, 130, 904-917. doi:10.1104/pp.007427.
12. Rep, M., Dekker, H. L., Vossen, J. H., Boer, A. D., Houterman, P. M., Koster, C. G., et al. (2003). FEBS Letters, 534, 82-86. doi:10.1016/S0014-5793(02)03788-2.
13. Houterman, P. M., Speihjer, D., Dekker, H. L., De Koster, C. G., Cornelissen, B. J. C., & Rep. M. (2007). Molecular Plant Pathology, 8, 215-221. doi:10.1111/j.1364-3703.2007.00384.x.
14. van Loon. L. C., & van Strien, E. A. (1999). Physiological and Molecular Plant Pathology, 55, 85-97. doi:10.1006/pmpp.1999.0213.
15. Buhtz, A., Kolasa, A., Arlt, K., Walz, C., & Kehr, J. (2004). Planta, 219, 610-618. doi:10.1007/s00425-004-1259-9.
16. Ceccardi, T. L., Barthe, G. A., & Derrick, K. S. (1998). Plant Molecular Biology, 38, 775-783. doi:10.1023/A:1006039016393.
17. Chivasa, S., Ndimba, B. K., Simon, W. J., Lindsey, K., & Slabas, A. R. (2005). The Plant Cell, 17, 3019-3034. doi:10.1105/tpc.105.036806.
18. Vasanthaiah, H. K. N., Katam, R., & Basha, S. M. (2008). Applied Biochemistry and Biotechnology, doi:10.1007/s12010-008-8380-3.
19. Yemm, E. W., & Cocking, E. C. (1955). Analyst (London), 80, 209-213. doi:10.1039/an9558000209.
20. Yemm, E. W., & Willis, A. J. (1954). The Biochemical Journal, 57, 508-514.
21. Sambrook, J., Fritsch, E. F., & Maniatis, T. (2000). Molecular cloning: A laboratory manual (2nd ed.). Cold Spring Harbor: Cold Spring Harbor Laboratory Press.
22. Purcell, A. H. (2003) http://www.cnr.bcrkeley.edu/xylella/control/central-valley-guidelines.html.
23. Basha, S. M. (1979). Plant Physiology, 63, 301-306. doi:10.1104/pp.63.2.301.
24. Basha, S. M., & Roberts, R. M. (1981). Plant Physiology, 67(5), 936-939. doi:10.1104/pp.67.5.936.
25. Shen, S., Yuxiang, J., & Kuang, T. (2003). Proteomics, 3, 527-535. doi:10.1002/pmic.200390066.
26. Kehr, J., Buhtz, A., & Giavalisco, P. (2005). BMC Plant Biology, 5, 11. doi:10.1186/1471-2229-5-11.
27. Trudel, J., Grenier, J., Potvin, C., & Asselin, A. (1998). Plant Physiology, 118, 1431-1438. doi:10.1104/pp.118.4.1431.
28. Chinnasamy, G. (2005). In Z. A. Siddiqui (Ed.), PGPR: Biocontrol and Biofertilization, pp. 233-255. Netherlands: Springer.
29. Welinder, K. G. (1992). Current Opinion in Structural Biology, 2, 388-393. doi:10.1016/0959-440X(92) 90230-5.
30. Young, S. A., Guo, A., Guikema, J. A., White, F. F., & Leach, J. E. (1995). Plant Physiology, 107(4), 1333-1341. doi:10.1104/pp.107.4.1333.
31. Durrant, W. E., & Dong, X. (2004). Annual Review of Phytopathology, 42, 185-209. doi:10.1146/annurev.phyto.42.040803.140421.
32. Harman, G. E., Howell, C. R., Vitebro, A., Chet, I., & Lorito, M. (2004). Nature Reviews Microbiology, 2, 43-56. doi:10.1038/nrmicro797.

33. Tamura, N., Inoue, Y., & Chenaie. G. M. (1985). BBA-Bioenergetics, 976(2-3), 173-181. doi:10.1016/S0005-2728(89)80227-0.
34. Bhattacharyya, A., Stilwagen, S., Reznik, G., Feil, H., Eil, S. W., & Anderson, I. (2002). Genetical Research, 12, 1556-1563. doi:10.1101/gr.370702.
35. Dalk, K. (2002) Genome News Network. http://www.genomenewsnetwork.orglarticles/09_02/xylella.shtml.
36. Leite, B., Andersen, P. C., & Ishida, M. L. (2004). FEMS Microbiology Letters, 230, 283-290. doi:10.1016/S0378-1097(03)00917-0.

III. Identification and Characterization of Genes Associated with Anthracnose Tolerance Certain embodiments of the current invention teach a functional genomics approach to identifying and characterizing genes associated with anthracnose resistance/tolerance in Florida Hybrid bunch grapes. A study was carried out to isolate differentially expressed proteins and genes upon *Elsinoe* infection in anthracnose-tolerant grape genotypes. Two-dimensional gel electrophoretic analysis of leaf protein revealed expression of mitochondrial ATPase, glutamine synthetase and continued expression of ribulose 1-5 bisphosphate-carboxylase upon *Elsinoe* infection by anthracnose-tolerant Florida Hybrid bunch grape genotypes suggesting that these proteins help them maintain normal physiological process. Further, differentially expressed genes were isolated using Differential Display RT-PCR and Subtractive Hybridization techniques upon *Elsinoe* inoculation of grape leaves. DDRT-PCR results revealed significant up-regulation of several cDNA transcripts in tolerant genotype compared to susceptible genotype studied. Subtractive hybridization also yielded several unique cDNAs by tolerant genotypes compared to susceptible ones. These uniquely expressed transcripts were isolated, sequenced and identified as chalcone synthase, stilbene synthase, PR proteins, chitinase, protein/sugar kinase and transcription factor.

Expressions of these genes were confirmed through real time PCR analysis, and expression was found only in anthracnose-tolerant genotypes. Induction of these novel genes upon *Elsinoe* infection in tolerant genotypes indicates their adaptation mechanism for *Elsinoe* infestation. This result clearly suggests that anthracnose-tolerant genotypes were able to express a series of genes upon *Elsinoe* infection to suppress pathogen growth, whereas anthracnose-susceptible cultivar failed to do so. These genes appear to play a role in inducing anthracnose tolerance in Florida hybrid bunch grape genotypes.

The objectives of this study were to identify the pathogen isolated from the muscadine grapevines and to evaluate the disease tolerance potential of muscadine grape genotypes by a combination of screening approaches. These screening approaches included disease scoring after vineyard inspection, susceptibility testing via bioassay culture filtrates, and molecular biology techniques such as gene [chalcone synthase (CHS), stilbene synthase (StSy), polygalacturonase inhibiting protein (PGIP), chitinase (CHI) and lipid transfer protein (LTP)] expression studies following fungal inoculation. These genes are known to be involved in fungal disease development of fruit crops.

Florida hybrid bunch grape (*Vitis* spp.) cultivars with commercial value are susceptible to anthracnose disease caused by the fungi, *Elsinoë ampelina*. The Florida grape industry is keen on improving anthracnose tolerance characteristics of these grape cultivars as the cultivation of European grapes is limited in Southeastern United States due to Pierce's disease incidence. In this connection, a molecular approach was taken to identify and characterize the gene(s) differentially expressed upon infestation with *E. ampelina* in selected Florida hybrid bunch grape cultivars differing in their disease tolerance level.

Variation in gene expressions was monitored by employing Differential Display RT-PCR (DDRT-PCR) and subtractive hybridization (SH). DDRT-PCR results showed significant up-regulation of transcripts ranging between 200 and 800 bps in anthracnose-tolerant (cvs. Blue Lake and Lake Emerald) grape cultivars compared to anthracnose-susceptible (cvs. Suwanee and Blanc du Bois) cultivars. SH also yielded several partial cDNAs upon infection in anthracnose-tolerant cultivars.

The transcripts that were unique induced in tolerant cultivars were identified as Chitinase III (SEQ ID NO:32), PR 4 (SEQ ID NO:33), PR 10 (SEQ ID NO:34), chalcone synthase (SEQ ID NO:31) and stilbene synthase (SEQ ID NO:1), protein/sugar kinases, and transcriptional factor. Expressions of these genes were validated using real-time PCR analysis. The results showed that these genes were more rapidly expressed in tolerant cultivars within a day after inoculating with *E. ampelina* and peaking by day 3. compared to susceptible cultivars. Induction of these anti-fungal genes appears to enable tolerant cultivars to withstand fungal infestation compared to susceptible cultivars.

EXAMPLES

1. Results and Discussion a. Pathogen Isolation and Characterization

Figure 9A:
FIGS. 9A-9D depict anthracnose symptoms on the grapevine leaves and the pathogen (*Elsinoe*) isolated from the infected leaves.
Figure 9B:
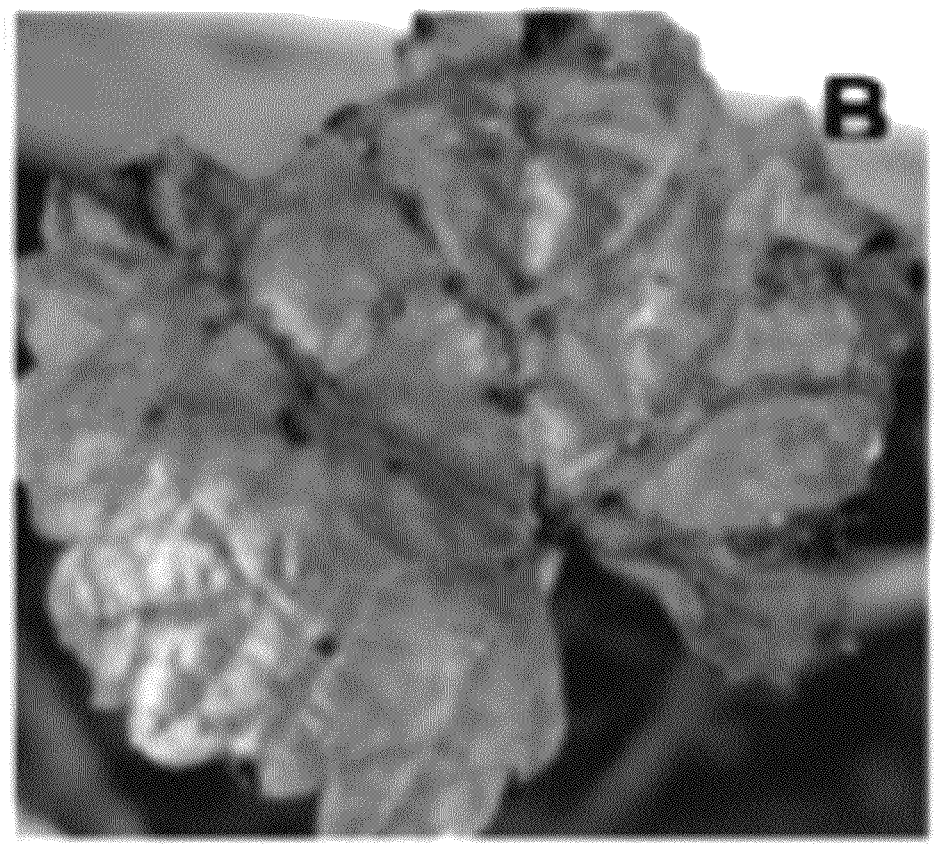
Figure 9C:
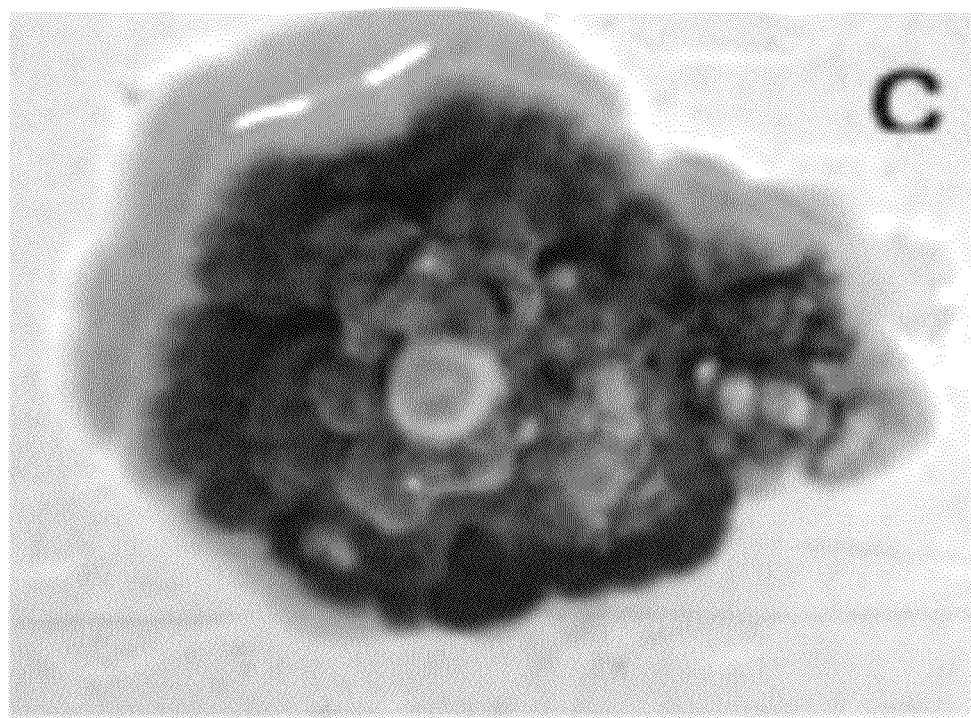
Figure 9D:
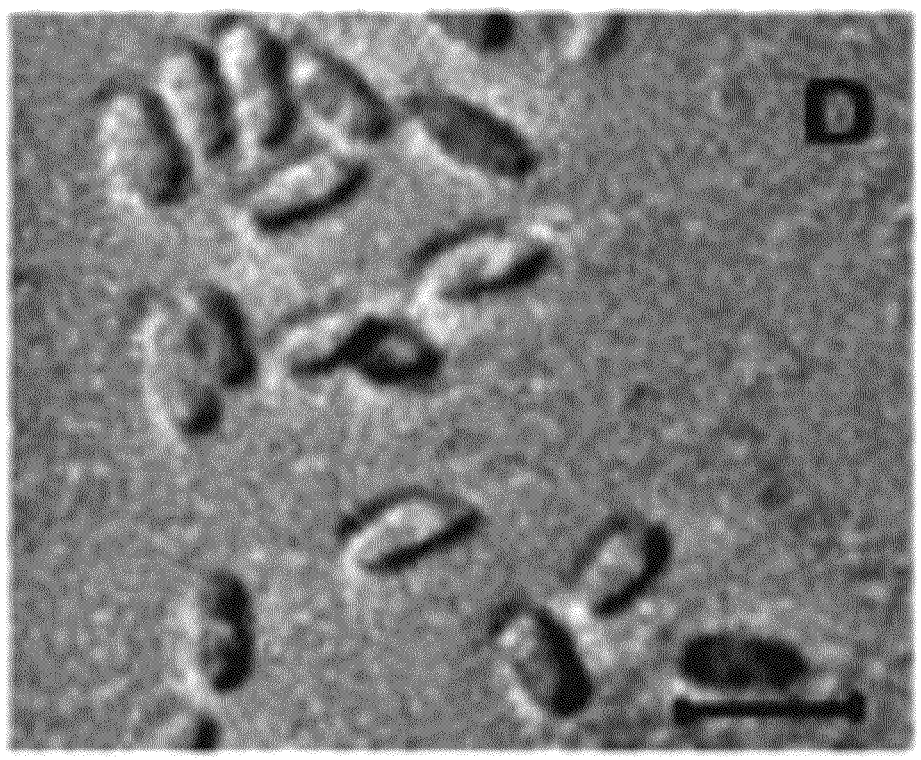
Figure 10A:
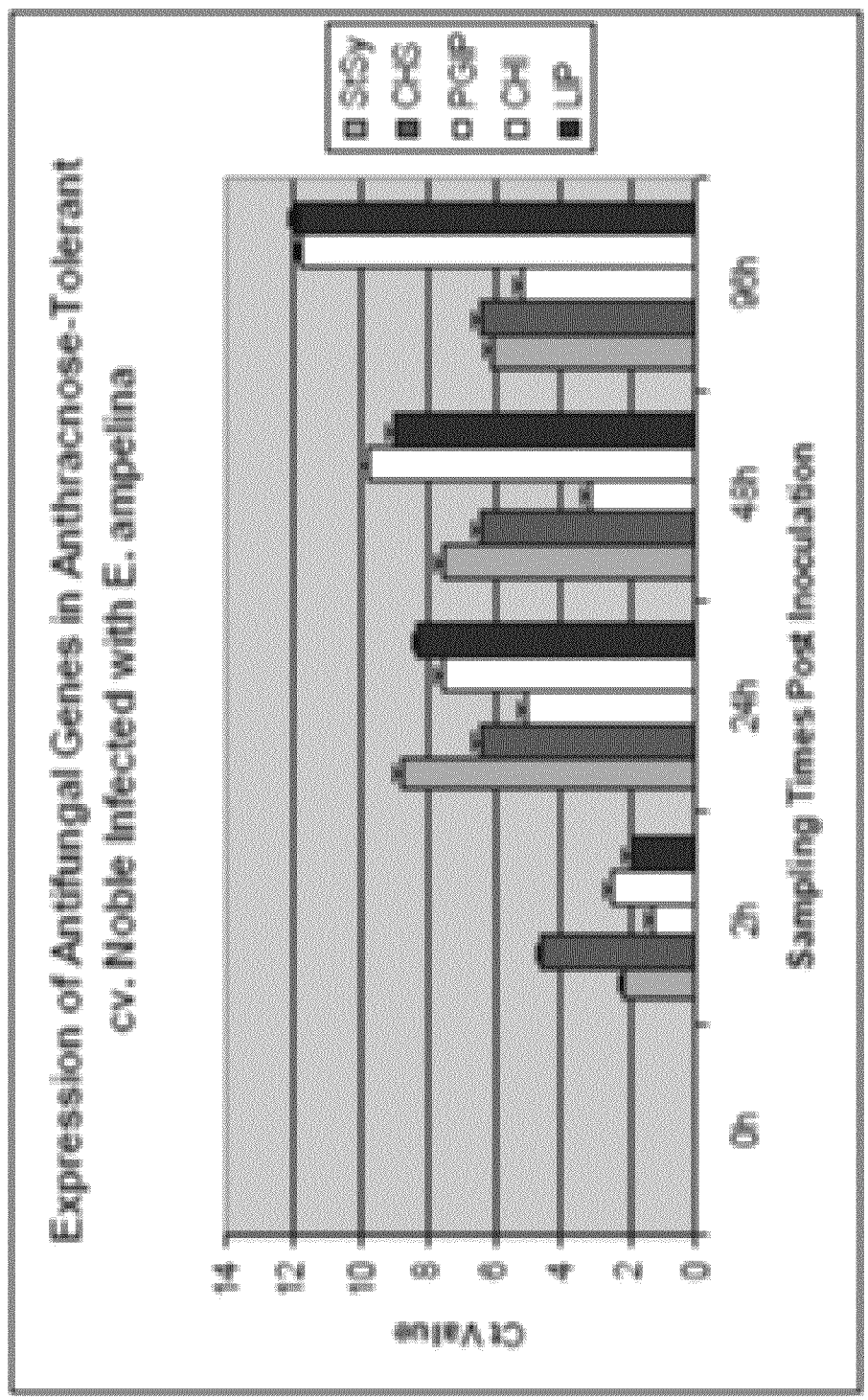
FIG. 10A depicts expression of antifungal genes based on Ct values (average of three reactions) measured through real-time PCR at different time periods post inoculation in muscadine cultivar Noble (anthracnose-tolerant) and B Hunt (anthracnose-susceptible). Ubiquitin was used as an internal control in this experiment with StSy (Stilbene Synthase) (SEQ ID NO:1), CHS (Chalcone Synthase) (SEQ ID NO:31), PGIP (Polygalacturonase Inhibiting Protein), CHI (Chitinase) (SEQ ID NO:32), and LIP (Lipid Transfer Protein).
Figure 10B:
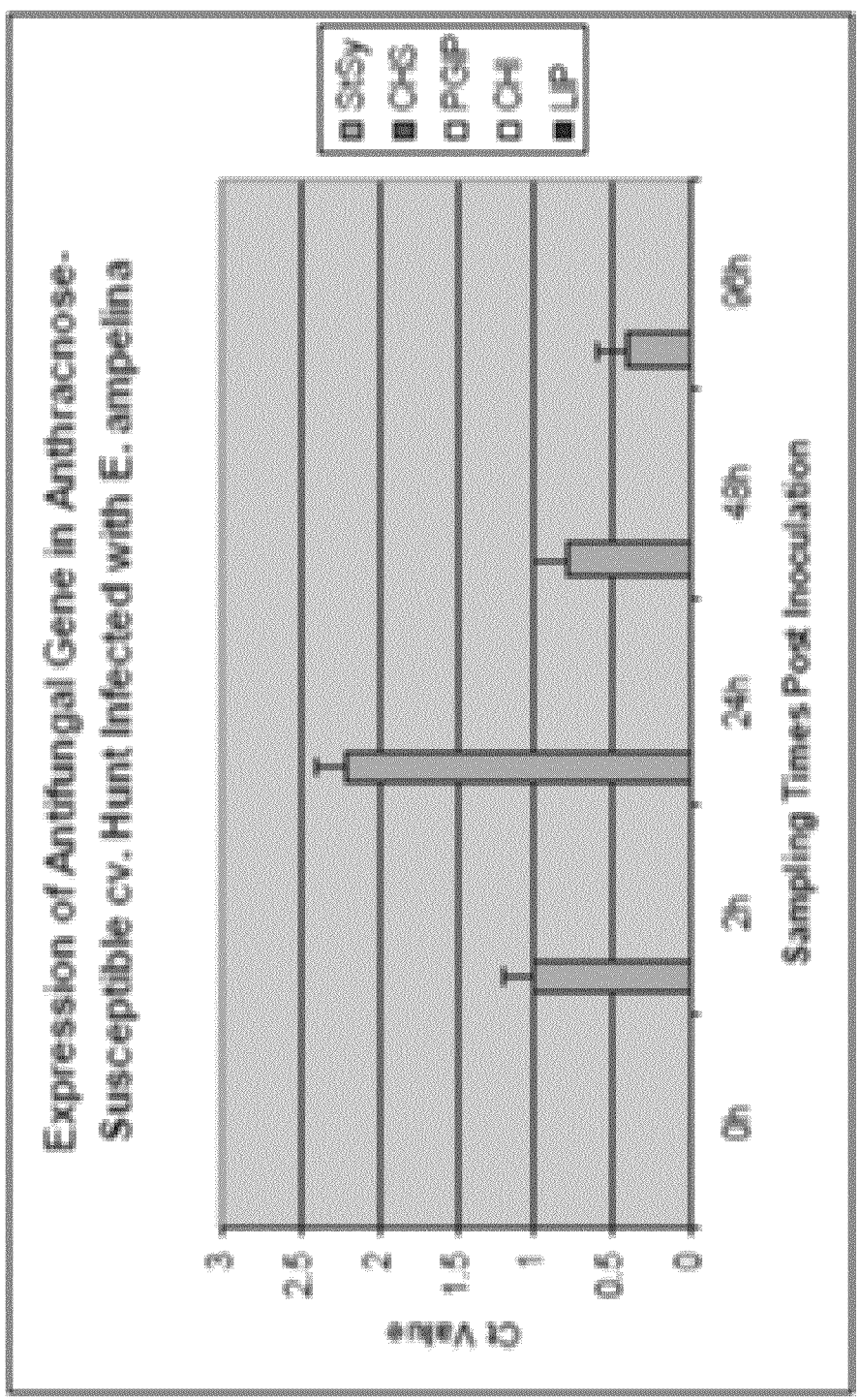
FIG. 10B depicts expression of antifungal genes based on Ct values (average of three reactions) measured through real-time PCR at different time periods post inoculation in muscadine cultivar Hunt (anthracnose-susceptible). Ubiquitin was used as an internal control in this experiment with StSy (Stilbene Synthase), CHS (Chalcone Synthase), PGIP (Polygalacturonase Inhibiting Protein), CHI (Chitinase), and LIP (Lipid Transfer Protein).

Fungus isolated from infected muscadine grapevine leaves showed slow growth (3.5 cm in diameter in 10 days) and dark red mounds with some mycelia on PDA (FIG. 9C). Spores ranged from 11.0 to 16.5 μm×3.9 to 5.7 μm, cylindrical and hyaline with pointed ends (FIG. 9D), which was consistent with previous reports for *E. ampelina* [3]. The fungus was identified not only by microscopic observations of morphological characteristics, but also by PCR amplification of fungal DNA. Electrophoresis of the obtained PCR products on agarose gel (1.2%) showed a single expected 500 bp amplified band (FIG. 10). These results clearly confirmed that the fungus isolated from the lesions of the muscadine grapevine leaves (cv. 'Hunt') was the same species as *E. ampelina*, the causal agent of anthracnose in grapevines.

b. Pathogenicity Testing

To test for possible pathogenicity of the fungus, the incidence of symptoms was investigated on anthracnose-tolerant and susceptible cultivars after spraying with fungal spore suspension (2×105 spores per mL). Necrotic lesions associated with the anthracnose fungus appeared 4 days after inoculation with fungal spore suspension on cvs. 'Cabernet Sauvignon' (*V. vinifera*) and 'Hunt' (*M. rotundifolia*) (FIG. 9B). The fungus isolated from anthracnose lesions of muscadine grapevine leaves had high pathogenicity (was virulent) and produced anthracnose disease symptoms on cultivars 'Cabernet Sauvignon' and 'Hunt'. Further inoculation using the above isolated fungus to study the transcriptome analysis of the anti-fungal genes in both *Elsinoë*-tolerant and -susceptible cultivars substantiates that the leaf samples used were infected with *E. ampelina*.

c. In-Situ and Ex-Situ Analysis to Determine the Tolerance Level of Muscadine Cultivars Both in-situ and er-situ analysis were carried out to screen the grape cultivars tolerant to anthracnose for further use in a breeding program. The incidence of anthracnose symptoms was rated based on their natural infection in the vineyard and the varietal responses were evaluated through bioassay using culture filtrates from fungus Elsinoë. Finally, the tolerance level of muscadine cultivars was tested using gene expression studies of selected defense-related genes.

d. Anthracnose Incidence in the Field

Vineyard investigation in 2006 and 2007 pointed out that the anthracnose symptoms were visible on the leaves, tendrils and stems of the muscadine grapevines. Prior to 2006, the incidence of anthracnose on muscadine cultivars was not significant. The level of shoot infection varied among the *V. rotundifolia* genotypes considered to be immune to anthracnose (Table 3). Among the 54 muscadine cultivars studied, 23 cultivars were found to be immune to *Elsinoë* infestation, 12 cultivars showed incidence≤1, 16 cultivars showed incidence between 1.1 to 4.2 on a 0 to 5 scale. Among the muscadine grape cultivars tested, cultivars 'Janet', 'Scarlet', 'Digby', and 'Watergate' had the highest incidence score of 4.2, 3.1, 2.5 and 2.5, respectively. This data clearly shows that the muscadine cultivars are not immune to anthracnose infection. In the case of the anthracnose-susceptible Florida hybrid bunch grape (cv. Blanc du Bois and Orlando Seedless) and *V. vinifera* (cv. Cabernet Sauvignon), the shoot incidence was recorded 5 with maximum incidence revealing their venerability to anthracnose.

TABLE 3

Incidence of anthracnose in muscadine grapevines in the vineyards. Incidence of anthracnose was expressed as mean number (±SE, n = 9) of shoots with lesions from 10 leaves in upper part of shoots from the shoot tip, and on the shoots in the vineyard. Score range from 0 (tolerant) to 5 (highly susceptible), where 0 = no necrosis; 1 = necrotic lesions covering 10% of the leaf area; 2 = necrotic lesions covering 20% of the leaf area; 3 = necrotic lesions covering 50% of the leaf area; 4 = necrotic lesions covering 75% of the leaf area; and 5 = necrotic lesions covering 90% of the leaf area.

| Variety | Shoot infection |
|---|---|
| African Queen | 1.1 ± 0.17 |
| Alachua | 0.6 ± 0.11 |
| Albermale | 0.7 ± 0.17 |
| Black Beauty | 0 |
| Black Fry | 0 |
| Carlos | 1.0 ± 0.33 |
| Cowart | 0 |
| Darlene | 0 |
| Digby | 2.5 ± 0.33 |
| Dixie | 0 |
| Dixie Land | 1.5 ± 0.18 |
| Dixie Red | 0.4 + 0.11 |
| Doreen | 0 |
| Early Fry | 0 |
| Farrer | 1.5 ± 0.23 |
| Florida Fry | 0.8 + 0.15 |
| Fry | 0.5 ± 0.15 |
| Fry Seedless | 2.5 ± 0.56 |
| Golden Isle | 0.4 ± 0.11 |
| Granny Val | 1.8 ± 0.43 |
| Higgins | 1.7 ± 0.37 |
| Hunt | 1.8 ± 0.24 |
| Ison | 0 |
| Janebell | 0 |
| Janet | 4.2 ± 0.58 |
| Jumbo | 2.1 ± 0.29 |
| Late Fry | 2.1 ± 0.24 |
| Loomis | 0 |
| Magnolia | 0.8 ± 0.17 |
| Nesbitt | 0 |
| Noble | 0.4 ± 0.15 |
| Pam | 0 |
| Pineapple | 1.8 ± 0.24 |
| Pride | 0.8 ± 0.17 |
| Regale | 0 |
| Rosa | 0 |
| Scarlet | 3.1 ± 0.48 |
| Scupernong | 0.4 ± 0.11 |

TABLE 3-continued

Incidence of anthracnose in muscadine grapevines in the vineyards. Incidence of anthracnose was expressed as mean number (±SE, n = 9) of shoots with lesions from 10 leaves in upper part of shoots from the shoot tip, and on the shoots in the vineyard. Score range from 0 (tolerant) to 5 (highly susceptible), where 0 = no necrosis; 1 = necrotic lesions covering 10% of the leaf area; 2 = necrotic lesions covering 20% of the leaf area; 3 = necrotic lesions covering 50% of the leaf area; 4 = necrotic lesions covering 75% of the leaf area; and 5 = necrotic lesions covering 90% of the leaf area.

| Variety | Shoot infection |
|---|---|
| Senoia | 0 |
| Southern Home | 0 |
| Southern Land | 0 |
| Sterling | 0 |
| Sugargate | 0 |
| Sugarpop | 1.0 ± 0.15 |
| Summit | 1.3 ± 24 |
| Supreme | 0 |
| Sweet Jenny | 1.3 ± 0.18 |
| Tara | 0 |
| Triumph | 0 |
| Watergate | 2.5 ± 0.17 |
| Welder | 0 |
| Blanc du Bois | 5.0 ± 0.24 |
| Orlando Seedless | 5.0 ± 0.29 |
| Cabernet Sauvignon | 5.0 ± 0.24 | e. Bioassay with Culture Filtrates

Further validation of the 36 muscadine grapevine and 4 *Vitis* sp. cultivars to anthracnose tolerance was carried out employing Yun et al.'s [12] screening system using culture filtrates from *E. ampelina*. The results of the bioassay with culture filtrates showed that some cultivars were tolerant, some were susceptible and while others were moderately resistant. All of the cultivars, except 'Late Fry', 'Noble', 'Pam', 'Senoi', 'Southern Home', 'Sweet Jenny' and 'Welder', developed necrosis after treatment with *Elsinoë* culture filtrate (1:1 dilution) on the wounded surface (Table 4). Eleven cultivars developed necrosis incidence at 1:4 dilution of the culture filtrate and 4 of them at 1:8 dilution. The development of necrosis in the anthracnose-susceptible cultivars (*Vitis* sp. cv. 'Blanc du Bois' and 'Orlando Seedless'; *V. vinifera* cv. 'Chardonnay' and 'Cabernet Sauvignon') was significantly higher than in the tolerant cultivars. The leaf of Florida hybrid bunch grape cv. 'Blanc du Bois' developed necrosis of 2-3 mm over the wounded spot, even at 1:16 dilution. This study also demonstrates that not all muscadine cultivars are immune to anthracnose disease. The spectrum of sensitivity to the culture filtrates was highly consistent with susceptibility to anthracnose in a number of grapevine cultivars observed during the vineyard investigation.

TABLE 4

Comparison of different grape cultivars in their responses to the culture filtrates of *E. ampelina*. The superscript "z" refers to 4, necrotic area >3 mm diameter from wounded spot; 3, necrotic area of 2-3 mm around wounded spot; 2, necrosis spreading to form area on wounded spot; 1, slight necrosis; 0, no necrosis.

| | Dilution of culture filtrates | | | |
|---|---|---|---|---|
| Variety | 1:1 | 1:4 | 1:8 | 1:16 |
| African Queen | 1 | 0 | 0 | 0 |
| Alachua | 1 | 0 | 0 | 0 |
| Albermale | 1 | 0 | 0 | 0 |
| Black Beauty | 1 | 0 | 0 | 0 |
| Carlos | 1 | 0 | 0 | 0 |
| Cowart | 1 | 0 | 0 | 0 |

TABLE 4-continued

Comparison of different grape cultivars in their responses to the culture filtrates of E. ampelina. The superscript "z" refers to 4, necrotic area >3 mm diameter from wounded spot; 3, necrotic area of 2-3 mm around wounded spot; 2, necrosis spreading to form area on wounded spot; 1, slight necrosis; 0, no necrosis.

| Variety | Dilution of culture filtrates | | | |
|---|---|---|---|---|
| | 1:1 | 1:4 | 1:8 | 1:16 |
| Darlene | 1 | 1 | 1 | 0 |
| Dixie Land | 3 | 2 | 0 | 0 |
| Dixie Red | 3 | 2 | 1 | 0 |
| Early Fry | 1 | 1 | 0 | 0 |
| Farrer | 2 | 1 | 0 | 0 |
| Florida Fry | 1 | 0 | 0 | 0 |
| Fry | 2 | 2 | 1 | 0 |
| Fry Seedless | 2 | 1 | 1 | 0 |
| Golden Isle | 0 | 0 | 0 | 0 |
| Granny Val | 1 | 0 | 0 | 0 |
| Higgins | 1 | 0 | 0 | 0 |
| Hunt | 3 | 2 | 1 | 0 |
| Janet | 1 | 0 | 0 | 0 |
| Late Fry | 0 | 0 | 0 | 0 |
| Loomis | 1 | 0 | 0 | 0 |
| Noble | 0 | 0 | 0 | 0 |
| Pam | 0 | 0 | 0 | 0 |
| Pineapple | 1 | 0 | 0 | 0 |
| Pride | 1 | 0 | 0 | 0 |
| Regale | 1 | 0 | 0 | 0 |
| Rosa | 2 | 1 | 0 | 0 |
| Scarlett | 2 | 1 | 0 | 0 |
| Scupermong | 1 | 0 | 0 | 0 |
| Senoia | 0 | 0 | 0 | 0 |
| Southern Home | 0 | 0 | 0 | 0 |
| Southern Land | 1 | 0 | 0 | 0 |
| Sugargate | 2 | 1 | 0 | 0 |
| Sugarpop | 1 | 0 | 0 | 0 |
| Sweet Jenny | 0 | 0 | 0 | 0 |
| Welder | 0 | 0 | 0 | 0 |
| Blanc du Bois | 4 | 3 | 3 | 3 |
| Orlando Seedless | 4 | 2 | 2 | 0 |
| Chardonnay | 3 | 2 | 0 | 0 |
| Cabernet Sauvignon | 3 | 2 | 0 | 0 | f. Gene Expression Studies During the Course of Infection

In order to further validate the anthracnose tolerance level of different grape cultivars, real-time PCR analysis was carried out with the selected defense-related genes. Based on the field investigation and bioassay analysis, five anthracnose-tolerant and anthracnose-susceptible cultivars, along with one Florida hybrid bunch and *V. vinifera* cultivars were randomly selected for this study. The choice of the primers was based on ESTs, genes and mRNA sequences of *Vitis* sp. found in the public domain. Initial standard PCR amplification revealed that the primer pairs targeted a single gene within a given gene family, indicating good quality and absence of genomic contamination in the template cDNA (data not shown). Ubiquitin was used as the internal control. The genes encoding chalcone synthase (CHS), stilbene synthase (StSy), polygalacturonase-inhibiting protein (PGIPs), chitinase (CHI) and lipid-transfer protein (LIP) were highly expressed in anthracnose-tolerant cultivar 'Noble' (*M. rotundifolia*) upon *Elsinoë* inoculation (FIG. 10) but were completely absent in susceptible cv. 'Hunt' (*M. rotundifolia*), 'Blanc du Bois' (*Vitis* sp.) and 'Cabernet Sauvignon' (*V. vinifera*) based on the Ct values obtained through real-time PCR analysis. Except for StSy expression, which was observed at low levels in anthracnose-susceptible cultivar 'Hunt'.

A similar pattern of expression was also observed in the other anthracnose-tolerant muscadine cultivars studied viz., 'Pam', 'Senoi', 'Southern Home' and 'Welder' and anthracnose-susceptible muscadine cultivars studied viz., 'Fry Seedless'. 'Granny Val', 'Higgins' and 'Janet' (data not shown), further confirming their tolerance level. This further indicates that variability exists among muscadine and other grape cultivars for anthracnose tolerance. The expression levels of all the five genes studied in muscadine varied during the course of *Elsinoe* infection, indicating their role in anthracnose tolerance.

g. Discussion

The level of tolerance to *E. ampelina* varies among different cultivars of grapes that affect their production [12,19]. Until now it was believed that most of the muscadine grapevines are immune to anthracnose caused by *E. ampelina*. However, the incidence of anthracnose was observed on 40% of the leaves, tendrils and stems of muscadine cultivars. This observation led to this study to analyze anthracnose tolerance among muscadine cultivars through strict and stringent process.

Two (2) consecutive years of field study showed variation in the level of shoot infection among the muscadine cultivars to *E. ampelina* infection (Table 3). The incidence of disease varied among muscadine cultivars from ≤1 to 4.2 on a 0 to 5 scale, whereas anthracnose-susceptible Florida hybrid bunch grape cultivars studied documented 5.0, disclosing their susceptibility to anthracnose. Among the muscadine cultivars studied 45% of them were found immune to anthracnose, while cultivars 'Janet', 'Scarlet', 'Digby', and 'Watergate' were found highly susceptible. The above study revealed that all muscadine grape cultivars were not immune or highly resistant to anthracnose disease. Further, the tolerance to anthracnose in various muscadine grape cultivars was evaluated by using bioassay with culture filtrates from the pathogen. These results were consistent with those from field tests. Susceptible cultivars were found sensitive to eight-fold diluted culture filtrates, but resistant cultivars were not affected, even by the original culture filtrates. A similar pattern has been reported in apple with AM-toxins from *Alternaris mali* [20,21] and pear leaves with AK-toxins from *A. kikuchiana* [22,23].

Figure 11:
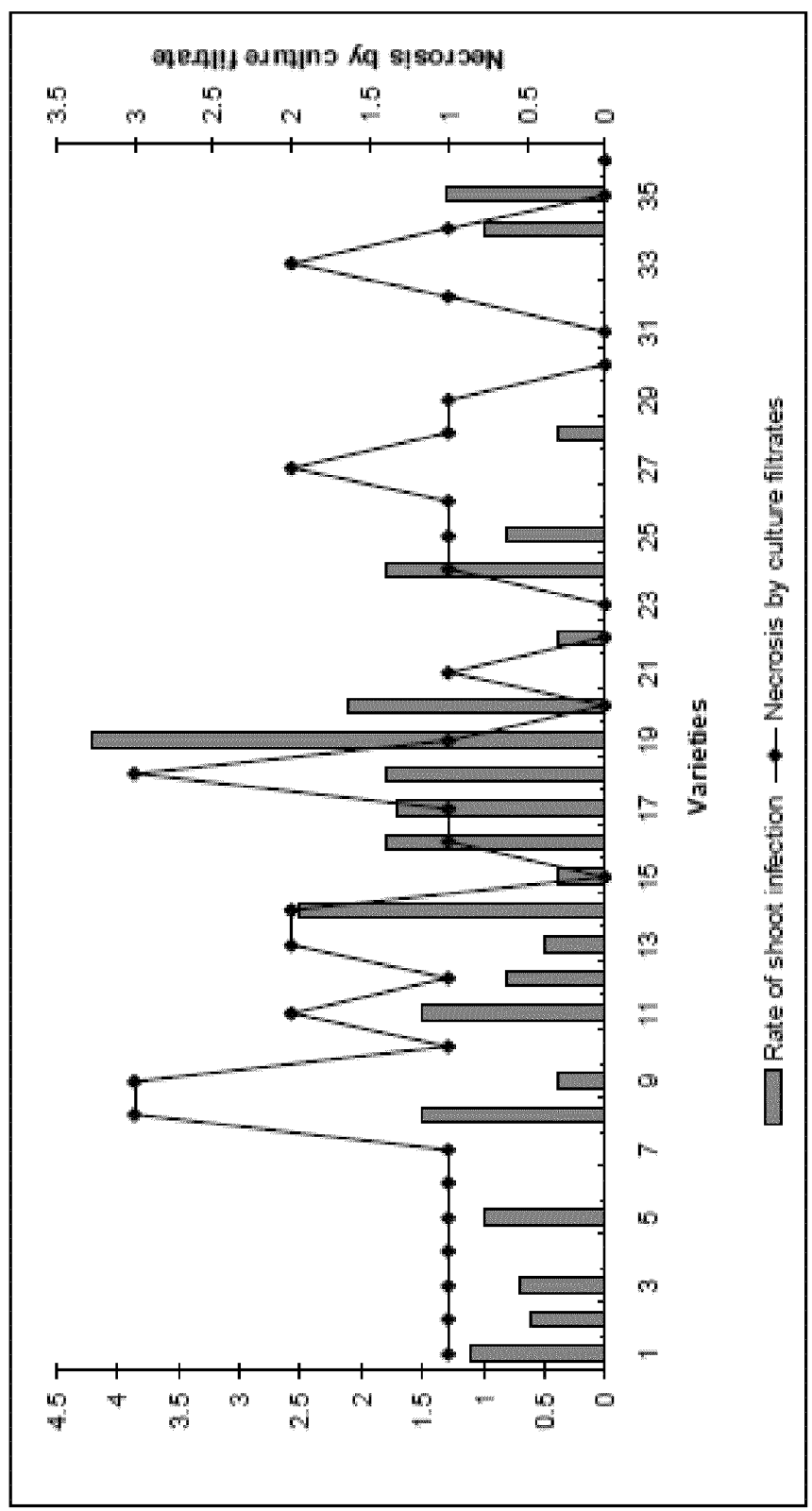
FIG. 11 shows comparison between anthracnose incidence in vineyard and necrosis resulted from bioassay of culture filtrates from *E. ampelina*. 1; 'African Queen', 2; 'Alachua', 3; 'Albermale', 4; 'Black Beauty', 5; 'Carlos', 6; 'Cowart', 7; 'Darlene', 8; 'Dixie Land', 9; 'Dixie Red', 10; 'Early Fry', 11; 'Farrer', 12; 'Florida Fry', 13; 'Fry', 14; 'Fry Seedless', 15; 'Golden Isle', 16; 'Granny Val', 17; 'Higgins', 18; 'Hunt', 19; 'Janet', 20; 'Late Fry', 21; 'Loomis', 22; 'Noble', 23; 'Pam', 24; 'Pineapple', 25; 'Pride', 26; 'Regale', 27; 'Rosa', 28; 'Scarlet', 29; 'Scupernong', 30; 'Senoia', 31; 'Southern Home', 32; 'Southern Land', 33; 'Sugargate', 34; 'Sugarpop', 35; 'Sweet Jenny', 36; 'Welder'.; Rate of shoot infection in vineyard; Necrosis by bioassay of culture filtrates from *E. ampelina*. Score range as described above in Table 3 and Table 4.

A comparative analysis of both field and bioassay studies revealed that 19 muscadine cultivars ('Black Beauty', 'Carlos', 'Cowart', 'Darlene', 'Early Fry', 'Florida Fry', 'Golden Isle', 'Loomis', 'Pride', 'Noble', 'Pam', 'Regale', 'Scarlet', 'Scupernong', 'Senoi', 'Southern Home', 'Southern Land', 'Sugar Pop' and 'Welder') among 51 studied were immune to anthracnose infection (FIG. 11) showing 0 to S1 scale shoot infection and 0 to 1 (slight necrosis) after *Elsinoe* infection. Appearance of slight necrosis on the leaf of few cultivars may be due to tissue damage during artificial inoculation and infection, which is not significant. This study also clearly demonstrates that not all muscadine cultivars are immune to anthracnose disease. The spectrum of sensitivity to the culture filtrates was highly consistent with susceptibility to anthracnose in a number of grapevine cultivars observed during the vineyard investigation. The muscadine cultivars with 0 to 1.5 scale showing necrotic lesions covering up to 10% of leaf area can be successfully considered for grape breeding program. The infection of *Elsinoë* and appearance of slight necrosis on leaf of few cultivars may be attributed to a hypersensitive reaction.

Further validation of anthracnose tolerance level of different grape cultivars was carried out using real-time PCR analysis and selective antifungal specific genes. Expression of Chalcone synthase (CHS), stilbene synthase (StSy), polygalacturonase-inhibiting protein (PGIPs), chitinase (CHI) and lipid-transfer protein (LIP) were found only in the anthracnose-tolerant muscadine cultivars studied (FIG. 10A). Expression of these genes was rapid 24 h of *Elsinoë* inoculation. Similar validation of expression of pathogenesis-related genes has been recorded in grapevine against *Uncinula necator* that causes powdery mildew and rupestris stem pitting-associated virus (GRSPaV) [24,25]. Chalcone synthase is a phytoalexin biosynthetic enzyme [26], which is involved in defense against fungal diseases. CHS catalyses a key step in the synthesis of many secondary compounds with demonstrated antifungal activity [27] in *Arabidopsis* against the growth of *Pythium mastophorum*, which causes root rot [28]. Higher expression of CHS in anthracnose-tolerant muscadine cv. 'Noble' and other cultivars studied clearly indicates its tolerance mechanism.

2. Experimental Section a. Plant Materials

The field-grown muscadine and Florida hybrid bunch grape cultivars maintained at the vineyard of the Center for Viticulture and Small Fruit Research, Tallahassee, Fla. were used for field and bioassay studies. Based on the results obtained for further transcriptome analysis, two-year-old greenhouse-grown *V. rotundifolia* (cvs. 'Noble', 'Pam', 'Senoi', 'Southern Home' and 'Welder' (anthracnose-tolerant); 'Fry Seedless', 'Granny Val', 'Higgins', 'Hunt' and 'Janet' (anthracnose-susceptible)), *V. vinifera* (cv. 'Cabernet Sauvignon') and Florida hybrid bunch grape (cv. Blanc du Bois) were used after challenging with *E. ampelina*. The greenhouse-grown plants were derived from the cuttings made from the greenhouse-maintained grape genotypes at Center for Viticulture and these plants were grown in three-gallon pots.

b. Isolation and Characterization of the Fungus

To identify *E. ampelina*, anthracnose-infected leaves of muscadine grapevine, cv. Hunt, were collected from the experimental vineyard at the Center for Viticulture and Small Fruit Research in Tallahassee, Fla. (FIG. 9A). The leaf surface was disinfected by dipping in 2% sodium hypochlorite solution for 1 min followed by 75% ethyl alcohol and then rinsed in distilled water. The leaves were placed on potato dextrose agar (PDA) medium and incubated at 28° C. under a fluorescent light. The fungus developed as a dark red mound and was isolated on PDA medium as single-conidia cultures. Single colony cultures were transferred to new plates. Colony type and spore appearance of this fungus were investigated by microscopic observations and compared with previous reports for *E. ampelina*. DNA isolated from the fungus was also analyzed by PCR amplification using the following 18sRNA based primers, 5'-TCCGTAGGTGAACCT-GCGGA-3' (left) (SEQ ID NO:37) and 5'-TCCTACCT-GATCCGAGGTCA-3' (right) (SEQ ID NO:38), designed based upon alignment of *E. ampelina* genes deposited in the NCBI database. Genomic DNA obtained from the isolate grown on Fries liquid medium [15] was amplified following the protocol of Müller et al. [16].

c. Culture and Spore Production

Several colonies of the pathogenic fungus were transferred to Fries liquid medium and incubated in a shaker incubator (140 rpm) at 28° C. for 10 days. Fungal cultures harvested by centrifugation were suspended in sterile distilled water by homogenization, poured on V-8 juice agar medium and incubated for 2 days at 28° C. under a near ultraviolet lamp for spore production. To harvest pathogenic spores, sterile distilled water was used to scrape colonies off the plates. The harvested spores were adjusted to different concentrations with sterile distilled water, and then used to inoculate the grapevine leaves.

d. Pathogenicity Test

Greenhouse-grown plants were used for this study. Spore suspension adjusted to $2 \times 10^5$ conidia per mL was sprayed onto *V. vinifera* (cv. 'Cabernet Sauvignon') and *V. rotundifolia* (cv. 'Hunt') grape cultivars, whereas control plants were sprayed with distilled water. Treated plants were immediately incubated in a humid chamber (28° C.) for 48 h, and moved to the greenhouse. The plants were inspected for appearance of symptoms on the leaves, and the degree of symptom development was recorded.

e. Disease Scoring

Field test data were collected from the experimental vineyard at the Center for Viticulture and Small Fruit Research, Florida Agricultural and Manufacturing University in Tallahassee, Fla. The field-grown plants were investigated for incidence of lesions due to anthracnose during the spring, summer and autumn of 2006 and 2007. Disease severity was assessed by counting the number of lesions and rating the symptom expression on a scale of 0 (no necrosis) to 5 (severely infected). The incidence of anthracnose was recorded from the lesions of 10 leaves on the upper part of the shoots from the shoot tip and on the shoots of 54 cultivars. The data was collected for three replicates (Table 3).

f. Bioassay with Culture Filtrates

After incubating the pathogen in Fries medium at 28° C. for 10 days, cell-free culture filtrates (CFCF) of *E. ampelina* were collected from the supernatant by centrifugation at 10,000×g for 5 min using a table top centrifuge (Eppendorf, Centrifuge 5415C) and sterilized by ultrafiltration (0.2 µm pore diameter). Muscadine grapevine leaves from 36 different cultivars located at the experimental vineyard in Tallahassee, Fla. were used for this study. Five different leaves from either upper third or fourth leaf from the shoot apex were collected from four different grape plants of each cultivar and brought to the laboratory on ice. These leaves were surface-sterilized with 75% ethanol, dipped in 2% sodium hypochlorite for 15 s and rinsed in distilled water. Later these leaves were injured with a needle tip and 30 µL of culture filtrate, diluted to 1:1, 1:4, 1:8 and 1:16 (v/v) with distilled water was deposited onto the wounded portion of the leaves. Fresh Fries medium was applied to the wounded portions of grapevine leaves as control. Leaves treated with culture filtrates and the control medium were incubated in a dark, moist chamber (>95% RH) for 3 days at 28° C. The area of the necrotic lesion around the wound was measured to evaluate the tolerance of different cultivars.

g. Gene Expression Studies i. Pathogen Inoculation

Plants grown under controlled greenhouse conditions were used in this study. For inoculation studies, spore suspension adjusted to $2 \times 10^5$ conidia per mL were sprayed onto young *V. rotundifolia* cv. 'Noble' 'Pam', 'Senoi', 'Southern Home' and 'Welder' (anthracnose-tolerant); 'Hunt', 'Digby', 'Janet', 'Scarlet' and 'Watergate' (anthracnose-susceptible)), *V. vinifera* (cv. 'Cabernet Sauvignon') and Florida hybrid bunch grape (cv. 'Blanc du Bois) plants as treatment and three plants of each cultivar were sprayed with distilled water as the control. The tolerance and susceptible of muscadine cultivars to anthracnose was based on field observance. For optimization of lesion formation, inoculated plants were incubated in a humid chamber (28° C.) for 48 h, and later moved to the greenhouse. Leaf samples were randomly collected at 0 (before inoculation), 2, 24, 48 and 96 h for RNA isolation. Sample collection was stopped after four (4) days post inoculation as the lesions appeared on leaves and young shoots at this time. Anthracnose-susceptible and anthracnose-tolerant muscadine cultivars were randomly selected based on the results of field and bioassay analysis.

ii. RNA Extraction and Analysis

Total RNA from uninfected and *Elsinoë* infected leaf tissue was isolated using modified guanidine thiocyanate extraction method [17]. The yield and quality of total RNA products were measured by absorbance at 230, 260, and 280 nm (A260/230 and A260/280 ratios) using a spectrophotometer (Nano Drop, Technologies Inc.) and by electrophoresis on a 1.5% non-denaturing agarose gel [18].

iii. Primer Design

For further validation, primers specific to *Vitis* species defense-related genes were designed to check the expression levels of these genes upon challenging with *Elsinoë* in both tolerant and susceptible grapevine cultivars. Oligonucleotide primers for chalcone synthase (CHS), stilbene synthase (StSy), polygalacturonase inhibiting protein (PGIP), chitinase (CHI) and lipid transfer protein (LTP) were designed based on sequences conserved among different *Vitis* species including *V. vinifera, V. labrusca, V. shuttleworthii, V. riparia*, and *V. rotundifolia*. The primers for qPCR were designed using Primer3 program. Primers were synthesized by WGC (Saint Louis, Mo.). Primer sequences are provided in Table 5.

20 µL with PCR-grade water. Reactions were incubated at 95° C. for 2 min initial denaturation and then cycled at 95° C. for 30 s, 60° C. for 30 s (for all genes), and 72° C. for 1 min for a total of 35 cycles followed by a final extension of 5 min at 72° C.

Quantitative or real time PCR was performed on IQ5Cycler (Bio-Rad) using a SYBR-green mix from the manufacturer. Reactions were performed in 20 µL including 20 ng RNA, 0.3 µM of each primer and 5 µL SYBER-green mix. All reactions were performed in triplicate to ensure reproducibility of the results. Amplification was carried out with one cycle at 95° C. for 15 min, eight cycles at 94° C. for 30 s, 60° C. for 40 s and, 30 cycles at 94° C. for 10 s and 60° C. for 30 s. Melting curves of the amplified products were recorded. Relative mRNA level for each sample was calculated using the relative Ct method (level=2 (Ct of the no RT control−Ct of the sample)), with Ct being the cycle number at which fluorescence surpassed background (determined during the first 10 cycles of amplification). Results were analyzed using the iCycler system sequence detection software V1.3 (Bio-Rad). Data were normalized against expression of the housekeeping gene ubiquitin.

TABLE 5

List of oligonucleotide primers used in this study for real-time PCR analysis. Ubiquitin was used as an internal control in this experiment—CHS (Chalcone Synthase)—StSy (StilbeneSynthase)—PGIP (Polygalacturonase Inhibiting Protein)—CHI (Chitinase)—LIP (Lipid Transfer Protein).

| Primer | Orientation | Sequence | SEQ ID NO. |
|---|---|---|---|
| CHS | Sense | 5'-C(ACT)TATGA(AT)GA(AG)TATCTCTG(CT)-3' | SEQ ID NO: 19 |
|  | Antisense | 5'-GAGCT(AG)GGAAAAGCCAT(ACT)GT-3' | SEQ ID NO: 20 |
| StSy | Sense | 5'-TTGGTATCTGATT(AG)(CG)TGATG-3' | SEQ ID NO: 21 |
|  | Antisense | 5'-CCAGTA(CT)TC(CT)(CT)GGATGTGTCT(AG)TC(AC)TC-3' | SEQ ID NO: 22 |
| PGIP | Sense | 5'-AG(AT)A(AG)(CT)TT(GT)GT(CGT)A(AG)(CT))TGG-3' | SEQ ID NO: 23 |
|  | Antisense | 5'-TC(AG)(CG)T(GT)AT(CT)TCCAC(AC)AGCAT-3' | SEQ ID NO: 24 |
| CHI | Sense | 5'-TCGTGAAAAGAGAAGGGAACTCA-3' | SEQ ID NO: 25 |
|  | Antisense | 5'-AAAAACGTCTGGAAGCAAAAGC-3' | SEQ ID NO: 26 |
| LIP | Sense | 5'-TTGCTCCAGACCTGATTTTTGAT-3' | SEQ ID NO: 27 |
|  | Antisense | 5'-TGGCACAGTTCAAACATTGCA-3' | SEQ ID NO: 28 |
| Ubiquitin | Sense | 5'-TGTCCTCTGTTTACTTGGTGGTAT-3' | SEQ ID NO: 29 |
|  | Antisense | 5'-CTTCAAGGGTAATGGTCTTCTCAAC-3' | SEQ ID NO: 30 | iv. Quantitative PCR

Figure 12A:
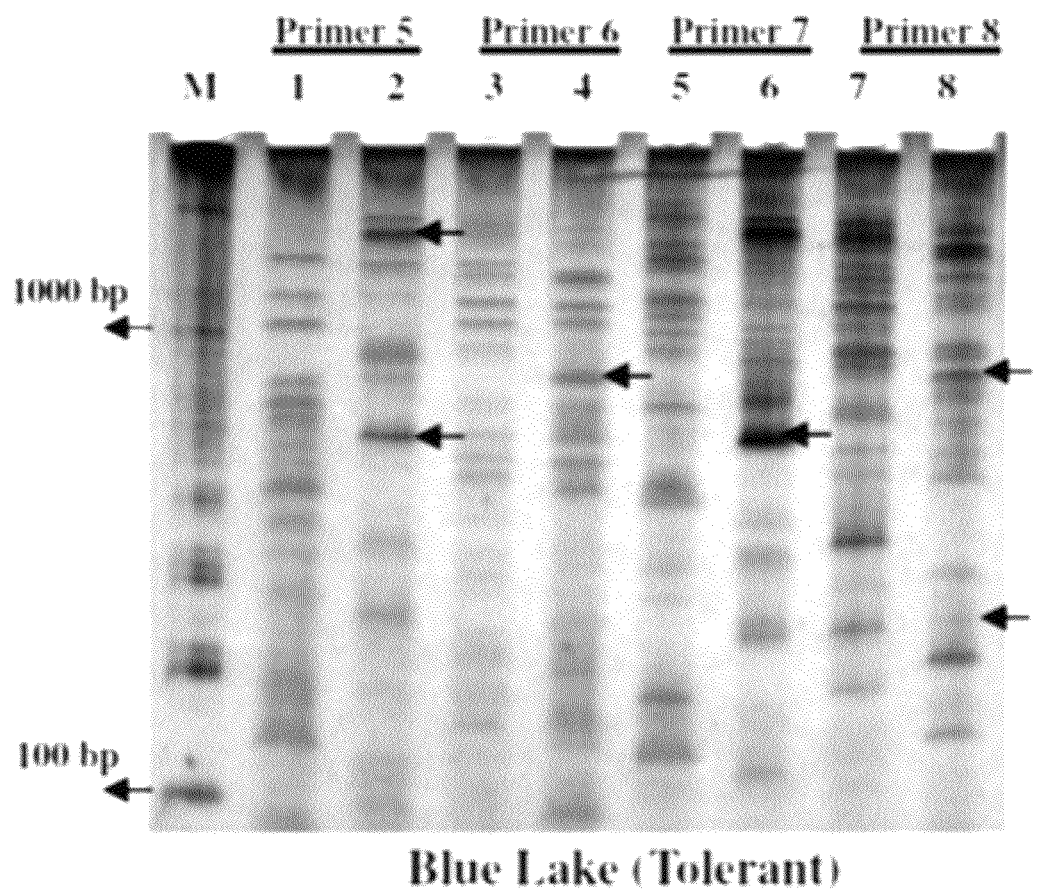
FIGS. 12A-12B depict a gel profile representing transcripts induced upon infection with *E. ampelina*, wherein Lane M=100 bp molecular marker; Lanes 1, 3, 5, 7=uninfected leaf RNA; Lanes 2, 4, 6, 8=infected leaf RNA; and Lane C=control (sterile water).
Figure 12B:
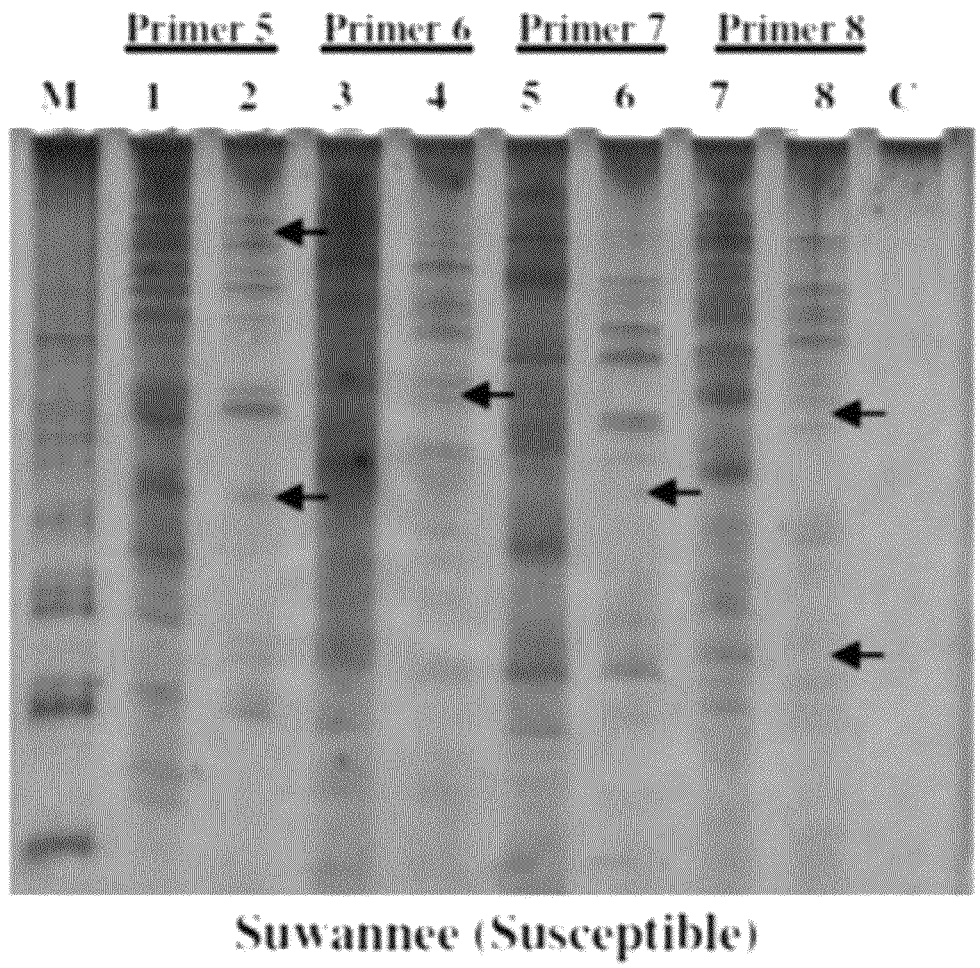

Real-time PCR was performed to confirm the expression of defense-related genes in anthracnose-tolerant and anthracnose-susceptible grapevine cultivars. Total RNA was treated with DNase (QIAGEN) to remove DNA pollution and subsequently purified with the RNeasy Cleanup Kit (QIAGEN). RNA was reverse transcribed to cDNA by means of the iScript reverse transcription system (Bio-Rad). Prior to real-time PCR analysis, a standard control PCR was carried out to check for the presence of genomic DNA contamination. PCR reactions contained 2 µL of diluted cDNA, 2 µL of 10×PCR Buffer (Promega), 0.4 µL 10 mM dNTPs (Promega), 1.6 µL 2 mM MgCl2, 1 U Taq DNA polymerase (Promega), and 2 µL of each gene-specific primer (10 µM/µL, Operon Biotechnologies, Inc) and were brought to a final reaction volume of FIGS. 12A-12B depict a gel profile representing transcripts induced upon infection with *Elsinoë ampelina*, wherein Lane M=100 bp molecular marker; Lanes 1, 3, 5, 7=uninfected leaf RNA; Lanes 2, 4, 6, 8=infected leaf RNA; and Lane C=control (sterile water). FIG. 12A shows the gel of cultivar Blue Lake (anthracnose-tolerant). FIG. 12B shows the gel of cultivar Suwanee (anthracnose-susceptible).

3. Conclusions

Plants respond to pathogen infestation by expressing genes encoding defense-related proteins which are believed to play a role in plant defense. Polygalacturonase-inhibiting proteins are extracellular plant proteins capable of inhibiting fungal endopolygalacturonases (PGs) [29], thereby protecting the plants against pathogens, whereas chitinases (CHI) are capable of hydrolyzing chitin-containing fungal cell walls and therefore play a major role in plant defense [30]. Lipid-transfer protein (LTP) has been reported to exhibit antifungal activity and is also involved in triggering many important cell-signaling and metabolic pathways upon fungal infection [31].

Stilbene synthase expression was also found at higher levels in anthracnose-tolerant cv. 'Noble' and other cultivars studied. Expression of stilbene synthase genes was also found at lower levels in susceptible cultivars (FIG. 9B), because their production has been reported to occur even in the absence of the usual stimulus [32,33]. Phytoalexins are considered as strong fungistatic substances [34]. The role of phytoalexins in defense has been demonstrated in several crops [35,36], including the grapevine [37]. Stilbene synthase produces trans-resveratrol, the major phytoalexin in the plant. This triphenol is subsequently metabolized into other phytoalexins of grapevine. Resveratrol plays an important role in tolerance to colonization by fungi and exhibits outstanding biological properties in human health [37]. The transgenic plant possessing grapevine stilbene synthase genes are known to improve plant tolerance to fungal diseases particularly to downy mildew (*Pseudoperonospora humuli*), powdery mildew (*Podosphaera macularis*), *Botrrtis cinerea*, *Eutypa lata*, *Plasmopara viticola* and *Phomopsis viticola* [38-41].

The expression of stilbene synthase gene in anthracnose-tolerant cv. 'Noble' and other tolerant muscadine cultivars indicates its possible tolerance mechanism within the plant against the fungal pathogen *E. ampelina*. This clearly shows that the induction of these antifungal genes in anthracnose-tolerant muscadine cultivars may indeed reduce the damage caused by *Elsinoë*. Anthracnose tolerance level varies widely among muscadine genotypes, and the tolerant genotypes produce several defense-related genes to overcome pathogen infection.

Through accurate screening of muscadine grape germplasm for anthracnose disease tolerance by bioassay with specific toxic compound produced from pathogen, pathogen inoculation, and field tests coupled with gene expression studies, it is possible to select resistant muscadine grape genetic resources to be utilized in breeding programs. This study also demonstrates an efficient screening system could be a valuable tool in examining the degree of tolerance in muscadine grape cultivars for future use in grape crop improvement.

4. References

1. Kitajima, H. Diseases in grapes. In *Diseases in Fruit Trees*; Kitajima, H., Ed.; Youkendo Press: Tokyo, Japan, 1989; pp. 396-453.
2. Magarey, R. D.; Coffey, B. E.; Emmet, R. W. Anthracnose of grapevines, a review. *Plant Protect. Q.* 1993, 8, 106-110.
3. Mirica, I. I. *Compendium of Grape Diseases*; Pearson, R. C., Gohen, A. C., Eds.; American Phytopathological Society Press: St. Paul, Minn., USA, 1994; pp. 18-19.
4. Vidhyasekaran, P.; Charan, A. Osmotic pressure of grapevine leaves in relation to anthracnose disease incidence. *Ind. J. Exp. Biol.* 1972, 10, 398-399.
5. Wang, Y.; Liu, Y.; He, P.; Lamikanra, O.; Lu, J. Resistance of Chinese *Vitis* species to *Elsinoe ampelina* shear. *Hort Science* 1998, 33, 123-126.
6. Mortensen, J. A. Sources and inheritance of resistance to anthracnose in *Vitis. J. Hered.* 1981, 72 (6), 423-426.
7. Olmo, H. P. *Vinifera rotundifolia* hybrids as wine grapes. *Am. J. Enol. Vitic.* 1971, 22, 87-91.
8. Clarke, E.; Ren, Z.; Lu, J. Evaluation of grape germplasm for resistance to pierce disease. *Proc. Fla. State Hort. Soc.* 2003, 116, 32-35.
9. Lu, J.; Schell, L.; Ramming, D. W. Interspecific hybridization between *Euvitis* and *Muscadinia* grape species. *Acta Hort.* 2000, 528, 479-486.
10. Ren. Z.; Lu, J. Muscadine rootsctock increased the resistance of Florida hybrid bunch grapes. *Proc. Fla. State Hort. Soc.* 2000, 115, 108-110.
11. Xu, X.; Huang, H.; Lu, J. Investigating the *Xylella fastidiosa* in Pierce's disease resistant and susceptible grapevines. *Proc. Fla. State Hort. Soc.* 2002, 115, 105-108.
12. Yun, H. K.; Park, K. S.; Rho, J. H.; Kwon, B. O.; Jeong, S. B. Development of an efficient screening system for anthracnose resistance in grapes. *J. Kor. Soc Hort. Sci.* 2003, 44, 809-812.
13. Biggs, A. R.; Grove, G. G. Role of the world wide web in extension plant pathology: Case studies in tree fruits and grapes. *Plant Dis.* 1998, 82, 452-464.
14. Yun, H. K.; Lu, J.; Louime, C. First report of anthracnose caused by *Elsinoe ampelina* on muscadine grapes (*Vitis rotundifolia*) in northern Florida. *Plant Dis.* 2007, 91, 905-906.
15. Pringle, R. B.; Braun, A. C. The isolation of the toxin of *Helminthosporiuim victoriae*. *Phytopathology* 1957, 47, 369-371.
16. Muller, K. O. Studies on phytoalexins I. The formation and the immunological significance of phytoalexin produced by *Phaseolus vulgaris* in response to infections with *Sclerotinia fructicola* and *Phytophfhora infestans*. *Aust. J Biol. Sci.* 1958, 11,275-300.
17. Vasanthaiah, H. K. N.; Katam, R.; Basha, S. M. Efficient protocol for isolation of functional RNA from different grape tissue rich in polyphenols and polysaccharides for gene expression studies. *Electron. J. Biotech.* 2008, 11 (3), 1-8.
18. Sambrook, J.; Fritsch, E. F.; Maniatis, T. *Molecular Cloning: A Laboratory Manual*, 2nd ed.; Cold Spring Harbor Laboratory Press: Woodbury, N.Y., USA, 2000.
19. Vasanthaiah, H. K. N.; Katam, R.; Basha, S. M. Characterization of unique and differentially expressed proteins in anthracnose-tolerant Florida hybrid bunch grapes. *Appl. Biochenm. Biotech.* 2009, 157 (3), 395-406.
20. Kohmoto, K.; Taniguchi, T.; Nishimura, S. Correlation between the susceptibility of apple cultivars to *Alternaria mali* and their sensitivity to AM-toxin I. *Ann. Phytopath. Soc. Japan* 1997, 43, 65-68.
21. Yun, H. K.; Yu, S. H. Evaluation of grapevine varietal resistance to anthracnose through treating culture filtrates from *Elsinoe ampelina*. *Kor. J. Plant Pathol.* 1992, 8, 185-189.
22. Otani, H.; Kohmoto, K.; Nishimura, S.; Nakashima, T.; Ueno, T.; Fukami, H. Biological activity of Ak toxin I and II, host specific toxins from *Alternaria alternata* Japanese pear pathotype. *Ann. Phytopath. Soc. Japan* 1985, 51, 285-293.
23. Park, J. S.; Yu, S. H. Evaluation of pear cultivar susceptibility to AK-toxin produced by *Alternaria kikuchia*. *Res. Rep. Agri. Sci. Tech.* 1998, 15, 1-8.
24. Jacobs, A. K.; Dry, I. B.; Robinson, S. P. Induction of different pathogenesis-related cDNAs in grapevine infected with powdery mildew and treated with ethephon. *Plant Pathol.* 1999, 48 (3), 325-336.
25. Terlizzi, F.; Ratti, C.; Filippini, G.; Pisi, A.; Credi, R. Detection and molecular characterization of Italian *Grapevine rupestris* stem pitting-associated virus isolates. *Plant Pathol.* 2009, 59 (1), 48-58.

26. Dron, M.; Clouse, S. D.; Dixon, R. A.; Lawton, M. A.; Lamb, C. J. Glutathione and fungal elicitor regulation of a plant defense gene promoter in electroporated protoplasts. *Proc. Natl. Acad. Sci. USA* 1988, 85 (18), 6738-6742.
27. Hahlbrock, K.; Scheel, D. Physiology and molecular biology of phenylpropanoid metabolism. *Annu. Rev. Plant Physiol. Plant Mol. Biol.* 1989, 40, 347-369.
28. Vijayan, P.; Shockey, J.; Levesque, A.; Cook, R. J.; Browse, J. A role for jasmonate in pathogen defense of *Arabidopsis. Proc. Natl. Acad. Sci. USA* 1998, 95 (12), 7209-7214.
29. Lorenzo, G. D. L.; D'Ovidio, R.; Cervone, F. The crystal structure of polygalacturonase-inhibiting protein (PGIP), a leucine-rich repeat protein involved in plant defense. *Annu. Rev. Phytopathol.* 2001, 39, 313-335.
30. Schickler, H.; Chet, I. Heterologous chitinase gene expression to improve plant defense against phytopathogenic fungi. *J. Ind. Microbiol. Biotech.* 1997, 19 (3), 196-201.
31. Blein, J. P.; Thevenot, P. C.; Marion, D.; Ponchet, M. From elicitins to lipid-transfer proteins: A new insight in cell signalling involved in plant defence mechanisms. *Trends Plant Sci.* 2002, 7 (7), 293-296.
32. Sanders, T. H.; McMichael, R. W.; Hendrix, K. W. Occurrence of resveratrol in edible peanuts. *J. Agr. Food Chem.* 2000, 48, 1243-1246.
33. Vasanthaiah, H. K. N.; Basha, S. M.; Katam, R. Differential expression of chitinase and stilbene synthase genes in Florida hybrid bunch grapes to *Elsinoë ampelina* infection. *J. Plant Growth Regul.* 2010, 61 (2), 127-134.
34. Miller, M.; Germani, J.; van Der, S. The use of RAPD to characterize *Bipolaris sorokiniana* isolates. *Genet. Mol. Res.* 2005, 4, 642-652.
35. Keen, N. T.; Littlefield, L. J. The possible involvement of phytoalexins with resistance gene expression in flax. *Physiol. Plant Pathol.* 1979, 14, 265-280.
36. Long, M.; Barton-Wills, P.; Staskawicz, B. J.; Dahlbeck, D.; Keen, N. T. Further studies on the relationship between glyceollin accumulation and the resistance of soybean leaves to *pseudomonas syringae. Phytopathology* 1985, 75, 235-239.
37. Jeandet, P.; Douillet-Breuil, A. C.; Bessis, R.; Debord, S.; Sbaghi, M.; Adrian, M. Phytoalexins from the Vitaceae: Biosynthesis, phytoalexin gene expression in transgenic plants, antifungal activity and metabolism. *J. Agr. Food Chem.* 2002, 50, 2731-2741.
38. Schwekendiek, A.; Horlemann, C.; Spring, O.; Stanke, M.; Hohnle, M.; Weber, G. Transformation with stilbene synthase for increasing resistance against fungal pathogens. *Acta Hort.* 2005, 668, 101-108.
39. Thevenot, P. C.; Poinssot, B.; Bonomeli, A.; Yean, H.; Breda, C.; Buffard, D.; Esnault, R.; Hain, R.; Boulay, M. In vitro tolerance to Botrytis cinerea of grapevine 41B rootstock in transgenic plants expressing the stilbene synthase Vst1 gene under the control of a pathogen-inducible PR 10 promoter. *J. Exp. Bot.* 2001, 52 (358), 901-910.
40. Dai, G. H.; Andary, C.; Mondolot-Cosson, L.; Boubals, D. Histochemical responses of leaves of in vitro plantlets of *Vitis* spp. to infection with *Plasmopara viticola. Phytopathology* 1995, 85, 149-154.
41. Montero, C.; Cristescu, S. M.; Jimenez, J. B.; Orea, J. M.; Hekkert, S. T. L.; Harren, F. J. M.; Urena, A. G. Trans-resveratrol and grape disease resistance. A dynamical study by high-resolution laser-based techniques. *Plant Physiol.* 2003, 131, 129-138.
Louime C, Lu J, Onokpise O, Vasanthaiah H K N, Kambiranda D, Basha M, and Yun H K. 2011. Resistance to *Elisnoë ampelina* and Expression of Related Resistant Genes in *Vitis rotundifolia* Michx. Grapes. International Journal of Molecular Sciences 12(6): 3473-3488.
Vasanthaiah H K N and Basha S M. 2008. Differentially expressional of genes in anthracnose-tolerant Florida hybrid bunch grape cultivars. NCBI GenBank_Accn: GE639560 to GE 639565.
Vasanthaiah H K N, Katam R and Basha S M. 2009. Cloning and Characterization of Genes Associated with Anthracnose Tolerance in Florida Hybrid Bunch Grapes. 15th Biennial ARD Research Symposium, Atlanta, Ga., March 31-April 3 (Poster—P126).
Vasanthaiah H K N, Katam R, Basha S M. 2009. Functional Genomics Approach to Identify Genes Associated with Anthracnose Resistance in Florida Hybrid Bunch Grapes, Plant and Animal Genome conference (PAG-XVII), San Diego, Calif., January 10-14.

IV. Application of cDNA Sequence Data

Using known small RNA technology, the foregoing cDNA sequence data can be applied to promote expression of disease tolerance-related genes to induce production of disease-tolerance related gene products for resisting disease occurrence. Small RNAs can serve as activators of gene expression by targeting regulatory sequences in the gene. Small RNAs offers a new approach to enhance endogenous gene expression, which may be manipulated to target a variety of genes for modifying gene expression.

Plants use small RNAs in post-transcriptional regulation and are predominantly implicated in regulating critical pathways, such as disease resistance and stress response. Small RNAs bind to mRNAs and can be used to achieve expression/suppression of the identified genes.

Full length sequence information, as seen in this specification, reveal small RNA-mRNA regulation and can be used to modify gene expression in disease susceptible plants. The cDNA sequences listed herein that are demonstrated to be related to tolerance of anthracnose and Pierce's disease, for example, can be used to identify their corresponding small RNAa using bioinformatics prediction tools, such as MIRcheck, MIRFINDER and find miRNA.

Primers can then be designed and optimized for the identified small RNAs to reveal induction of gene expression following elevated small RNA expression. Real time PCR can be performed using the identified miRNA primers to monitor the expression levels in berry and leaf tissues. Confirmed miRNAs can be cloned into expression vectors, and binding assays can be performed to screen their efficiency in interacting with 3' untranslated regions (UTR) and regulate up and down regulation of genes. Sequence information obtained through the foregoing studies is crucial in identifying their corresponding regulatory RNAs to modify gene expression.

All referenced patents, patent applications, and other publications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall there between.

What is claimed is:

1. An isolated complementary DNA coding for a stilbene synthase gene in *V. rotundifolia*, wherein the complementary DNA coding has the nucleotide sequence set forth in SEQ ID NO:1.

\* \* \* \* \*